(12) United States Patent
Olson et al.

(10) Patent No.: US 9,888,973 B2
(45) Date of Patent: Feb. 13, 2018

(54) INTUITIVE USER INTERFACE CONTROL FOR REMOTE CATHETER NAVIGATION AND 3D MAPPING AND VISUALIZATION SYSTEMS

(75) Inventors: Eric S. Olson, Maplewood, MN (US); John A. Hauck, Shoreview, MN (US); Nicholas A. Patronik, Minneapolis, MN (US); Cem M. Shaquer, Los Gatos, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 700 days.

(21) Appl. No.: 13/637,401

(22) PCT Filed: Mar. 31, 2011

(86) PCT No.: PCT/US2011/030764
§ 371 (c)(1),
(2), (4) Date: Dec. 6, 2012

(87) PCT Pub. No.: WO2011/123669
PCT Pub. Date: Oct. 6, 2011

(65) Prior Publication Data
US 2013/0172906 A1 Jul. 4, 2013

Related U.S. Application Data

(60) Provisional application No. 61/319,795, filed on Mar. 31, 2010.

(51) Int. Cl.
*A61B 19/00* (2006.01)
*A61B 34/30* (2016.01)
(Continued)

(52) U.S. Cl.
CPC .............. *A61B 34/30* (2016.02); *A61B 34/71* (2016.02); *A61B 34/74* (2016.02); *A61B 34/25* (2016.02);
(Continued)

(58) Field of Classification Search
CPC ........ A61B 19/2203; A61B 2019/2207; A61B 2019/2269; A61B 34/30; A61B 34/71;
(Continued)

(56) References Cited

U.S. PATENT DOCUMENTS

| | | | |
|---|---|---|---|
| 3,091,130 A | 5/1963 | Payerle et al. | |
| 3,605,725 A | 9/1971 | Bentov | |

(Continued)

FOREIGN PATENT DOCUMENTS

| | | |
|---|---|---|
| EP | 0151479 | 8/1985 |
| EP | 09094796 | 3/1999 |

(Continued)

OTHER PUBLICATIONS

"International Search Report and Written Opinion", PCT/US2011/030764 dated Jun. 15, 2011.

(Continued)

*Primary Examiner* — David Harvey
(74) *Attorney, Agent, or Firm* — Dykema Gossett PLLC

(57) ABSTRACT

The present disclosure relates to a control system for user-guided robotic control of a medical device and includes an electronic control unit, a computer-readable memory coupled to the ECU, and a visualization system configured to provide a view of an anatomical model. The memory contains user interface logic configured to be executed by the ECU, and configured to obtain input from a touch screen display with respect to the view of an anatomical model. Control logic stored in the memory is also configured to be executed by said ECU and is configured to produce an (Continued)

actuation control signal responsive to the input to control actuation of a manipulator assembly so as to move the medical device.

17 Claims, 84 Drawing Sheets

(51) Int. Cl.
  *A61B 17/00* (2006.01)
  *A61B 34/00* (2016.01)
  *A61B 90/00* (2016.01)
(52) U.S. Cl.
  CPC .............. *A61B 2017/00477* (2013.01); *A61B 2034/301* (2016.02); *A61B 2034/742* (2016.02); *A61B 2090/372* (2016.02)
(58) Field of Classification Search
  CPC .................... A61B 34/25; A61B 34/74; A61B 2017/00477; A61B 2034/742; A61B 2090/372
  USPC ......................................................... 348/77
  See application file for complete search history.

(56) References Cited

U.S. PATENT DOCUMENTS

| | | | |
|---|---|---|---|
| 3,893,449 A | 7/1975 | Lee et al. | |
| 4,160,508 A | 7/1979 | Frosch et al. | |
| 4,348,556 A | 9/1982 | Gettig et al. | |
| 4,393,728 A | 7/1983 | Larson et al. | |
| 4,494,417 A | 1/1985 | Larson | |
| 4,543,090 A | 9/1985 | McCoy | |
| 4,758,222 A | 7/1988 | McCoy | |
| 4,784,042 A | 11/1988 | Paynter | |
| 4,802,487 A | 2/1989 | Martin et al. | |
| 4,884,557 A | 12/1989 | Takehana et al. | |
| 4,962,448 A | 10/1990 | DeMaio et al. | |
| 4,974,151 A | 11/1990 | Advani et al. | |
| 5,078,140 A * | 1/1992 | Kwoh .................... | A61B 34/30 378/20 |
| 5,107,080 A | 4/1992 | Rosen | |
| 5,170,817 A | 12/1992 | Sunderland | |
| 5,238,005 A | 8/1993 | Imran | |
| 5,298,930 A | 3/1994 | Asakura et al. | |
| 5,303,148 A | 4/1994 | Mattson | |
| 5,318,525 A | 6/1994 | West et al. | |
| 5,339,799 A | 8/1994 | Kami et al. | |
| 5,396,266 A | 3/1995 | Brimhall et al. | |
| 5,410,638 A | 4/1995 | Colgate et al. | |
| 5,441,483 A | 8/1995 | Avitall | |
| 5,449,345 A | 9/1995 | Taylor et al. | |
| 5,520,644 A | 5/1996 | Imran | |
| 5,533,967 A | 7/1996 | Imran | |
| 5,545,200 A | 8/1996 | West et al. | |
| 5,579,442 A | 11/1996 | Kimoto et al. | |
| 5,607,158 A | 3/1997 | Chan | |
| 5,607,462 A | 3/1997 | Imran | |
| 5,623,582 A | 4/1997 | Rosenberg | |
| 5,630,783 A | 5/1997 | Steinberg | |
| 5,661,253 A | 8/1997 | Aoki | |
| 5,706,827 A | 1/1998 | Ehr et al. | |
| 5,784,542 A | 7/1998 | Ohm et al. | |
| 5,791,908 A | 8/1998 | Gillio | |
| 5,800,178 A | 9/1998 | Gillio | |
| 5,807,377 A | 9/1998 | Madhani et al. | |
| 5,808,665 A | 9/1998 | Green | |
| 5,828,813 A | 10/1998 | Ohm | |
| 5,854,622 A | 12/1998 | Brannon | |
| 5,861,024 A | 1/1999 | Rashidi | |
| 5,876,325 A | 3/1999 | Mizuno et al. | |
| 5,897,488 A | 4/1999 | Ueda | |
| 5,913,820 A | 6/1999 | Bladen | |
| 6,040,758 A | 3/2000 | Sedor et al. | |
| 6,063,095 A | 5/2000 | Wang et al. | |
| 6,113,395 A | 9/2000 | Hon | |
| 6,201,196 B1 | 3/2001 | Wergen | |
| 6,233,476 B1 | 5/2001 | Strommer | |
| 6,233,504 B1 | 5/2001 | Das et al. | |
| 6,272,370 B1 * | 8/2001 | Gillies ............. | A61M 25/0105 324/309 |
| 6,290,683 B1 | 9/2001 | Erez et al. | |
| 6,348,911 B1 | 2/2002 | Rosenberg et al. | |
| 6,358,207 B1 | 3/2002 | Lathbury | |
| 6,385,509 B2 | 5/2002 | Das et al. | |
| 6,396,232 B2 | 5/2002 | Haanpaa et al. | |
| 6,432,112 B2 | 8/2002 | Brock et al. | |
| 6,498,944 B1 | 12/2002 | Ben-Haim | |
| 6,500,167 B1 | 12/2002 | Webster, Jr. | |
| 6,522,141 B2 | 2/2003 | Debbins | |
| 6,540,685 B1 | 4/2003 | Rhoads | |
| 6,671,533 B2 | 12/2003 | Chen | |
| 6,709,667 B1 | 3/2004 | Lowe et al. | |
| 6,785,358 B2 | 8/2004 | Johnson | |
| 6,850,252 B1 | 2/2005 | Hoffberg | |
| 6,869,390 B2 | 3/2005 | Elliott et al. | |
| 6,869,396 B2 | 3/2005 | Belson | |
| 6,968,223 B2 | 11/2005 | Hanover | |
| 7,016,469 B2 | 3/2006 | Johnson | |
| 7,193,521 B2 | 3/2007 | Moberg et al. | |
| 7,197,354 B2 | 3/2007 | Sobe | |
| 7,199,790 B2 | 4/2007 | Rosenberg et al. | |
| 7,247,139 B2 | 7/2007 | Yudkovitch | |
| 7,263,397 B2 | 8/2007 | Hauck | |
| 7,276,044 B2 | 10/2007 | Ferry et al. | |
| 7,386,339 B2 | 6/2008 | Strommer | |
| 7,465,288 B2 | 12/2008 | Dudney | |
| 7,672,849 B2 | 3/2010 | Yudkovitch | |
| 7,698,966 B2 | 4/2010 | Gosselin | |
| 7,742,803 B2 | 6/2010 | Viswanathan | |
| 7,850,642 B2 | 12/2010 | Moll et al. | |
| 7,880,717 B2 | 2/2011 | Berkley et al. | |
| 7,945,546 B2 | 5/2011 | Bliss | |
| 7,963,288 B2 | 6/2011 | Rosenberg et al. | |
| 8,164,573 B2 * | 4/2012 | DaCosta ............... | G06F 3/0418 178/18.01 |
| 8,317,744 B2 | 11/2012 | Kirschenman | |
| 8,317,745 B2 | 11/2012 | Kirschenman et al. | |
| 8,332,072 B1 * | 12/2012 | Schaible ............ | A61B 19/2203 606/1 |
| 8,390,438 B2 | 3/2013 | Olson et al. | |
| 8,416,203 B2 * | 4/2013 | Tsui .................... | G06F 3/04886 178/18.01 |
| 8,560,118 B2 * | 10/2013 | Greer et al. .................. | 700/247 |
| 8,926,511 B2 | 1/2015 | Bar-Tal | |
| 9,314,311 B2 * | 4/2016 | Wenderow ........... | A61B 5/7475 |
| 2001/0018591 A1 | 8/2001 | Brock et al. | |
| 2001/0025183 A1 * | 9/2001 | Shahidi ........................ | 606/130 |
| 2002/0065485 A1 | 5/2002 | DuBois et al. | |
| 2002/0068868 A1 | 6/2002 | Thompson et al. | |
| 2002/0072704 A1 | 6/2002 | Mansouri-Ruiz | |
| 2002/0087048 A1 | 7/2002 | Brock et al. | |
| 2002/0184055 A1 | 12/2002 | Naghavi et al. | |
| 2003/0018232 A1 | 1/2003 | Elliott et al. | |
| 2003/0050733 A1 | 3/2003 | Wang et al. | |
| 2003/0114962 A1 | 6/2003 | Niemeyer | |
| 2003/0121382 A1 | 7/2003 | Morson | |
| 2004/0050247 A1 | 3/2004 | Topping | |
| 2004/0068173 A1 | 4/2004 | Viswanathan | |
| 2004/0133189 A1 | 7/2004 | Sakurai | |
| 2004/0138530 A1 | 7/2004 | Kawai et al. | |
| 2004/0146388 A1 | 7/2004 | Khajepour et al. | |
| 2004/0193239 A1 | 9/2004 | Falwell et al. | |
| 2004/0223636 A1 * | 11/2004 | Edic ....................... | G06T 7/0012 382/131 |
| 2004/0243147 A1 | 12/2004 | Lipow | |
| 2005/0038333 A1 * | 2/2005 | Sra ..................... | A61B 18/1492 600/374 |
| 2005/0075538 A1 | 4/2005 | Banik et al. | |
| 2005/0172405 A1 | 8/2005 | Menkedick et al. | |
| 2005/0203382 A1 | 9/2005 | Govari et al. | |
| 2005/0222554 A1 | 10/2005 | Wallace et al. | |
| 2005/0234293 A1 | 10/2005 | Yamamoto et al. | |

(56) References Cited

U.S. PATENT DOCUMENTS

| | | |
|---|---|---|
| 2005/0234320 A1 | 10/2005 | Balasubramanian |
| 2006/0052664 A1 | 3/2006 | Julian et al. |
| 2006/0078195 A1* | 4/2006 | Vaillant .................. A61B 6/032 382/154 |
| 2006/0089637 A1 | 4/2006 | Werneth et al. |
| 2006/0155321 A1 | 7/2006 | Bressler et al. |
| 2006/0276775 A1 | 12/2006 | Rosenberg et al. |
| 2006/0293643 A1 | 12/2006 | Wallace |
| 2007/0016008 A1 | 1/2007 | Schoenefeld |
| 2007/0022364 A1 | 1/2007 | Abbott |
| 2007/0043338 A1* | 2/2007 | Moll .................... A61B 17/062 606/1 |
| 2007/0060833 A1 | 3/2007 | Hauck |
| 2007/0073137 A1 | 3/2007 | Schoenefeld et al. |
| 2007/0100254 A1 | 5/2007 | Murakami et al. |
| 2007/0120512 A1 | 5/2007 | Albu-Schaffer et al. |
| 2007/0135803 A1 | 6/2007 | Belson |
| 2007/0142726 A1 | 6/2007 | Carney et al. |
| 2007/0172803 A1* | 7/2007 | Hannaford et al. .......... 434/262 |
| 2007/0185404 A1* | 8/2007 | Hauck .................. A61B 5/6885 600/509 |
| 2007/0185485 A1 | 8/2007 | Hauck |
| 2007/0185486 A1 | 8/2007 | Hauck et al. |
| 2007/0197896 A1 | 8/2007 | Moll et al. |
| 2007/0197939 A1 | 8/2007 | Wallace et al. |
| 2007/0198008 A1 | 8/2007 | Hauck |
| 2007/0233044 A1 | 10/2007 | Wallace |
| 2007/0233045 A1 | 10/2007 | Weitzner et al. |
| 2007/0257821 A1* | 11/2007 | Son ........................ G06F 3/016 341/22 |
| 2007/0268269 A1* | 11/2007 | Chang .................. G06F 3/0416 345/173 |
| 2007/0270685 A1 | 11/2007 | Kang et al. |
| 2007/0276214 A1* | 11/2007 | Dachille ............... G06T 7/0012 600/407 |
| 2007/0298877 A1 | 12/2007 | Rosenberg et al. |
| 2008/0009791 A1 | 1/2008 | Cohen |
| 2008/0013809 A1 | 1/2008 | Zhu et al. |
| 2008/0112842 A1 | 5/2008 | Edwards |
| 2008/0201847 A1 | 8/2008 | Menkedick et al. |
| 2008/0297490 A1* | 12/2008 | Adkins ............... G06F 3/03545 345/179 |
| 2008/0312536 A1 | 12/2008 | Dala-Krishna |
| 2009/0012533 A1 | 1/2009 | Barbagli |
| 2009/0061928 A1* | 3/2009 | Lee .......................... G06F 3/038 455/556.1 |
| 2009/0123111 A1 | 5/2009 | Udd |
| 2009/0137952 A1* | 5/2009 | Ramamurthy et al. .... 604/95.01 |
| 2009/0177454 A1* | 7/2009 | Bronstein ............... G06T 17/20 703/11 |
| 2009/0192519 A1 | 7/2009 | Omori et al. |
| 2009/0195514 A1 | 8/2009 | Glynn |
| 2009/0247993 A1 | 10/2009 | Kirschenman |
| 2009/0264156 A1 | 10/2009 | Burghardt |
| 2009/0322697 A1 | 12/2009 | Cao |
| 2009/0327886 A1* | 12/2009 | Whytock .............. G06F 3/0421 715/702 |
| 2010/0066676 A1 | 3/2010 | Kramer et al. |
| 2010/0073150 A1 | 3/2010 | Olson |
| 2010/0079386 A1* | 4/2010 | Scott ..................... G06F 3/0481 345/173 |
| 2010/0082039 A1* | 4/2010 | Mohr et al. .................... 606/130 |
| 2010/0103127 A1* | 4/2010 | Park .................... G06F 3/04886 345/173 |
| 2010/0198402 A1* | 8/2010 | Greer .................. A61B 19/201 700/247 |
| 2010/0256558 A1 | 10/2010 | Olson et al. |
| 2010/0268067 A1 | 10/2010 | Razzaque et al. |
| 2010/0312095 A1* | 12/2010 | Jenkins ................. A61B 5/415 600/411 |
| 2010/0314031 A1 | 12/2010 | Heideman et al. |
| 2011/0040547 A1 | 2/2011 | Gerber et al. |
| 2011/0128555 A1 | 6/2011 | Rotschild |
| 2011/0137156 A1 | 6/2011 | Razzaque |
| 2011/0144806 A1* | 6/2011 | Sandhu .............. A61B 19/2203 700/264 |
| 2011/0152882 A1* | 6/2011 | Wenderow et al. .......... 606/130 |
| 2011/0289441 A1 | 11/2011 | Venon et al. |
| 2011/0306986 A1* | 12/2011 | Lee et al. ....................... 606/130 |
| 2012/0071891 A1 | 3/2012 | Itkowitz et al. |
| 2012/0133601 A1 | 5/2012 | Marshall et al. |
| 2012/0277663 A1 | 11/2012 | Millman et al. |
| 2013/0006268 A1 | 1/2013 | Swarup et al. |
| 2013/0154913 A1 | 6/2013 | Genc et al. |
| 2013/0165854 A1 | 6/2013 | Sandhu |
| 2013/0176220 A1 | 7/2013 | Merschon |
| 2013/0179162 A1 | 7/2013 | Merschon |

FOREIGN PATENT DOCUMENTS

| | | |
|---|---|---|
| GB | 2211280 | 6/1989 |
| JP | S60221280 | 11/1985 |
| JP | H06344285 | 12/1994 |
| JP | H8-280709 | 10/1996 |
| JP | H10216238 | 8/1998 |
| JP | 2003024336 | 1/2003 |
| JP | 2007325936 | 12/2007 |
| WO | 9320535 | 10/1993 |
| WO | 96/39944 | 12/1996 |
| WO | WO03/049596 | 6/2003 |
| WO | 2006/120666 | 11/2006 |
| WO | 2007056590 | 5/2007 |
| WO | 2007/088208 | 8/2007 |
| WO | 2007/098494 | 8/2007 |
| WO | 2007/136803 | 11/2007 |
| WO | 2007/143859 | 12/2007 |
| WO | 2007/146325 | 12/2007 |
| WO | WO2008/045831 | 4/2008 |
| WO | 2008/103212 | 8/2008 |
| WO | 2008101228 | 8/2008 |
| WO | 2009/120982 | 10/2009 |
| WO | 2009/120992 | 10/2009 |
| WO | 2009120940 | 10/2009 |
| WO | 2009120992 | 10/2009 |
| WO | WO 2009/120992 A2 * | 10/2009 |
| WO | WO-2010/025338 | 3/2010 |
| WO | WO 2010/025338 A1 * | 3/2010 |
| WO | 2010/059179 | 5/2010 |
| WO | WO-2010/068783 | 6/2010 |
| WO | WO-2010/107916 | 9/2010 |

OTHER PUBLICATIONS

Title: International Search Report and Written Opinion Citation: PCT/US2011/030764 Publication Date: Jun. 15, 2011.

Title: International Search Report & Written Opinion Citation: PCT/US2012/031008 Publication Date: Jul. 20, 2012.

Author: LaBelle, Kathryn Title: Evaluation of Kinect Joint Tracking for Clinical and In-Home Stroke Rehabilitation Tools Citation: <http://netscale.cse.nd.edu/twiki/pub/Edu/KinectRehabilitation/Eval_of_Kinect_for_Rehab.pdf> Publication Date: Dec. 2011.

Title: The Aurora Electromagnetic Tracking System, Aurora Electromagnetic Measurement System—3D Tracking for Medical Guidance Citation: Northern Digital Inc. <URL: http://www.ndigital.com/medical/aurora.pho?act=print> Publication Date: (actual publication date unknown).

Title Polaris Family of Optical Tracking Systems, Polaris Vicra & Spectra—Optical Measurement Systems for Medical Citation: Northern Digital Inc. <URL: http://www.ndigital.com/medical/polarisfamily.php?act=print> Publication Date: (actual publication date unknown).

Title: Apple Wins Strategic Multitouch and Music Tempo Workout Patents Citation: Patently Apple <URL: http://www.patentlyapple.com/patently-apple/2010/04/apple-wins-strategic-multitouch-music-tempo-workout-patents.html> Publication Date: (actual publication date unknown).

Author: Padoy, Nicolas Title: Needle Insertion Revisited (telesurgery in depth), (online) Citation: The John Hopkins University <URL: http://www.youtube.com/watch?v=YsY_A0kLh-g> Publication Date: Jan. 2011.

(56) References Cited

OTHER PUBLICATIONS

Title: About the Kinect for Windows SDK—Microsoft Research (online) Citation: <URL: http://research.microsoft.com/en-us/um/redmond/projects/kinectsdk/about.aspx> Publication Date: (actual publication date unknown).
Title: Emotiv—Brain Computer Interface Technology (online) Citation: <URL: http://www.emotiv.com> Publication Date: (actual publication date unknown).
Title: Emotiv EPOC Software Development Kit—EPOC neuroheadset (online) Citation: <URL: http://www.emotiv.com/store/hardware/epoc/bci/epoc-neuroheadset/> Publication Date: (actual publication date unknown).
Title: Kinect—Wikipedia, the free encyclopedia (online) Citation: <URL: http://en.wikipedia.org/wiki/Kinect> Publication Date: (actual publication date unknown).
Title: Wii Remote—Wikipedia, the free encyclopedia (online) Citation: <http://en.wikipedia.org/wiki/Wii_Remote> Publication Date: (actual publication date unknown).
Title: International Search Report Citation: PCT Application No. PCT/US2009/069712 Publication Date: Feb. 25, 2010 10 pages.
Title: International Search Report Citation: PCT Application No. PCT/US2009/038525 Publication Date: May 27, 2009 2 pages.
Title: International Search Report Citation: PCT Application No. PCT/US2009/038531 Publication Date: May 19, 2009 3 pages.
Title: International Search Report Citation: PCT Application No. PCT/US2009/038533 Publication Date: Jun. 17, 2009 2 pages.
Title: International Search Report Citation: PCT Application No. PCT/US2009/038618 Publication Date: May 22, 2009 2 pages.
Title: International Search Report Citation: PCT Application No. PCT/US2009/038597 Publication Date: May 18, 2009 2 pages.
Title: International Search Report Citation: PCT Application No. PCT/US2009/038534 Publication Date: May 27, 2009 2 pages.
Title: International Search Report Citation: PCT Application No. PCT/US2009/038536 Publication Date: May 28, 2009 2 pages.
Title: International Search Report Citation: PCT Application No. PCT/US2009/058121 Publication Date: Nov. 19, 2009 2 pages.
Title: Supplemental European Search Report Citation: EP Application No. 09724550.0 Publication Date Jul. 10, 2012 6 pages.
Title: Supplemental European Search Report Citation: EP Application No. 09723739.0 Publication Date: Jul. 10, 2012 6 pages.
Title: Supplemental European Search Report Citation: EP Application No. 09726364.4 Publication Date: Jan. 22, 2013 7 pages.
Title: International Search Report Citation: PCT Application No. PCT/US2011/030656 Publication Date: Jun. 13, 2011 8 pages.
Title: Supplemental European Search Report Citation: EP Application No. 09725131.8 Publication Date: Feb. 20, 2013 7 pages.
Title: The Aurora Electromagnetic Tracking System, Aurora Electromagnetic Measurement System—3D Tracking for Medical Guidance Citation: Northern Digital, Inc. <URL: http://www.ndigital.com/medical/aurora.pho?act=print> Publication Date: (actual publication date unknown).
Title: Supplemental European Search Report Citation: EP Application No. 11763450.1 Publication Date: Oct. 29, 2014 9 pages.
Supplementary European Search Report for EP Application No. 11763410.5, dated Jun. 10, 2015, 7 pages.
Ghobadi, et al. "Real Time Hand Based Robot Control Using Multimodal Images", IAENG International Journal of Computer Sciences, 35:4, IJCS_35_4_08; Nov. 20, 2008. 6pgs.
Robot.pdf (Robot-Definition at Dictionary.com, Oct. 27, 2015, http://dictionary.reference.com/browse/robot, pp. 1-5).

\* cited by examiner

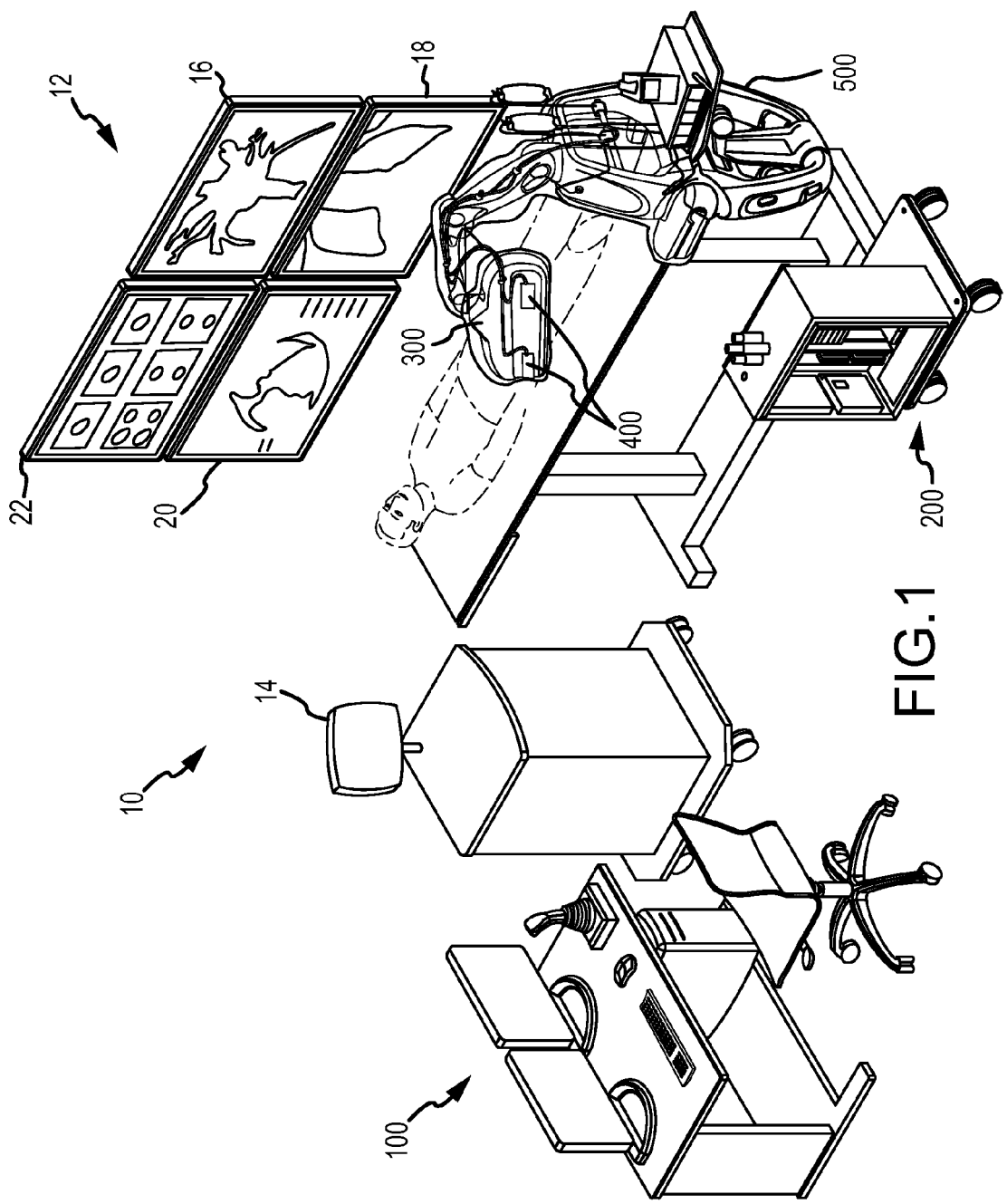

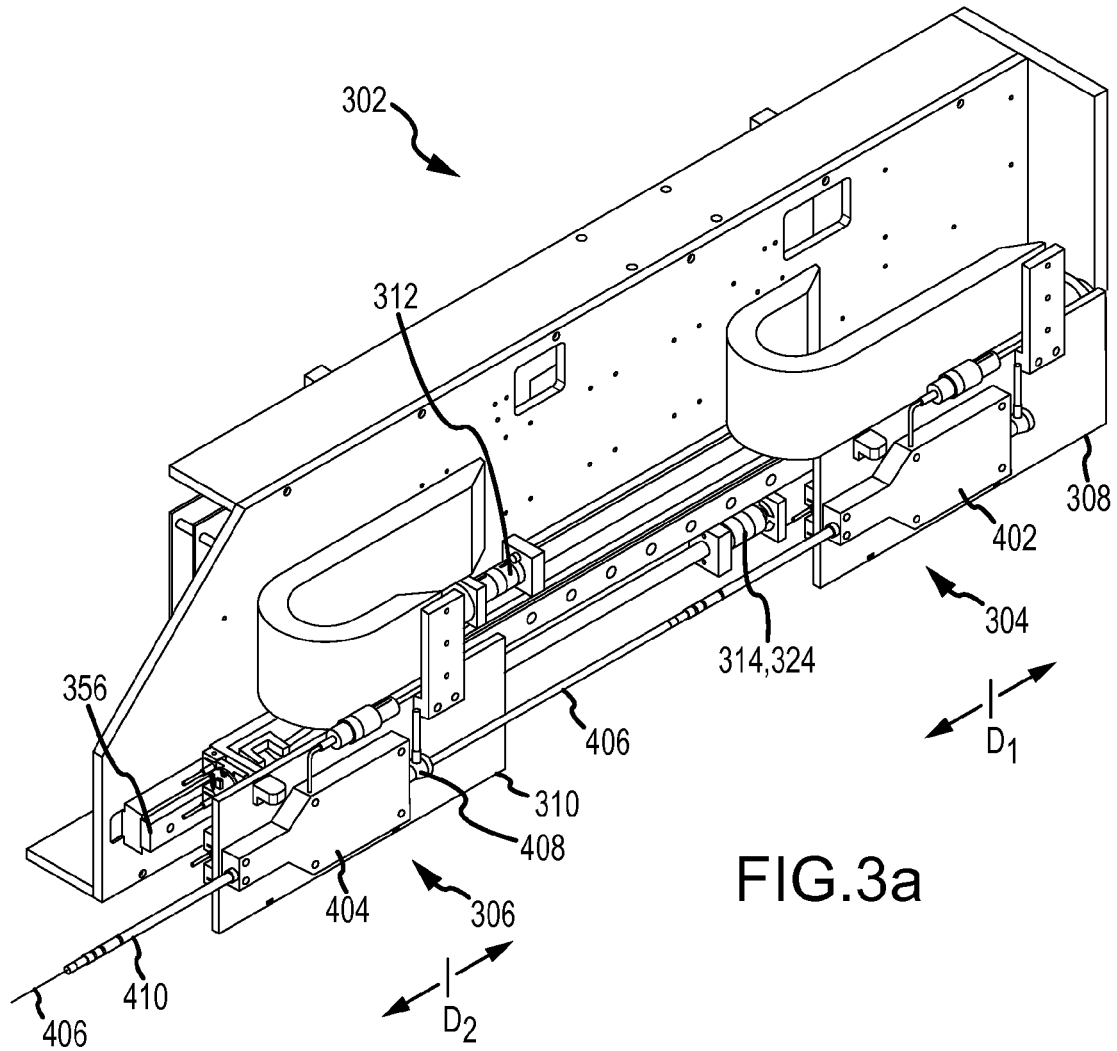
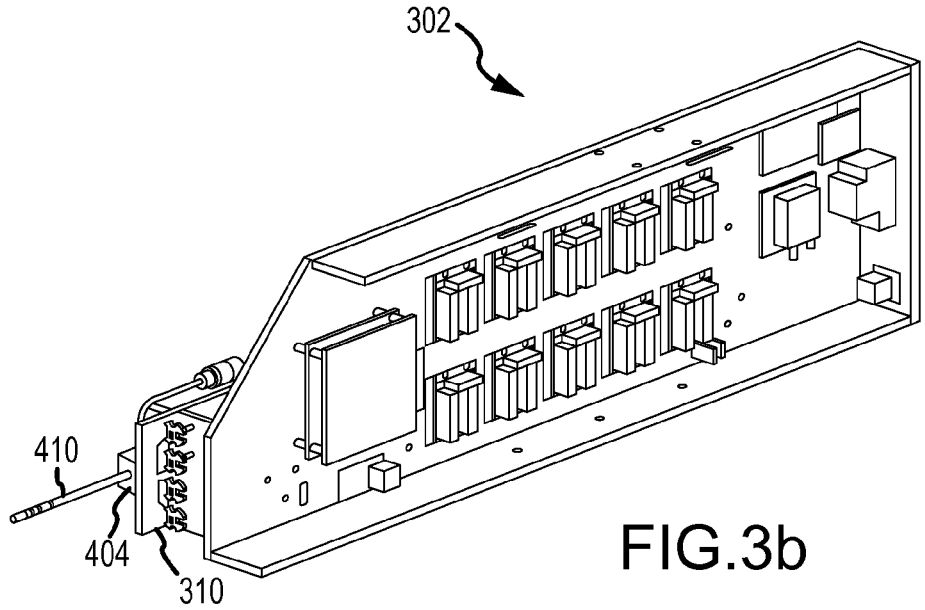

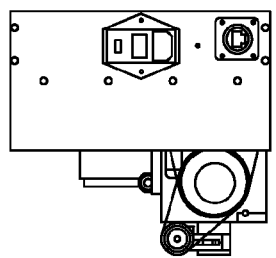
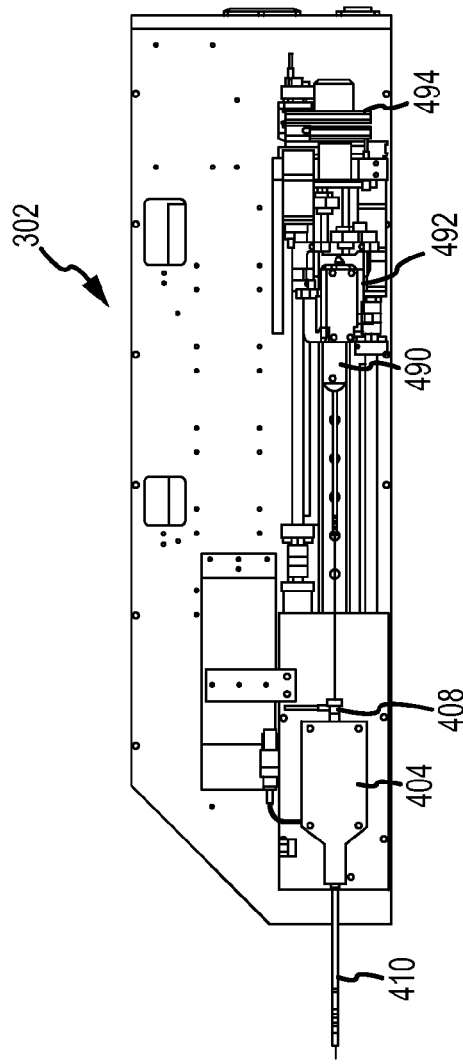
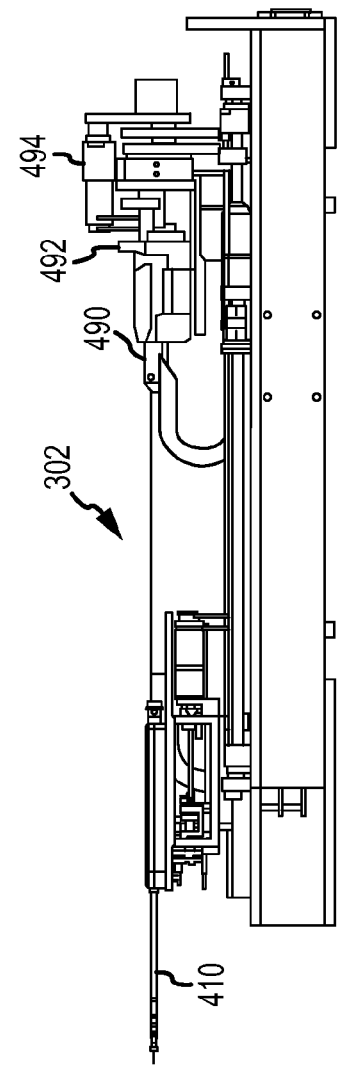
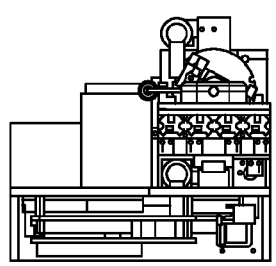
FIG.3o
FIG.3p
FIG.3q
FIG.3n

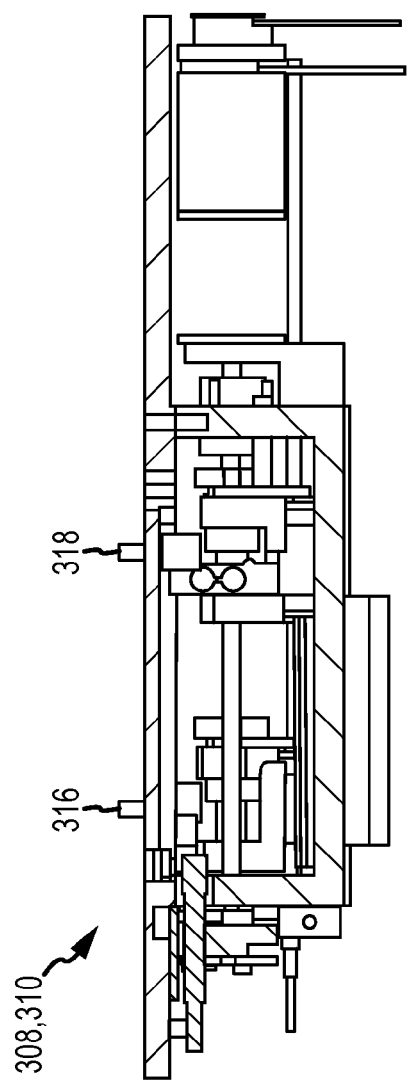
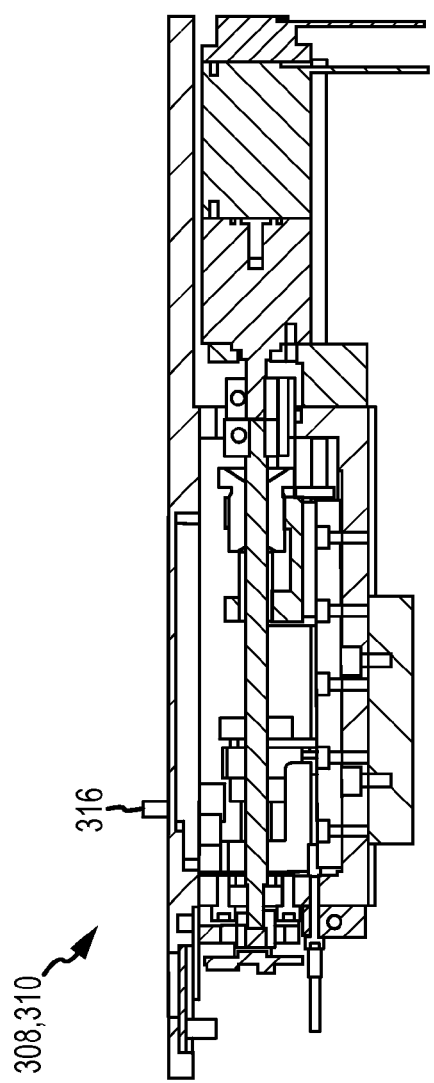
FIG.4f
FIG.4g

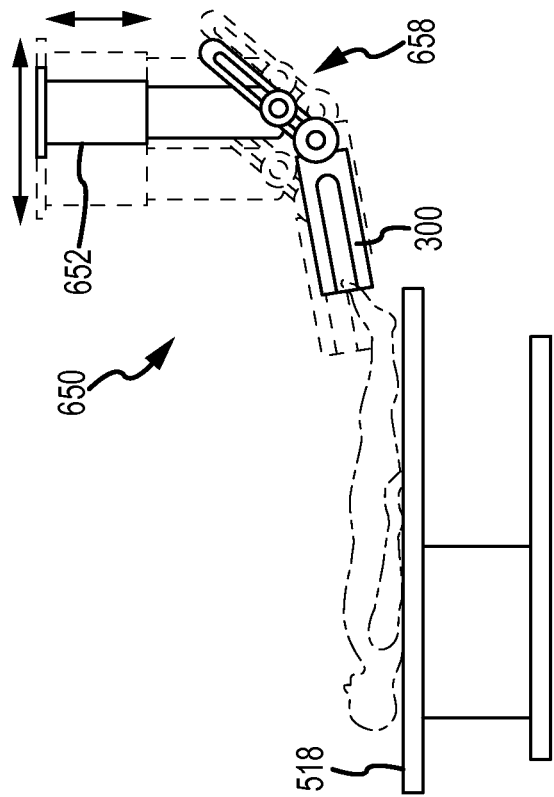
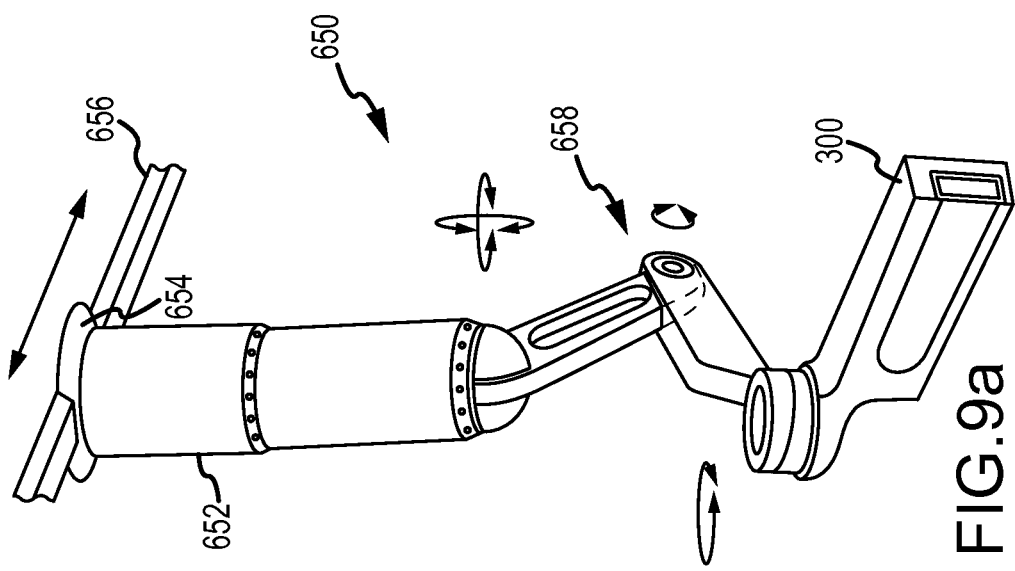
FIG.9b
FIG.9a

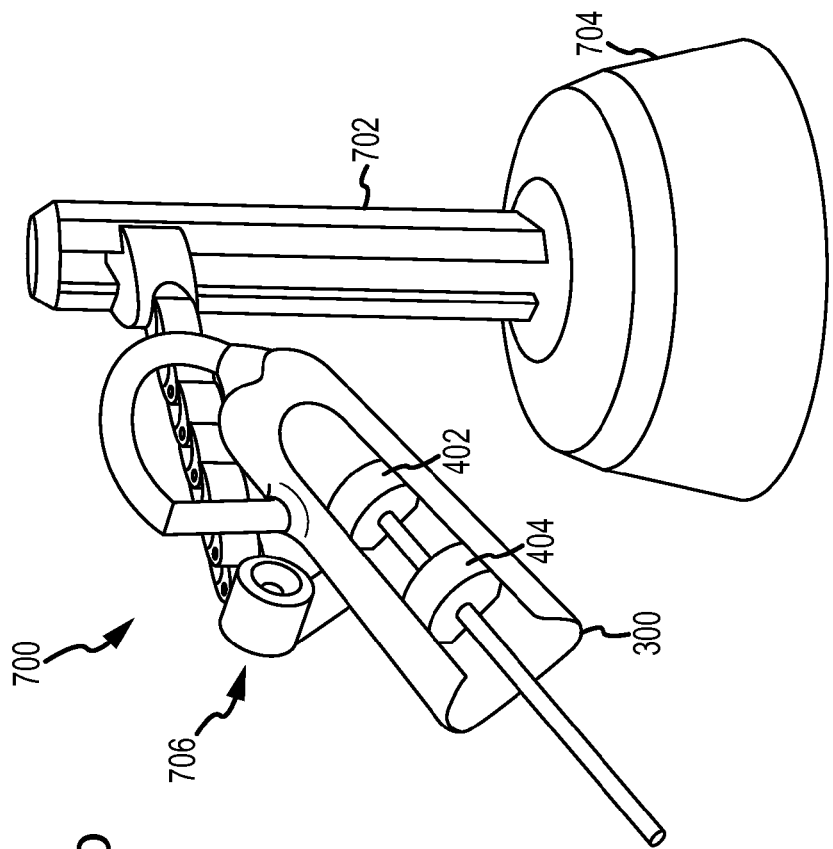
FIG.10a
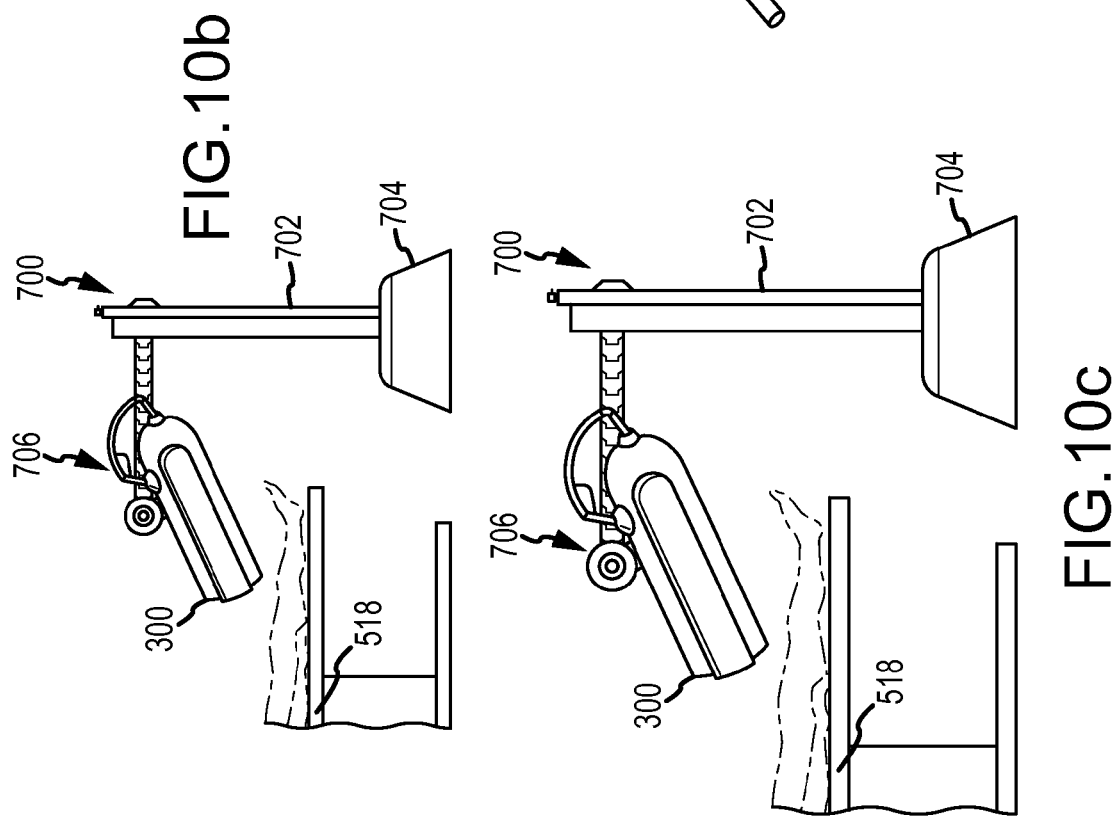
FIG.10b
FIG.10c

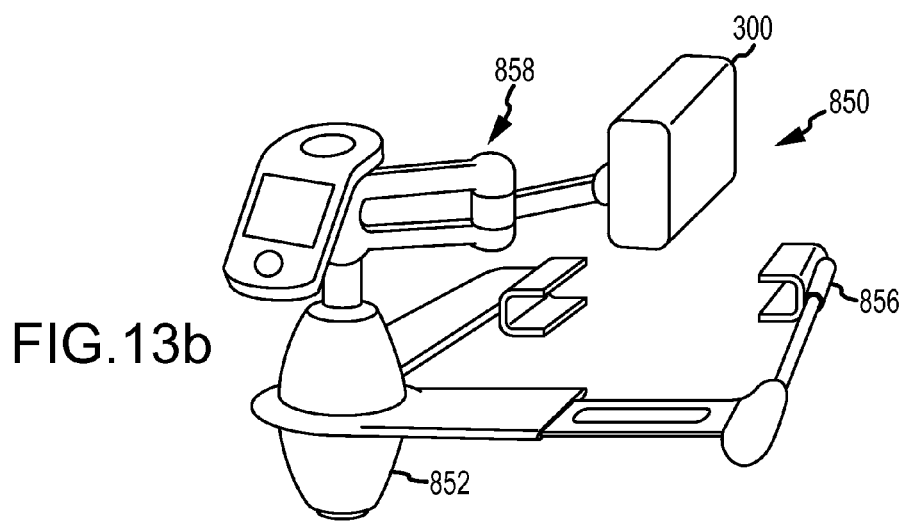
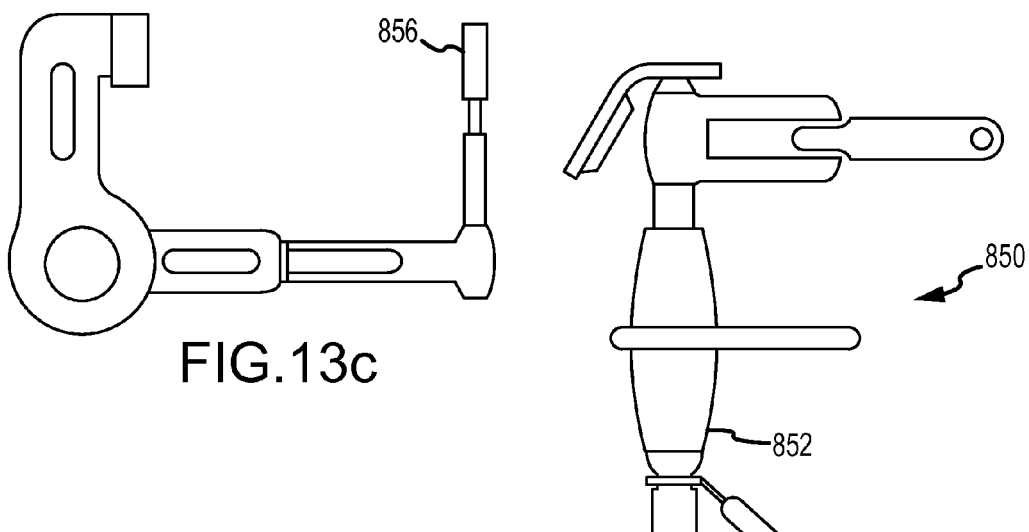
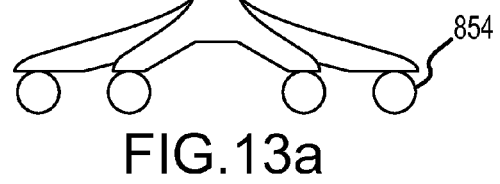
FIG.13b
FIG.13c
FIG.13a

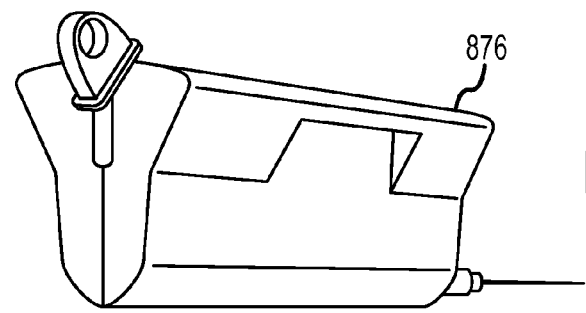
FIG.13j
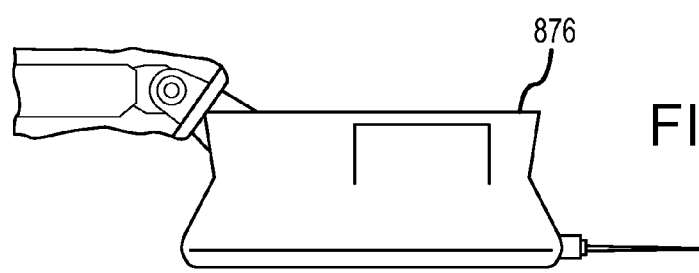
FIG.13k
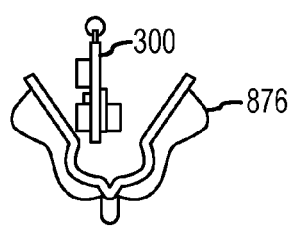
FIG.13n
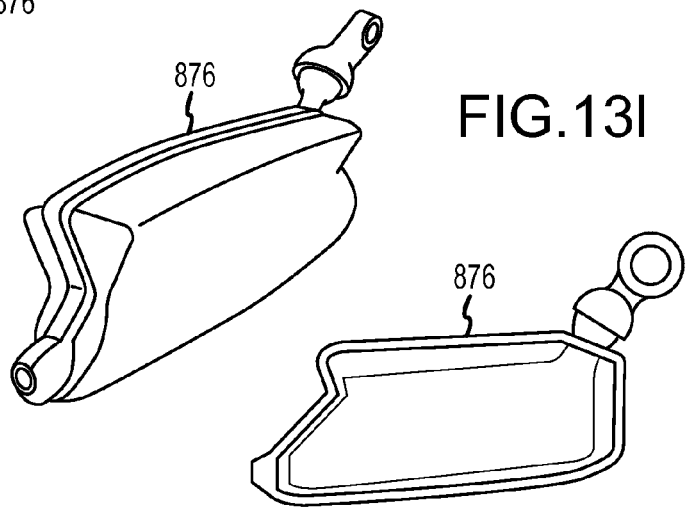
FIG.13l
FIG.13m

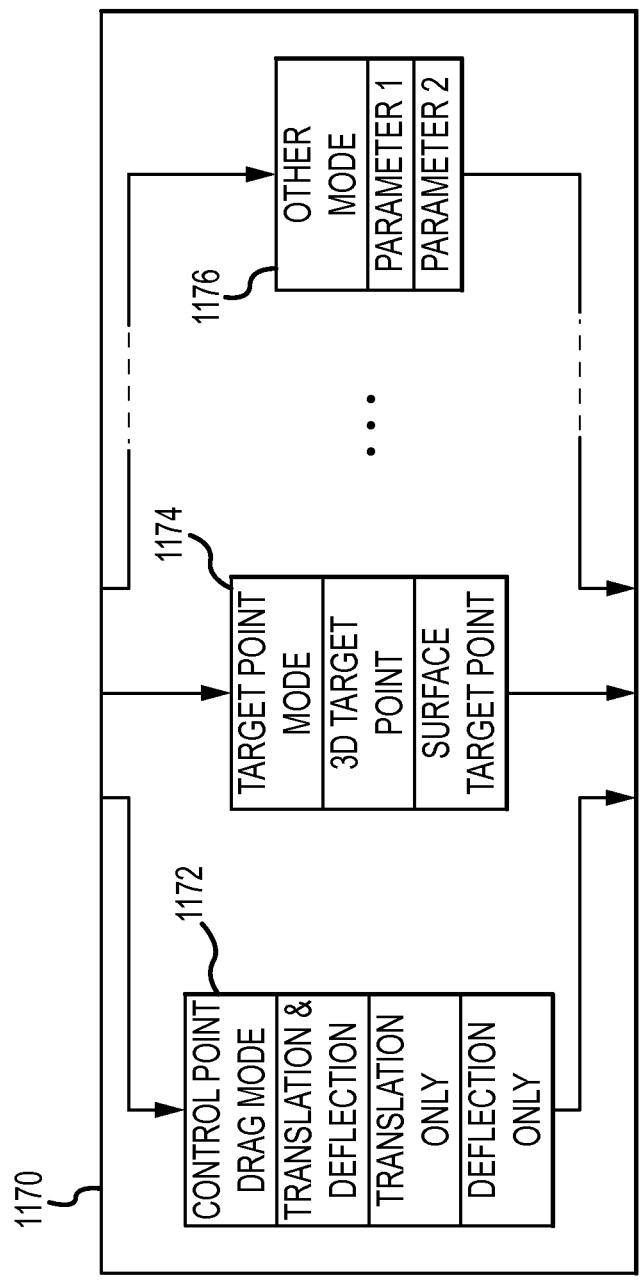

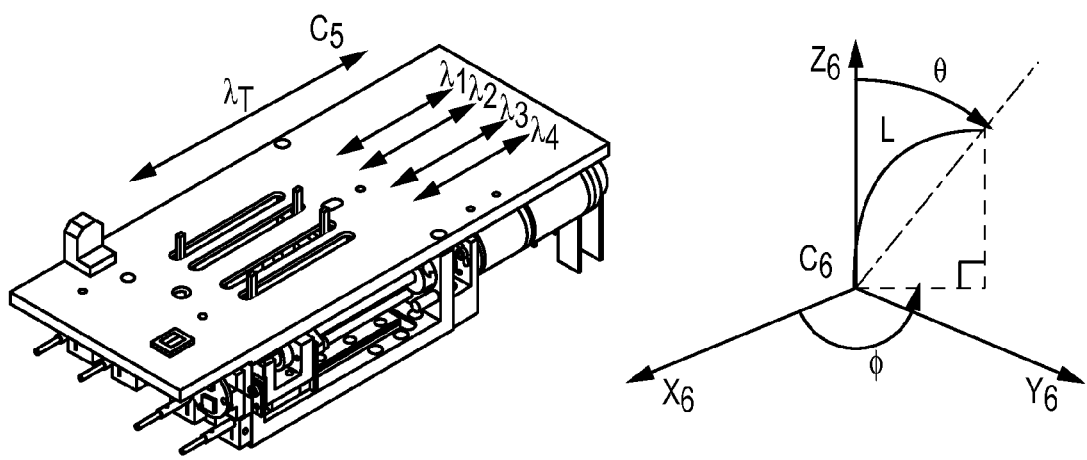
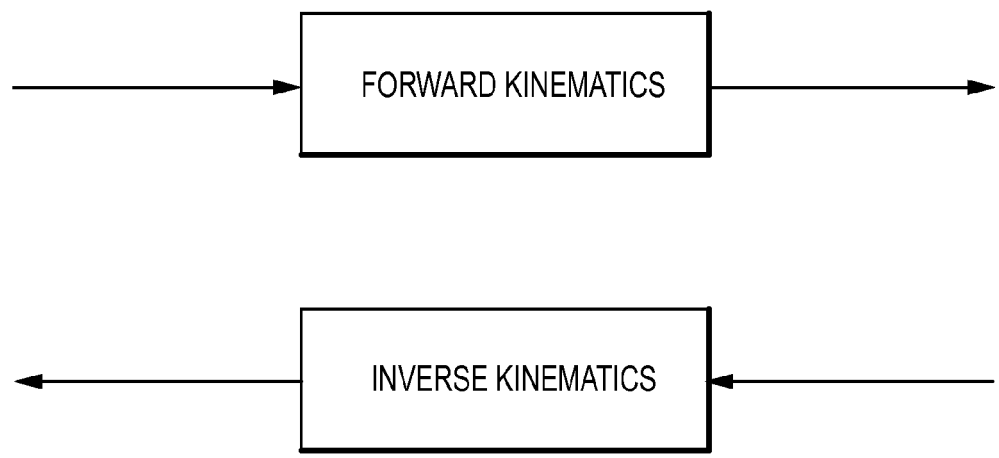
FIG.34

INTUITIVE USER INTERFACE CONTROL FOR REMOTE CATHETER NAVIGATION AND 3D MAPPING AND VISUALIZATION SYSTEMS

CROSS-REFERENCE TO RELATED APPLICATIONS

This application claims the benefit of U.S. provisional application No. 61/319,795, filed 31 Mar. 2010, which is hereby incorporated by reference as though fully set forth herein.

BACKGROUND OF THE INVENTION a. Field of the Invention

This invention relates to a robotic catheter system and method for automated control of a catheter and related components. In particular, the instant invention relates to a robotic catheter system for manipulating a catheter and related components, for example, for diagnostic, therapeutic, mapping and ablative procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrio-ventricular contractions and stasis of blood flow which can lead to a variety of ailments and even death. Typically in a procedure, a catheter is manipulated through a patient's vasculature to, for example, a patient's heart, and carries one or more electrodes which can be used for mapping, ablation, diagnosis, or other treatments. Once at the intended site, treatment can include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level. The inventors herein have thus recognized a need for a system and method for precise and dynamic automated control of a catheter and its related components, for example, for diagnostic, therapeutic, mapping and ablative procedures, that will minimize and/or eliminate procedural variability due to a user's skill level. The inventors herein have also recognized a need for a system and method for performing user-specified procedures at the patient site or from a remote location.

Remote catheter navigation/guidance systems for remote robotic surgical procedures allow physicians to guide multiple catheters placed in the patient's body remotely from the control room/panel. These systems allow the physician to be outside the radiation field of fluoroscopy and perform complex and therefore lengthy EP procedures, such as catheter ablation, while sitting on a chair instead of standing up by the bedside as in a manual operation, thereby reducing physician fatigue. 3D mapping and visualization systems such as EnSite NavX™ from St. Jude Medical, Inc. allow a 3D anatomical map of the cardiac chambers to be created, allowing the physician to visualize the catheters in various cardiac chambers throughout the procedure as well as to map the arrhythmia origins. The user interface for a remote surgical catheter guidance system and 3D mapping and visualization systems typically comprise displays, keyboards, and a (3D) mouse. Such robotic surgical systems also use input devices, which allow the physician to articulate the remote catheter motion. These solutions add to the clutter in the EP labs with numerous instruments requiring multiple keyboards, displays, and mice. Furthermore, such robotic systems attempt to provide intuitive control interfaces with the use of special 3D input devices, which require physician training in how best to manipulate the input device to articulate the desired catheter motion.

BRIEF SUMMARY OF THE INVENTION

The invention relates to a control system for user-guided robotic control of a medical device. The control system is configured to receive input from a touch screen display, such as, for example, a multi-touch display, to allow physicians to manipulate catheters and sheaths with the touch screen display. Using their hands, fingers, or other input device, physicians can interact with the interface to guide a robotically-controlled catheter.

The control system can include an electronic control unit (ECU), a computer-readable memory coupled to the ECU, and a visualization system configured to provide a view of an anatomical model. The system can further include user interface logic stored in the memory configured to be executed by the ECU, and configured to obtain input from a touch screen display with respect to the view of an anatomical model. The system can further include control logic stored in the memory configured to be executed by the ECU and configured to produce an actuation control signal responsive to the input to control actuation of a manipulator assembly so as to move a medical device.

In an embodiment, by interacting with a touch screen display integrated with the control system and coupled with the user interface logic, a user can, for example:

choose menu options;
change the view orientation of an anatomical model, such as a 3D geometry or map of one or more cardiac chambers created by a visualization and navigation system or a 3D geometry or map of one or more cardiac chambers from an imaging system such as CT or MRI;
change the magnification of the above described objects;
change all other attributes of the above described objects such as color, screen location, etc.;
place lesion markers or automated motion targets on the 3D objects described above;
rotate the 3D objects described above; and
select catheter(s) and/or sheath(s) for remote navigation/guidance.

In an exemplary system and procedure, a physician can select a catheter by tapping on an image of the catheter on the display and/or virtually "pick up" the catheter tip with a pinching motion detectable by the touch screen display. The physician can then move the catheter on the display to a desired location by dragging the image of the catheter across the display. A controller and bedside system can then guide the catheter to the actual location in the heart chamber represented by the desired location on the display. The system can also include a variety of safety mechanisms for avoiding unintended touch-based inputs or unintended movements of the catheter. Furthermore, the physician can move multiple items on the touch screen display. For example, a 3D map or model can be selected and the physician can zoom in on the model or a particular portion of the model by using hand motions suitable for the touch screen display to interpret. Other display elements such as fluoroscopic images, intracardiac echocardiography (ICE) images, electrophysiology (EP) recorder images, and vital signs can also be arranged on the desired display and interacted with by the user.

BRIEF DESCRIPTION OF THE DRAWINGS

FIG. 1 is an isometric diagrammatic view of a robotic catheter system, illustrating an exemplary layout of various system components.

FIGS. 3a-3c are enlarged isometric, FIGS. 3n-3q are respectively enlarged left side, right side, top and front views of the robotic catheter manipulator assembly of FIG. 3a, illustrating use of the manipulator assembly with a robotic catheter rotatable device cartridge.

FIGS. 4d-4g are respectively enlarged top and right side, and respectively sections A-A and B-B taken generally along lines A-A and B-B in FIG. 4d, of a first embodiment of a manipulation base.

FIGS. 9a and 9b are isometric and related diagrammatic views of a fourth embodiment of a robotic catheter manipulator support structure.

FIGS. 10a-10c are isometric and related diagrammatic views of a fifth embodiment of a robotic catheter manipulator support structure.

FIG. 19e-g are various diagrammatic views of a control system for a robotic catheter system that can use a touch-sensitive input device.

FIG. 34 is an illustration of forward and inverse kinematic relationships.

DETAILED DESCRIPTION OF EMBODIMENTS OF THE INVENTION

Figure 2A:
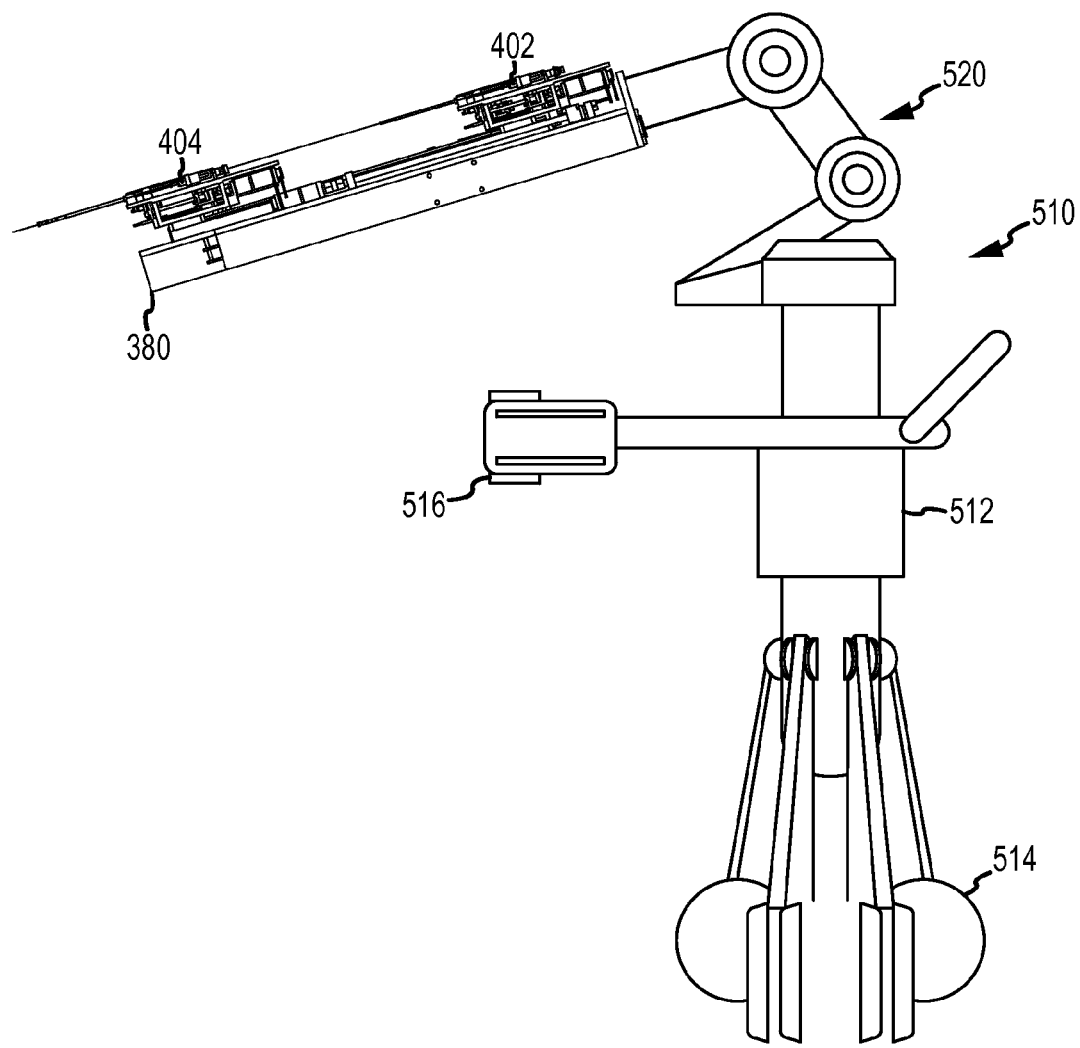
FIGS. 2a-2c are isometric and related diagrammatic views of a first embodiment of a robotic catheter manipulator support structure, with FIG. 2a illustrating a robotic catheter manipulator slightly angled from a generally horizontal position.
Figure 2B:
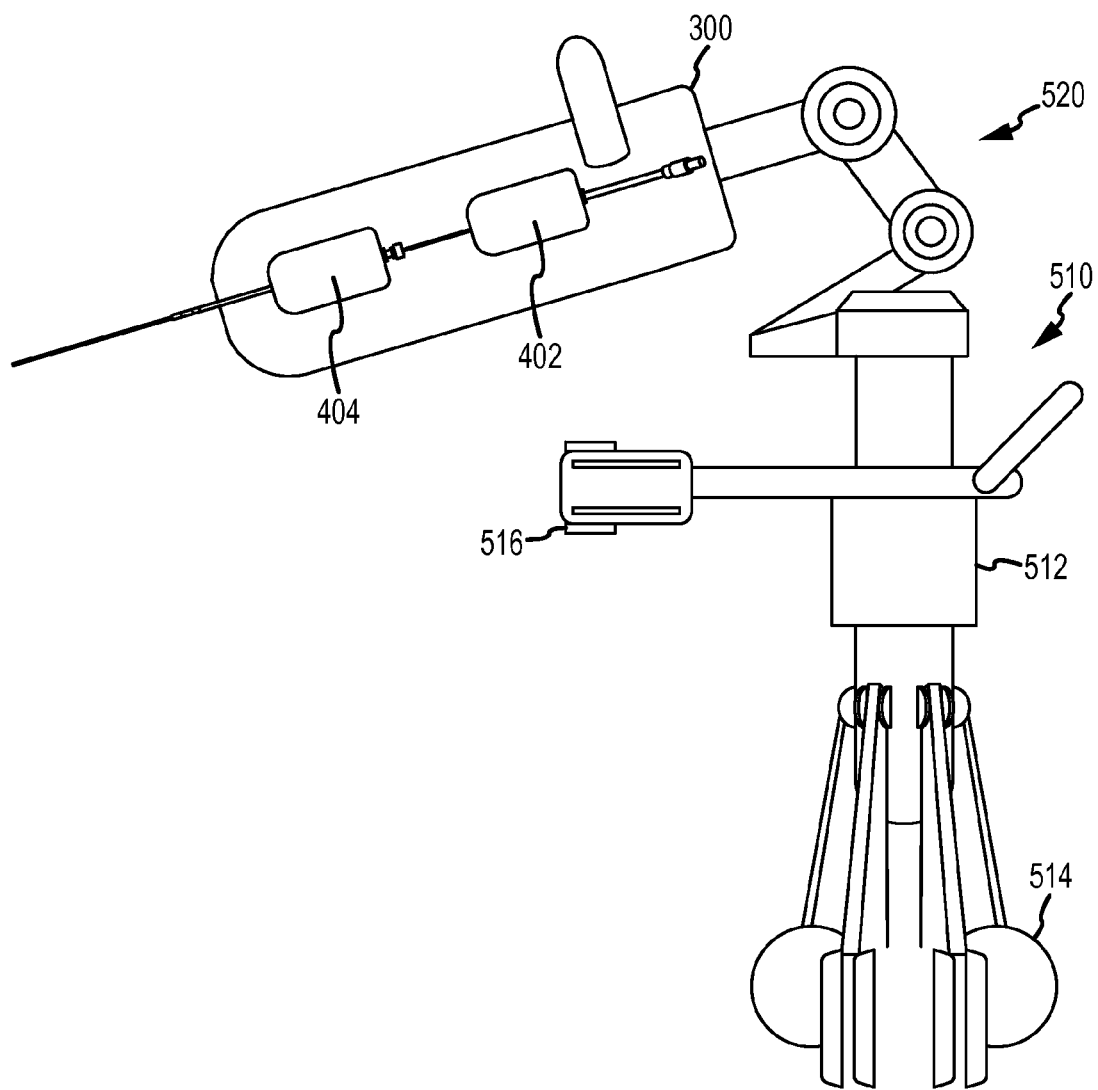
Figure 2C:
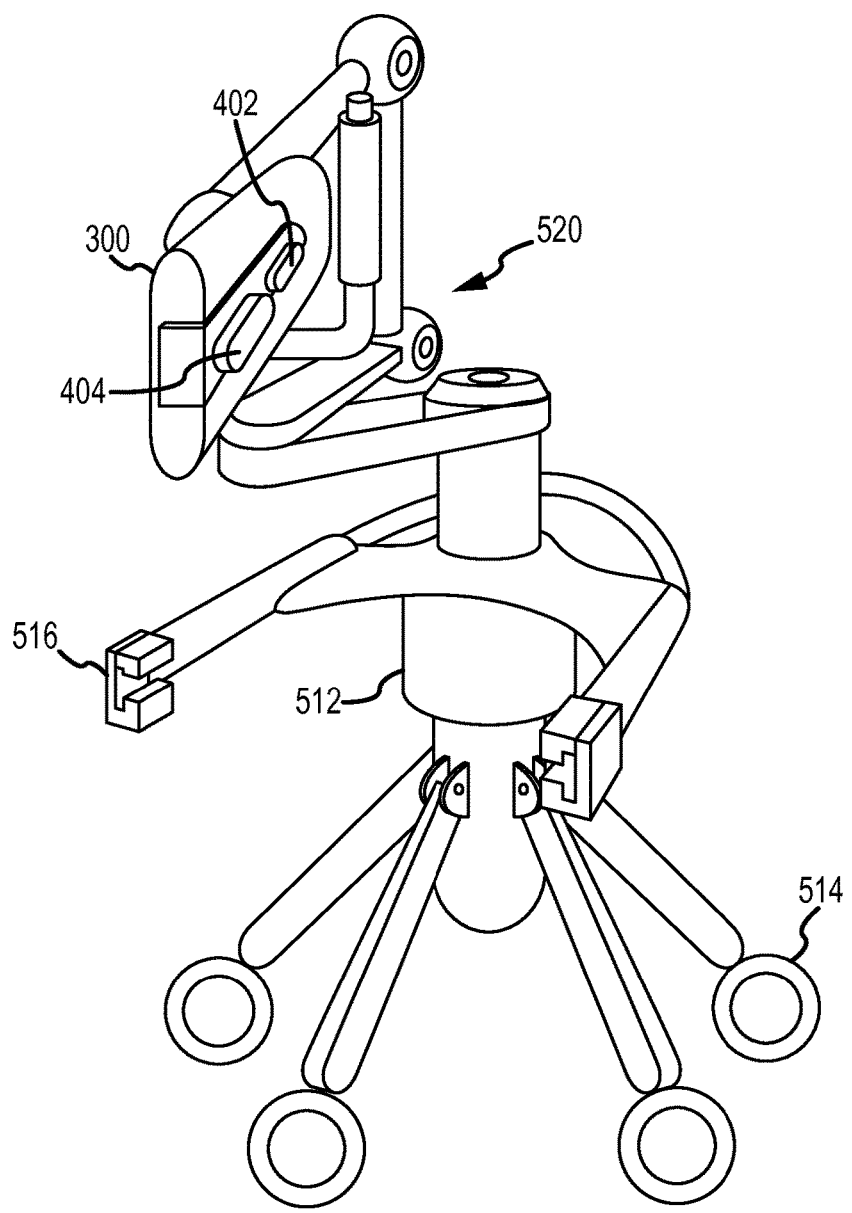

Referring now to the drawings wherein like reference numerals are used to identify identical components in the various views, an embodiment of robotic catheter guidance system 10 ("RCGS") (described in detail below), also referred to as "the system," can be likened to power steering for a catheter system. The system can be used, for example, to manipulate the location and orientation of catheters and sheaths in a heart chamber or in another body cavity. As shown in FIG. 1 and described in detail below, robotic catheter system 10 can generally incorporate a human input device and control system (referred to as "input control system") 100, e.g., a joystick and related controls that a user such as an electrophysiologist (EP) can interact with, an electronic control system 200 that translates motions of the user at the input device into a resulting movement of a catheter tip, and a visualization system 12 that provides a user with real-time or near-real-time positioning information concerning the catheter tip. The system can further include closed-loop feedback using an EnSite NavX system 14, or similar positioning systems such as, for example, the gMPS system, commercially available from Mediguide Ltd., a robotic catheter manipulator assembly 300 for operating a robotic catheter device cartridge 400 and manipulator support structure 500 (described in detail below). The system provides the user with a similar type of control provided by a conventional manual system, but allows for repeatable, precise, and dynamic movements. The respective disclosures of the above-identified and other commonly owned and copending applications discussed in this application are incorporated herein by reference.

An embodiment of robotic catheter system 10 can involve automated catheter movement. A user, such as an EP, could identify locations (potentially forming a path) on a rendered computer model of the cardiac anatomy. The system can be configured to relate those digitally selected points to positions within a patient's actual/physical anatomy, and can command and control the movement of a catheter to defined positions. Once in position, either the user or system could then perform the desired treatment or therapy—which can further be in accordance with a defined algorithm. The system can enable full robotic control by using optimized path planning routines together with closed-loop position control. Furthermore, the system can automate certain "best-practices," such as pulling the catheter across the surface, or making contact at an oblique angle.

Referring to FIG. 1, input control system 100 will be described briefly.

The input control system 100 can generally allow a user to control the movement and advancement of both the catheter and sheath. Generally, several types of input devices can be employed, including, without limitation, instrumented traditional catheter handle controls, oversized catheter models, instrumented user-wearable gloves, touch screen display monitors, two-dimensional (2D) input devices, three-dimensional (3D) input devices, spatially detected styluses, and traditional joysticks. The input device can be configured to directly control the movement of the catheter and sheath, or can be configured to, for example, manipulate a target or cursor on an associated display. In embodiments, for example and without limitation, the joystick can be spring centering so that any movement from the center position causes an incremental movement of the actual catheter tip, or the joystick can work in absolute terms. Haptic feedback can also be incorporated to provide a user with a sense of when contact has been made.

Referring to FIG. 1, electronic control system 200 will be described briefly.

As discussed in detail in commonly owned and copending applications titled "Robotic Catheter System Input Device," filed 29 Dec. 2009 as international patent application no. PCT/US2009/069712 and "Robotic Catheter System with Dynamic Response," filed as international patent application no. PCT/US2009/038,597, many features can be included with embodiments of the system to, for example, improve the accuracy or effectiveness of the system. Such features can include, closed-loop feedback using an EnSite NavX system or gMPS system 14 for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

Referring to FIG. 1, visualization system 12 will be described briefly.

Visualization system 12 can provide a user with real-time or near-real-time positioning information concerning the catheter tip. In an exemplary embodiment, system 12 can include an EnSite NavX monitor 16 or other similar monitor for displaying cardiac chamber geometries or models, displaying activation timing and voltage data to identify arrhythmias, and for facilitating guidance of catheter movement. A fluoroscopy monitor 18 can be provided for displaying a real-time x-ray image or for assisting a physician with catheter movement. Additional exemplary displays can include an ICE and EP Pruka displays, 20, 22, respectively.

Referring to FIG. 1, EnSite NavX™ system 14 will be described briefly.

EnSite NavX™ system 14 (described in detail in U.S. Pat. No. 7,263,397, titled "Method and Apparatus for Catheter Navigation and Location and Mapping in the Heart," incorporated by reference in its entirety) can be provided for creating realistic cardiac chamber geometries or models, displaying activation timing and voltage data to identify arrhythmias, and guiding precise catheter movement. EnSite NavX™ system 14 can collect electrical position data from catheters and use this information to track or navigate their movement and construct 3D models of the chamber.

In an embodiment, position data from the catheter can be obtained using a gMPS system, commercially available from Mediguide Ltd., and generally shown and described in U.S. Pat. No. 7,386,339 entitled "Medical Imaging and Navigation System," which is incorporated herein by reference in its entirety.

Referring to FIGS. 1-6c, robotic catheter manipulator assembly 300 for operating robotic catheter device cartridges 400 will be described briefly.

As generally shown in FIGS. 1-6c, robotic catheter system 10 can include one or more robotic catheter manipulator assemblies 300 that serve as the mechanical control for the movements or actions of one or more robotic catheter device cartridges 400. FIG. 1 illustrates a generally vertically oriented manipulator assembly 300 for minimizing approach angle; FIG. 2a illustrates a manipulator assembly 380 slightly angled from a generally horizontal position; and FIG. 2d illustrates an embodiment where multiple manipulator assemblies can be used for a single procedure. FIGS. 3a and 6a-6c respectively illustrate first—fourth embodiments of assemblies 300, namely assemblies 302, 370, 372 and 374. Manipulator assembly 302 and its associated components will be described herein for facilitating an understanding of robotic catheter system 10.

Referring to FIGS. 1 and 3a-5e, the catheter and sheath configuration of robotic catheter manipulator assembly 300 and robotic catheter device cartridges 400 will be described in detail.

As generally shown in FIGS. 1 and 3a-5e and discussed in greater detail below, the first embodiment of manipulator assembly 302 can respectively include both catheter and sheath manipulator mechanisms 304, 306. In this arrangement, the catheter and sheath manipulator mechanisms 304, 306 can be aligned such that the catheter can pass through the sheath in a coaxial arrangement. Each mechanism 304, 306 can be further capable of independent advancement/retraction (shown generally as directions $D_1$ and $D_2$) and independent four-wire steering control (e.g., eight total steering wires, comprising four sheath control wires and four catheter control wires), as discussed in detail below. It should also be understood that, while both the catheter and sheath can be capable of independent control, in alternative embodiments the system can only provide for control of one device while allowing the other device to remain passive (e.g., the sheath is actively controlled while the catheter is passive or "along for the ride"). In a configuration where one passive device is used, it cannot be necessary to include control wires in the passive device.

With a configuration of robotic catheter system 10, such as shown in FIGS. 1 and 3a-5e, there will be relative travel of a first embodiment of catheter and sheath cartridges 402, 404 and relative movement associated with a portion of a catheter 406 between the two cartridges 402, 404. For many embodiments, there can be a water-tight fit of a proximal sheath opening 408, which can sometimes create resistance to catheter advancement. In order to help eliminate/reduce the potential issue of columnar buckling of catheter 406, a length of stiff material, such as, for example, a solid metal rod or fiber reinforced composite, can be incorporated on the interior of the proximal portion of catheter 406. Such a material can locally increase the catheter's bending stiffness and provide enhanced buckling support. Thus catheter 406 can be proximally stiffened so that the length of the catheter proximally extending from sheath cartridge 404 is less likely to buckle during relative translation, as the entire length of catheter 406 extends into sheath 410.

Referring to FIGS. 1 and 3a-5e, the first embodiment of robotic catheter manipulator assembly 302 will be described in detail.

As generally shown in FIGS. 1 and 3a-5e, robotic catheter system 10 which includes one or more robotic catheter manipulator assemblies 300, includes the first embodiment of robotic catheter manipulator assembly 302 including both catheter and sheath manipulation mechanisms 304, 306 for manipulating, for example, catheter and sheath cartridges 402, 404. Manipulator assembly 302 can include interconnected/interlocking manipulation bases 308, 310 for catheter and sheath cartridges 402, 404, and likewise can include electrical "handshake" functionality as discussed below. Each interlocking base 308, 310 can be capable of travel in the longitudinal direction of the catheter/sheath ($D_1$, $D_2$ respectively). In an embodiment, $D_1$ and $D_2$ can each represent a translation of approximately 8 linear inches. As shown in FIG. 3a, each interlocking base can be translated by high precision drive mechanisms 312, 314. Such drive mechanisms can include, for example and without limitation, a motor driven lead screw or ball screw.

Figure 4A:
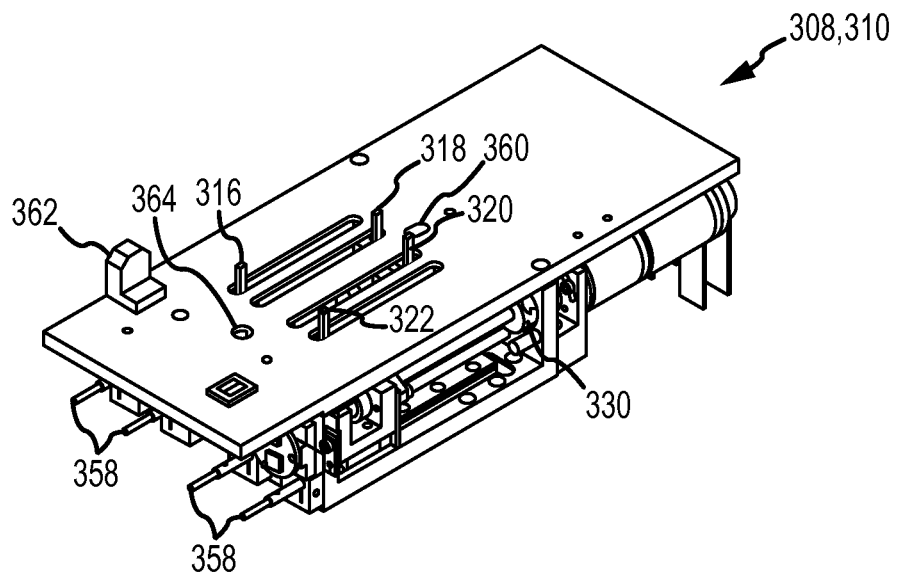
FIGS. 4a-4c are enlarged isometric views.
Figure 4B:
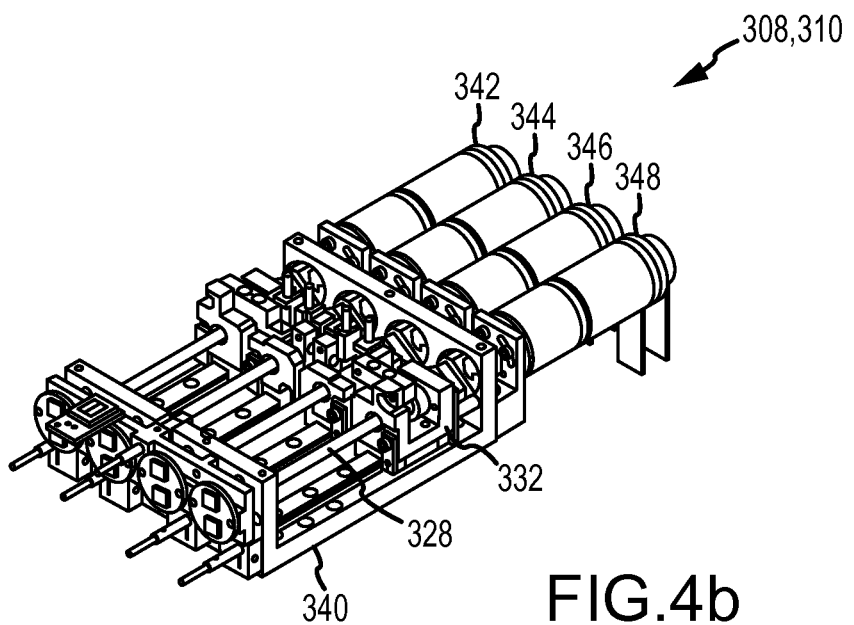
Figure 4C:
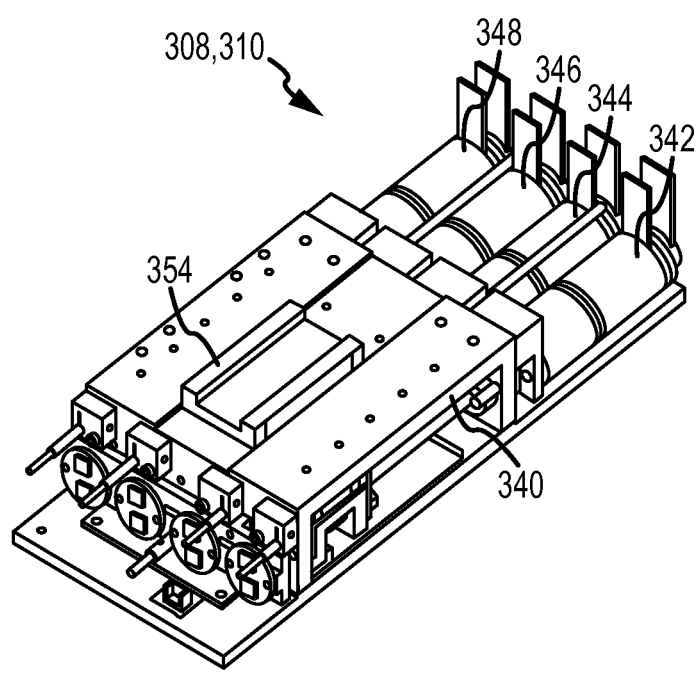
Figure 4D:
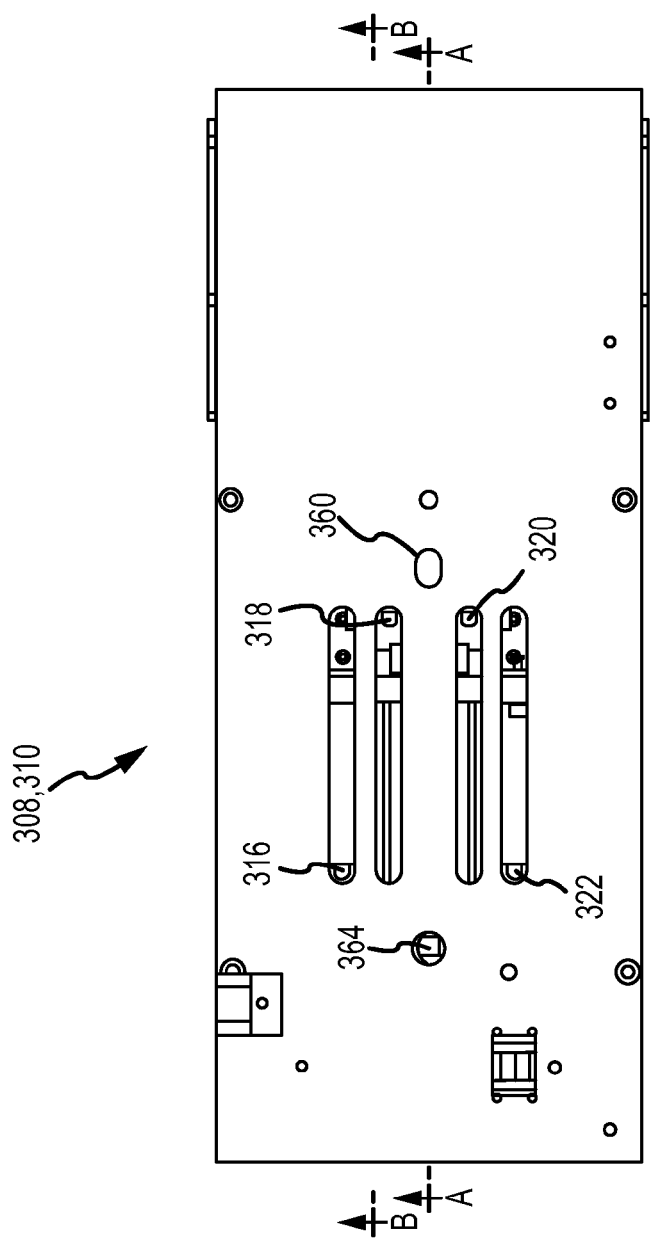
Figure 4E:
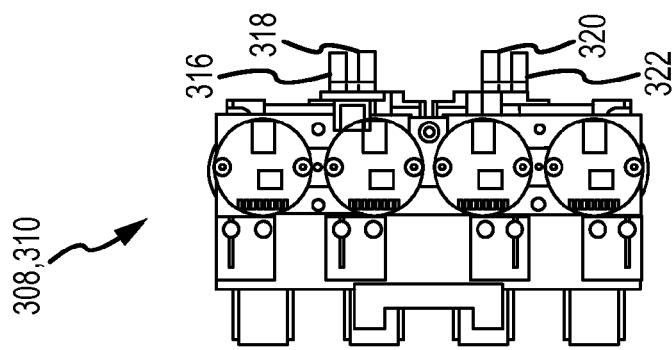

As shown in FIGS. 3a-3i and 4a-4g, for each cartridge 402, 404, an associated manipulation base 308, 310 can include a plurality of fingers 316, 318, 320 and 322, (e.g., one per steering wire) that extend or protrude upwardly to contact and interact with the steering wire slider blocks (such as slider blocks 412, 414, 416, 418) to independently tension select steering wires 420, 422, 424, 426. Each finger can be configured to be independently actuated by a precision drive mechanism, such as a motor driven ball screw 324, and can be outfitted with steering wire force sensors to measure corresponding steering wire tension. Each motor driven ball screw (for both finger control and cartridge translation control) can further include encoders to measure a relative and/or an absolute position of each element of the system. As shown in FIG. 4a, bearing 332 and coupler 330 of ball screw 324 can engage frame 340 of respective bases 308, 310 and a corresponding finger 316, 318, 320 or 322 can be mounted adjacent a strain gauge for measuring the corresponding steering wire tension.

Referring to FIGS. 4a-4g, bases 308, 310 can include exemplary components such as motors 342, 344, 346 and 348, respectively coupled to fingers 316, 318, 320 and 322. A bearing 354 can be provided for sliding of bases 308, 310 on track 356. A plurality of inductive sensors (e.g. home sensors) 358 can be provided for guiding each manipulation base to a safe position.

Manipulator assembly 302 can be disposed in a vertical configuration (see FIG. 1) for minimizing both the approach angle of the catheter and the distance the catheter could extend from the patient, or slightly angled from a generally horizontal position (see FIG. 2). In the vertical configuration of FIG. 1, the approach angle and catheter extension distance can be minimized by vertically orienting the backplane of the manipulator head, with the interlocking cartridges positioned at the lower extreme such that they can travel nearly horizontally and substantially in line with the point of entry into the patient (e.g., as generally illustrated in FIG. 1). In such an embodiment, with the backplane of the manipulator head vertically oriented, the positioning of the manipulator head structure can allow the proximal control of the catheter/sheath to be held closely to the patient's body without substantial structural interference. In an embodiment, high-precision drive mechanisms 312, 314 for translating each of the catheter and sheath cartridges 402, 404 can be positioned generally below the manipulator bases 308, 310 to allow the respective cartridges to be positioned toward the lower area of the manipulator. By holding a close distance, the ingress angle of the catheter/sheath can be minimized, and the manipulator control can be positioned more closely to an insertion site.

Figure 3C:
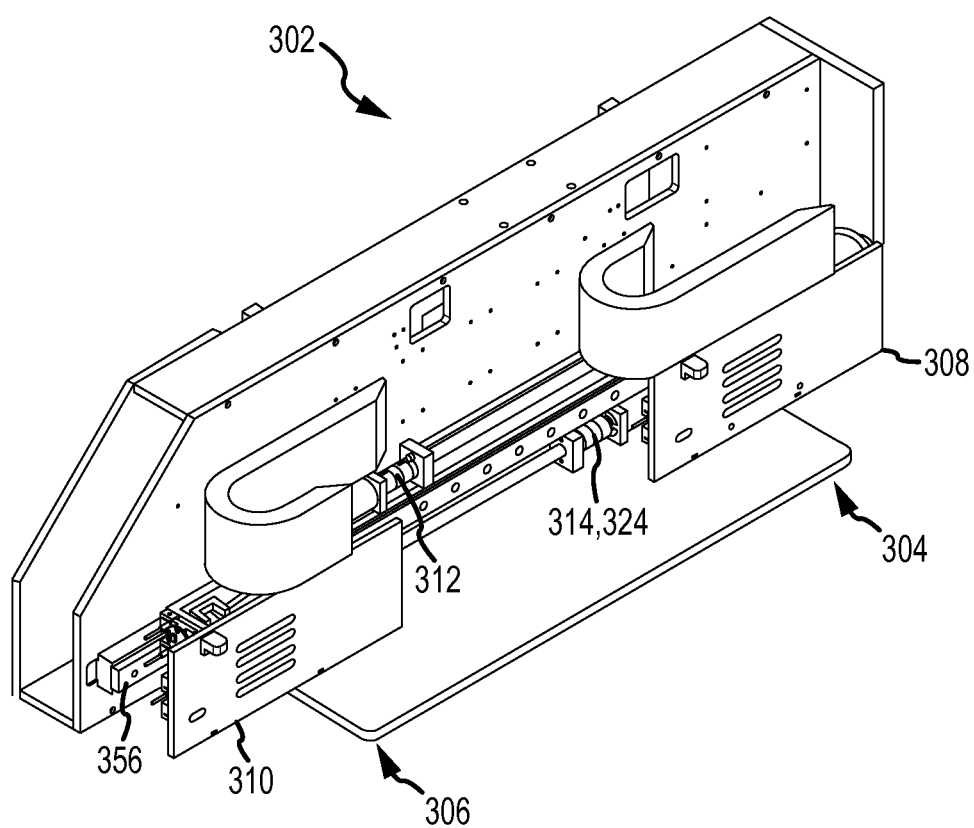
Figure 3E:
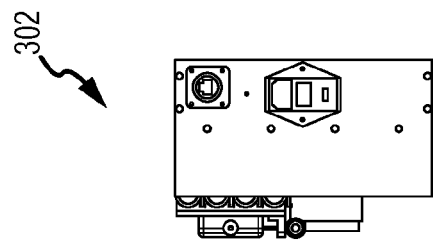
FIGS. 3d-3i are respectively enlarged left side, right side, top, front, back and a corresponding left side view of a first embodiment of a robotic catheter manipulator assembly.
Figure 3F:
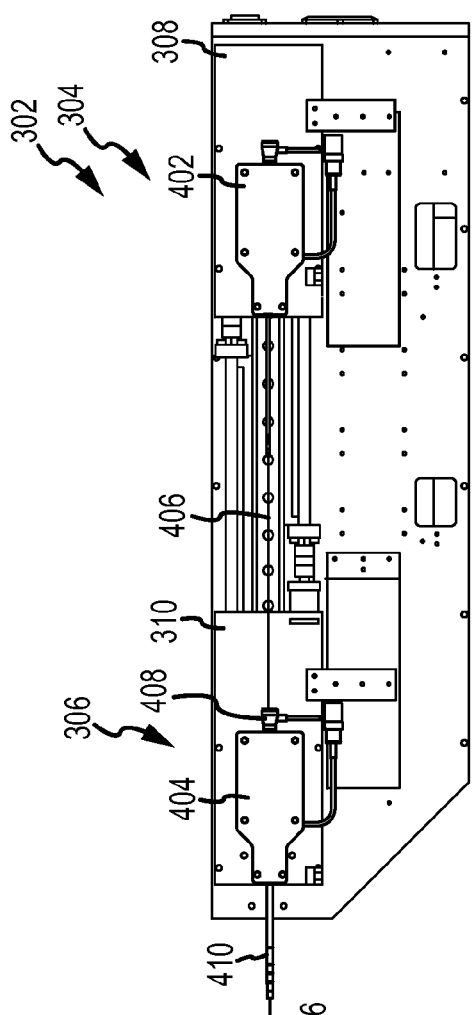
Figure 3D:
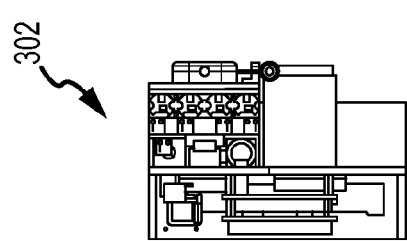
Figure 3G:
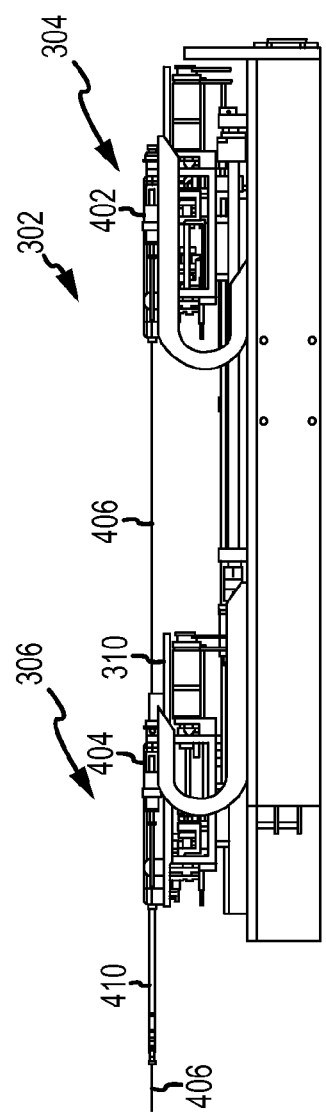
Figure 3H:
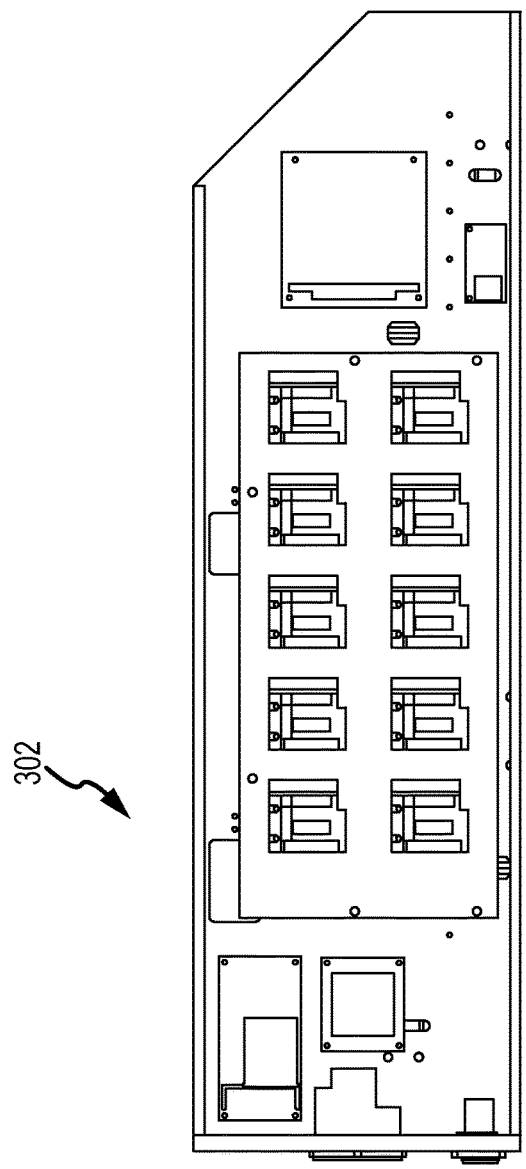
Figure 3I:
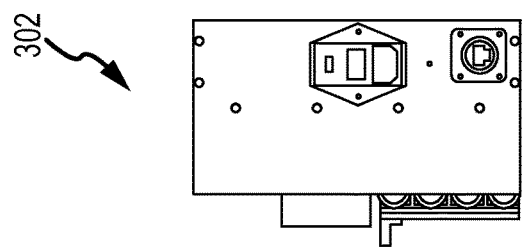
Figure 3J:
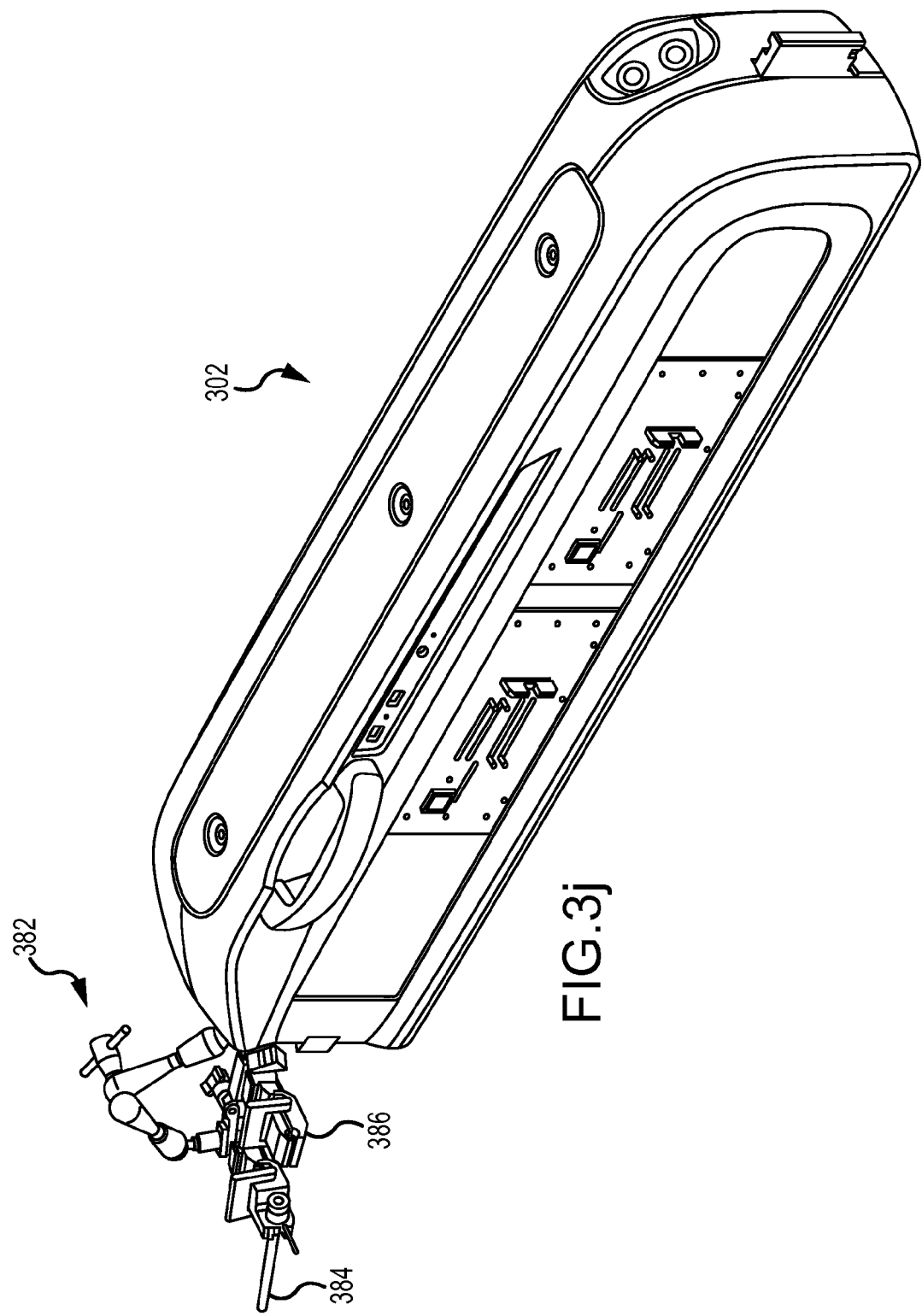
FIG. 3j is a catheter manipulator assembly including a support device.
Figure 3K:
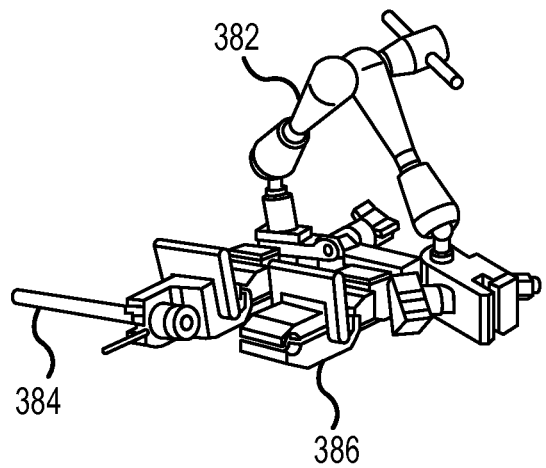
FIGS. 3k-3m illustrate embodiments of a support device.
Figure 3L:
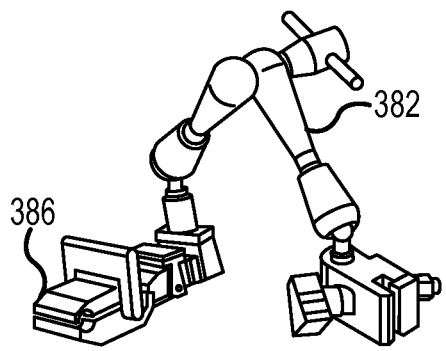
Figure 3M:
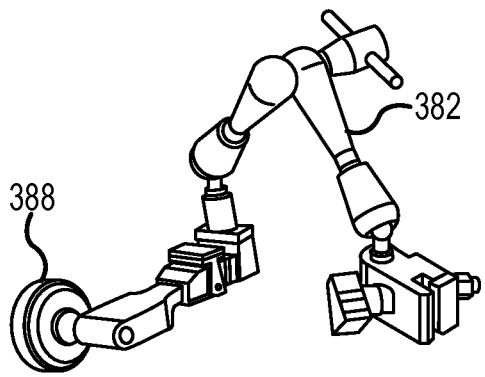

Referring to FIG. 3j, manipulator assembly 302 can include a support device 382 positioned on the distal end of the manipulator assembly and configured to receive one or more ancillary tools, such as, for example, an introducer 384, a guide 386, or a hemostasis pad 388. Various configurations of support devices and ancillary tools are illustrated in FIGS. 3k-3m. In an embodiment the support device 382 and ancillary tools, are configured to interact with a portion of the catheter and/or sheath between the manipulator and the patient. For example, as generally illustrated in FIG.

3*j*-3*l*, introducer 384 and/or guide tube 386 can direct the catheter into the patient at a fixed angle or position while allowing the manipulator to be oriented at a different relative angle. In an embodiment, as generally illustrated in FIG. 3*m*, the support device 382 can include a hemostasis pad 388.

Referring to FIGS. 1-3*q*, particularly FIGS. 3*n*-3*q*, robotic catheter manipulator assembly 302 can be usable with a robotic catheter rotatable device cartridge 490. As shown in FIG. 3*q*, manipulator base 308 can be replaced with a robotic catheter rotatable drive head 492 and a robotic catheter rotatable drive mechanism 494.

Referring to FIGS. 1 and 5*a*-5*e*, catheter and sheath cartridges 402, 404 will be described in detail.

As briefly discussed above, robotic catheter system 10 can include one or more cartridges 400, with manipulator 302 including at least two cartridges 402, 404, each of which can be respectively designed to control the distal movement of either the catheter or the sheath. With respect to catheter cartridge 402, catheter 406 can be substantially connected or affixed to cartridge 402, so that advancement of cartridge 402 correspondingly advances catheter 406, and retraction of the cartridge retracts the catheter. As further shown in FIGS. 5*a*-5*e* and discussed above, in an embodiment, each cartridge 402, 404 can include slider blocks (e.g., 412, 414, 416, 418), each rigidly (and independently) connected or affixed to one of a plurality of catheter steering wires (e.g., 420, 422, 424, 426) in a manner that permits independent tensioning of each steering wire. The cartridge can be provided as a disposable item that is capable of being easily positioned (e.g., snapped) into place in an overall assembly. In an embodiment, as discussed in detail below, the cartridge can include an electrical "handshake" device or component to allow the system to properly identify the cartridge (e.g., by type and/or proper placement/positioning). Sheath cartridge 404 can be designed in a similar manner as the catheter cartridge 402, but will typically be configured to provide for the passage of catheter 406. Assembly 302 can include a plurality (e.g., as many as ten or more) of independent driving mechanisms (e.g. motor driven ball screws 324).

For some embodiments, the catheter and sheath cartridge can be designed to be substantially similar, and in that context a reference to either can relate to both. For example, as shown in FIGS. 5*a*-5*e*, the design of the catheter/sheath cartridge can include upper and lower cartridge sections 428, 430, and independent slider blocks 412, 414, 416, 418. The system is not generally limited to specific material selection or formation techniques. However, in an embodiment, the upper and lower cartridge sections 428, 430 can be injection molded using a polycarbonate material. Each slider block 412, 414, 416, 418 can be connected to a separate catheter steering wire 420, 422, 424, 426, and can be formed of a Teflon-like material such as, for example, Delrin AF. When in contact with the cartridge housing portions 428, 430, such Teflon-like slider blocks can maintain a low static and dynamic coefficient of friction and can avoid the need for additional lubrication.

Figure 5A:
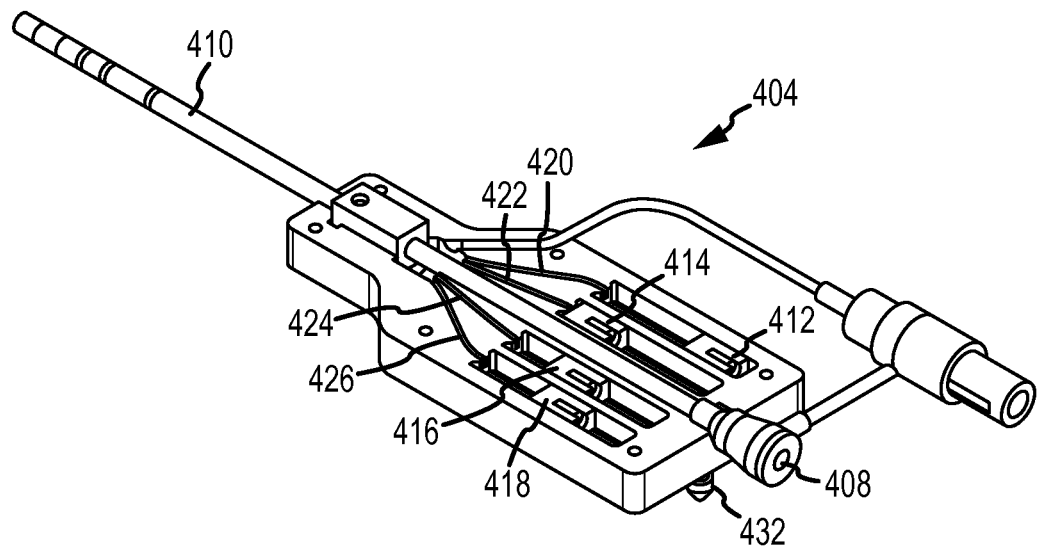
FIGS. 5a-5e are enlarged isometric views of a first embodiment of a robotic catheter device cartridge, with FIG. 3a illustrating an exemplary usage of the robotic catheter device cartridge.
Figure 5B:
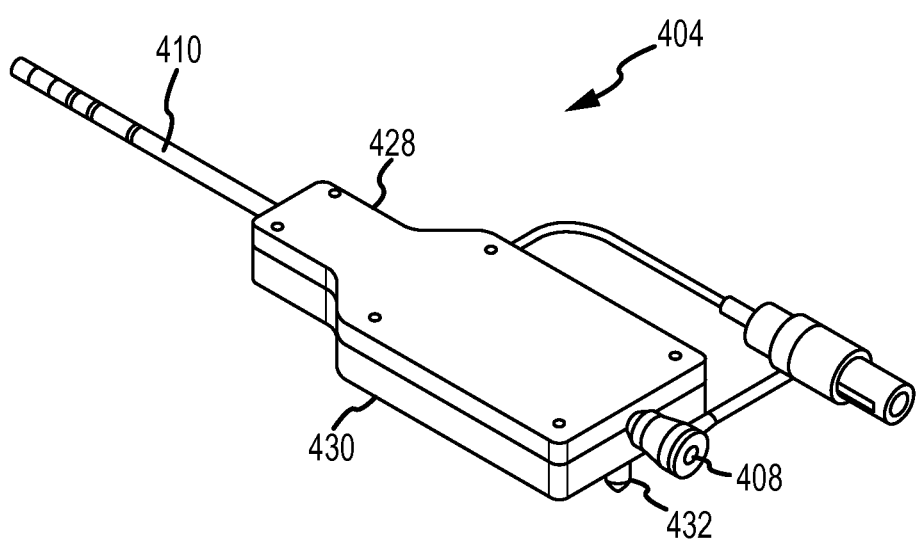
Figure 5C:
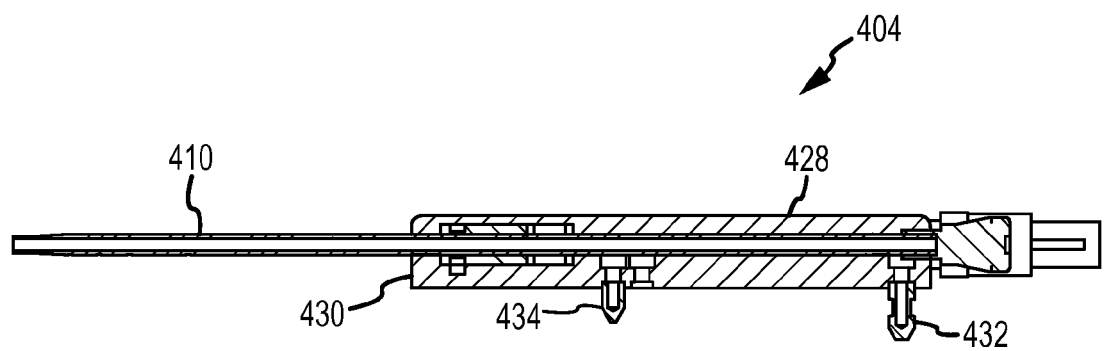
Figure 5D:
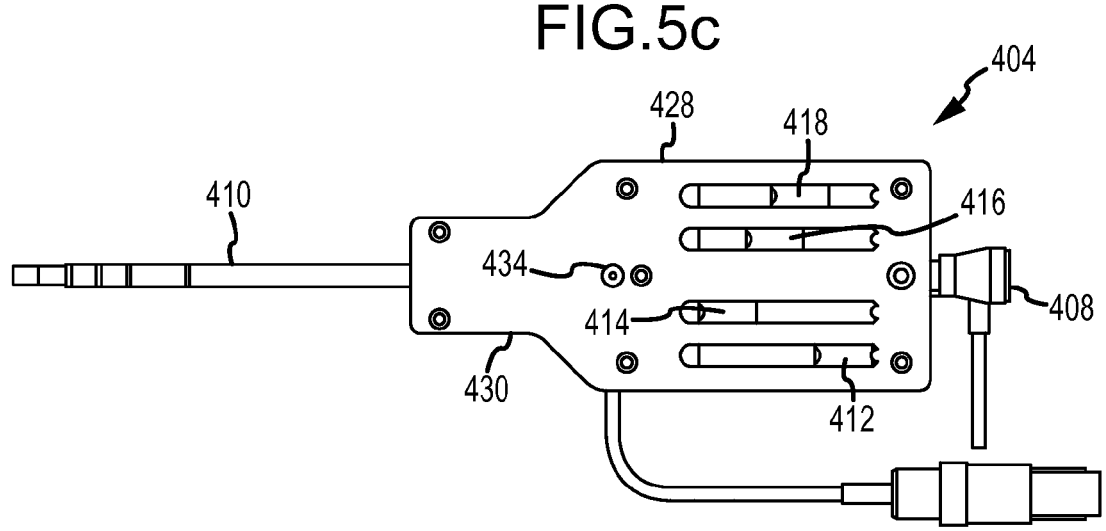
Figure 5E:
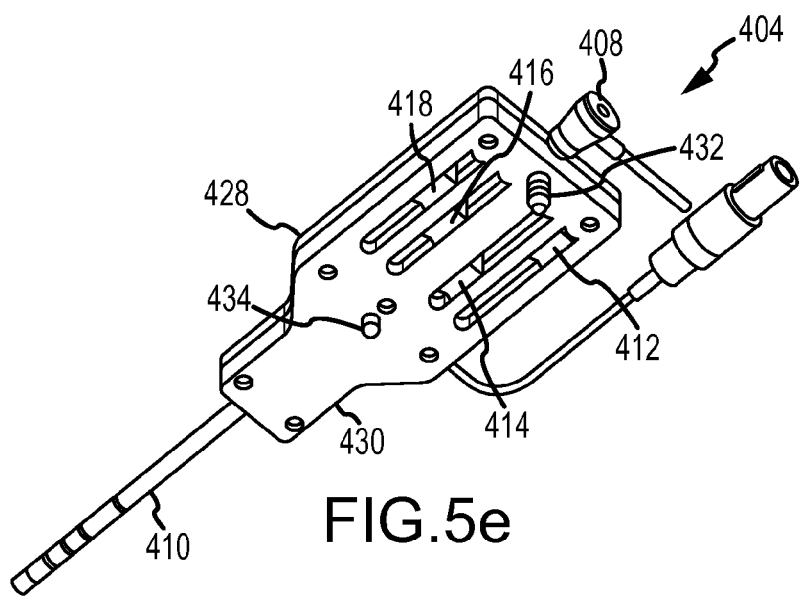
Figure 6A:
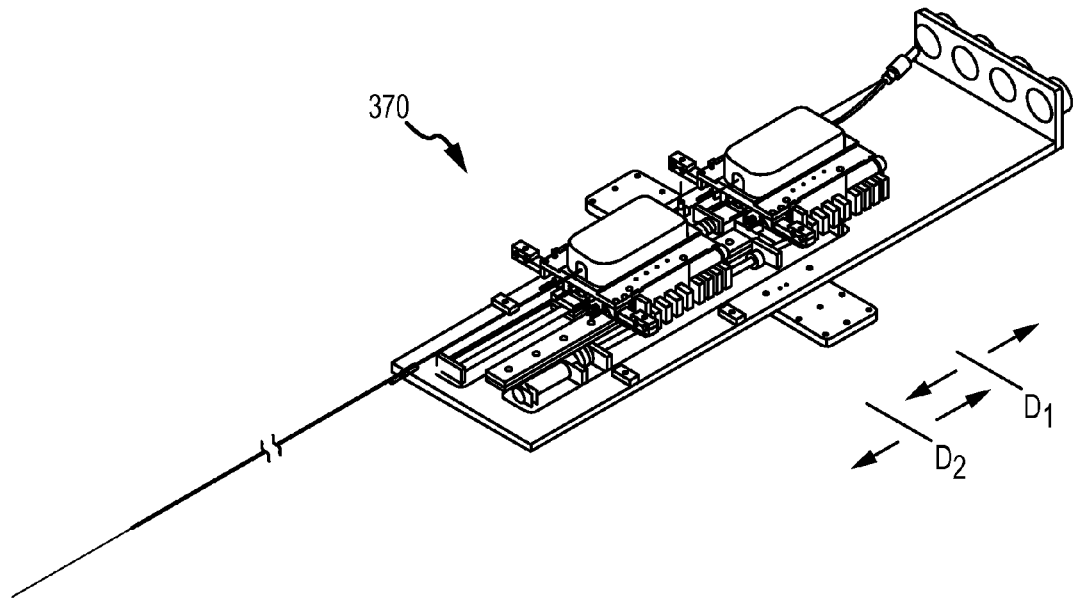
FIGS. 6a-6c are enlarged isometric views of second to fourth embodiments of a robotic catheter manipulator assembly.
Figure 6B:
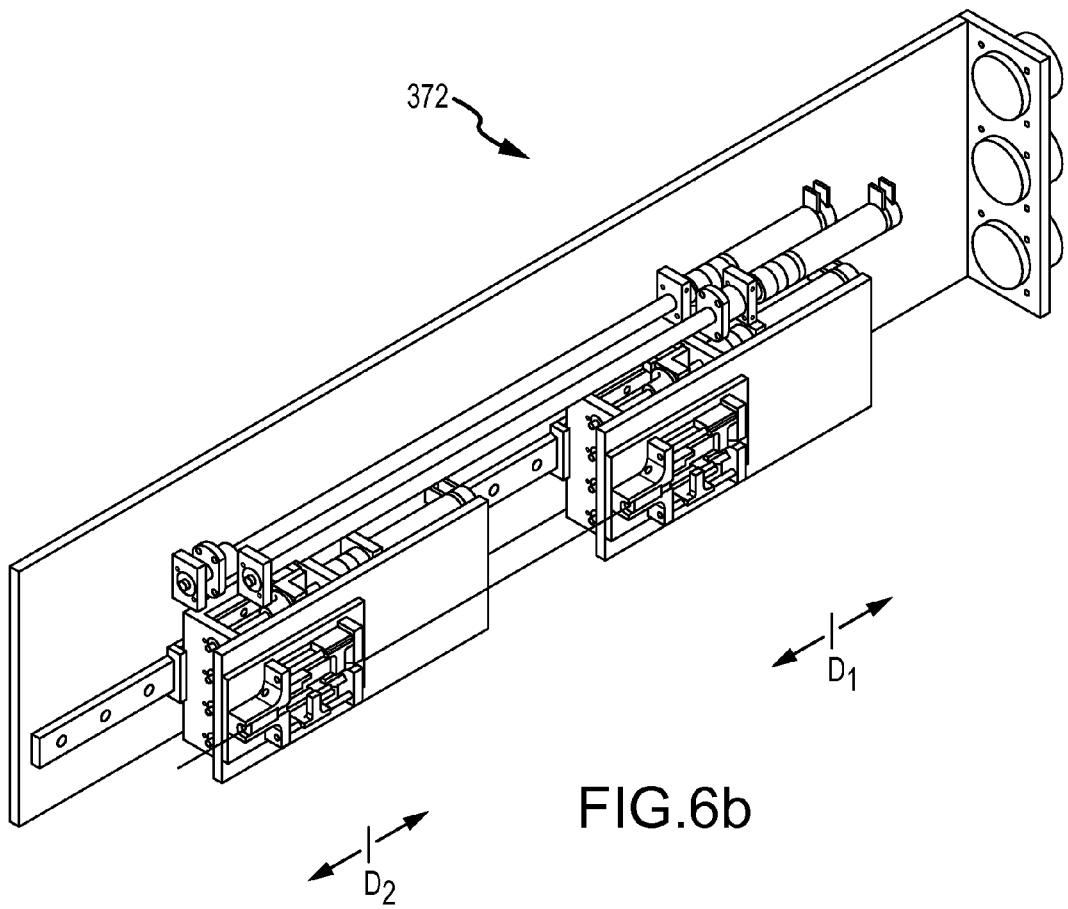
Figure 6C:
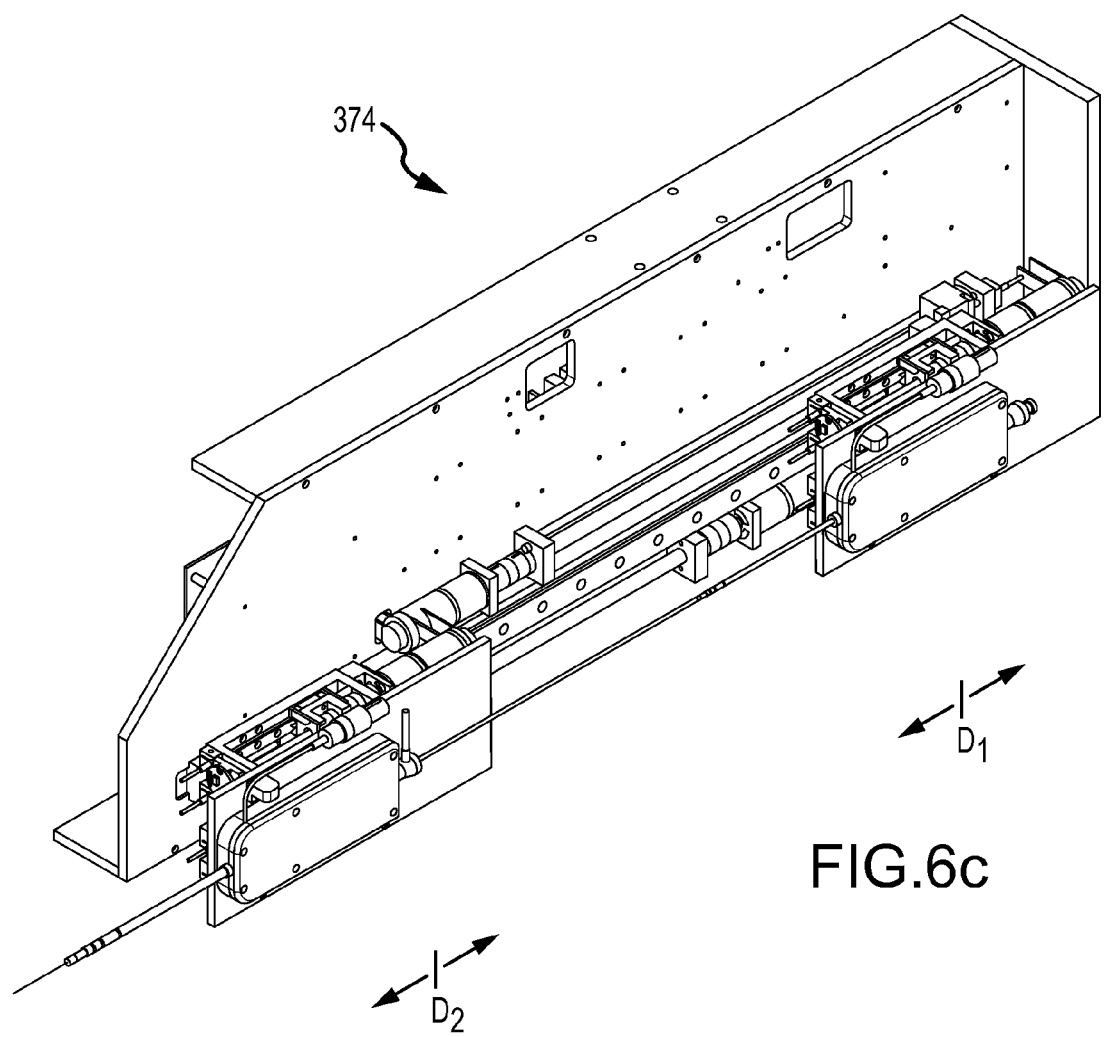

Referring to FIGS. 3*a*-5*e* and as discussed above, catheter and sheath cartridges 402, 404 can be configured to secure or lock down onto respective interconnecting catheter and sheath manipulation bases 308, 310. To couple cartridge 402 (and 404) with base 308 (and 310), one or more locking pins (e.g., 432 in FIGS. 5*a*, 5*d* and 5*e*) on the cartridge can engage one or more mating recesses 360 in the base (see FIG. 4*a*). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, as shown in FIGS. 5*c*, 5*d* and 5*e*, cartridge 402 (and 404) can include one or more locator pins 434 that are configured to passively fit into mating holes on the base (e.g., 364 in FIG. 4*a*).

In an embodiment, a user (e.g., an EP) can first manually position catheter 406 and sheath 410 (with catheter 406 inserted in sheath 410) within the vasculature of a patient. Once the devices are roughly positioned in relation to the heart, the user can then engage or connect (e.g., "snap-in") the catheter cartridge into place on interconnecting/interlocking bases 308, 310 of manipulator assembly 302, for example, by inserting the locking/locating pins 432, 434 of the cartridges into mating holes 360, 364 of respective base 308, 310. When the cartridge is interconnected with the base, each of the plurality of fingers 316, 318, 320 or 322 can fit into recesses formed between the distal edge of slider blocks 412, 414, 416, 418 and a lower portion of the cartridge housing. Such recesses are shown in, for example, FIGS. 5*d* and 5*e*.

Each finger can be designed to be actuated in a proximal direction to correspondingly push each respective slider block. The slider block can be configured to force the finger to self center on its geometry when contact is first made. Such a centering feature can be facilitated by the contact surface of the slider block. For example, as shown in FIGS. 5*d* and 5*e*, the slider block can include an engagement surface (e.g., shaped as a semi-cylindrical recess in the forward facing portion). This surface can be configured to mate or communicate with a matching round portion of a corresponding finger.

With sufficiently rigid coupling between each slider block and a corresponding steering wire, pushing a slider block in a proximal direction can cause an attached steering wire to tension and thus laterally deflect the distal end of the catheter and sheath 406, 410. Moreover, in such an embodiment, because there is no rigid connection between each finger and its associated slider block, the manipulator assembly 302 cannot pull the steering wire in a forward direction. That is, when each block is actuated, it is only possible to tension the steering wire. Furthermore, because the push-actuation of each slider block occurs near that block's bottom surface, a moment can be imposed on the block. Because such a moment can increase the likelihood of the block binding during travel, the length of the block can be optimized to reduce or minimize contact forces between the block and the cartridge housing.

The aforementioned electrical handshake between manipulation bases 308, 310 and catheter and sheath cartridges 402, 404 will be described briefly.

Robotic catheter system 10 can be useful for a variety of procedures and in connection with a variety of tools and/or catheters. Such tools and/or catheters can include, without limitation, spiral catheters, ablation catheters, mapping catheters, balloon catheters, needle/dilator tools, cutting tools, cauterizing tools, and/or gripping tools. The system can additionally include a means of identifying the nature and/or type of catheter/tool cartridge that is installed for use, and/or position or connection related information. The system can automatically access/obtain additional information about the cartridge, such as, without limitation, its creation date, serial number, sterilization date, prior uses, etc.

Further, some embodiments of the system can include an ability to "read" or detect the type or nature of the connected cartridge through the use of memory included with the disposable cartridge together with some data/signal transmission means. By way of example, each cartridge can contain a chip (e.g., an EEPROM chip) that can be electrically interfaced by the manipulator head. Such a chip could, for instance, be programmed during the manufacturing process and can electronically store various data, such as the make; model; serial number; creation date; and/or other special features associated with the cartridge or tool. Additionally the chip can contain other worthwhile information, such as an indication of previous use, catheter specific calibration or model data, and/or any other information that can relate to the safety or performance of the particular device.

In an embodiment, upon interconnecting the cartridge (e.g. 402, 404) with the manipulator head (e.g. 302), a detection means, such as an optical or magnetic sensor, can initially detect the presence of the cartridge. Once presence is detected, the manipulator can energize a chip and initiate data/signal retrieval. Such retrieved data/signal can then be used by the system to control or alter various features and/or displays based on the type of device and/or information provided. While one embodiment can use a chip (e.g., EEPROM), due to its design flexibility, another embodiment can include a wireless transmission device, such as an RFID, which can be employed to facilitate the data storage/transfer instead of, or in addition to a chip.

Referring to FIGS. 1, 2a-2d and 7a-14j generally, various embodiments of manipulator support structure 500 are disclosed.

Figure 2D:
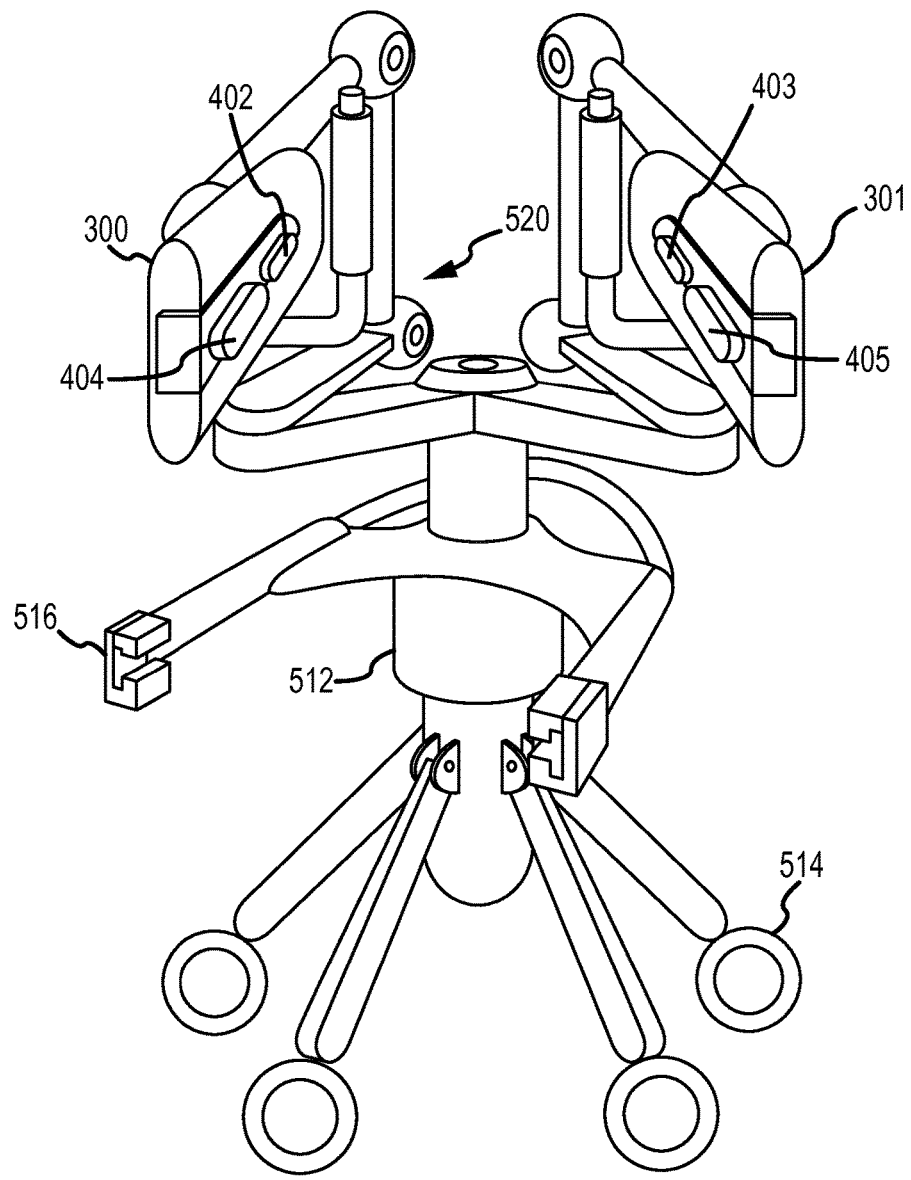
FIG. 2d is a second embodiment of a robotic catheter manipulator support structure employing two manipulator assemblies.
Figure 7A:
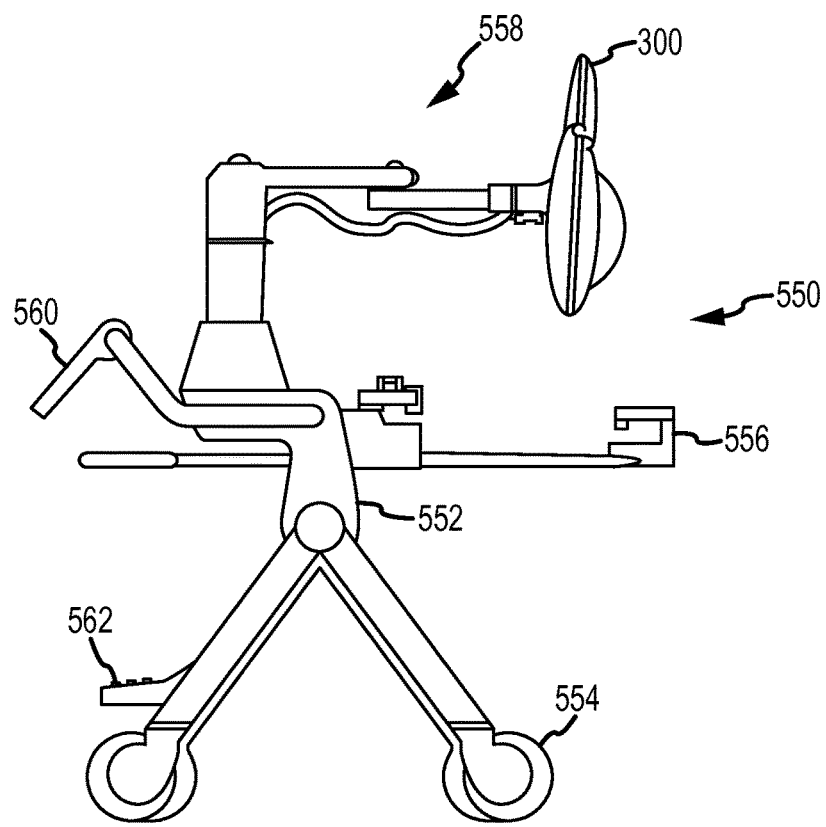
FIGS. 7a and 7b are diagrammatic views of a second embodiment of a robotic catheter manipulator support structure.
Figure 7B:
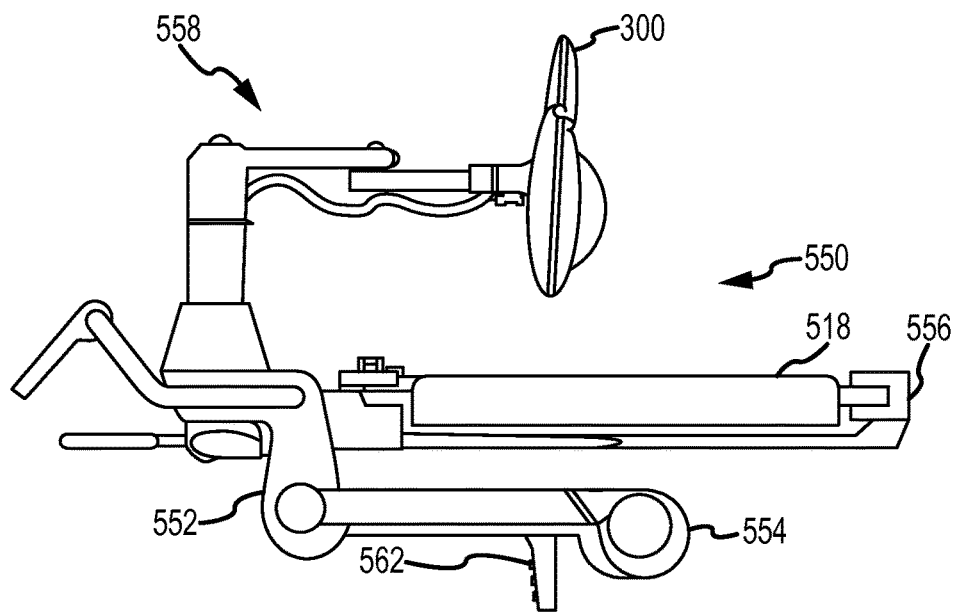

Specifically, referring to FIGS. 1 and 2a-2d, isometric diagrammatic views of a first embodiment of a robotic catheter manipulator support structure 510 (hereinafter "manipulator support structure") are illustrated. Manipulator support structure 510 can generally include a support frame 512 including retractable wheels 514 and attachment assembly 516 for attachment to operation bed 518. A plurality of support linkages 520 can be provided for accurately positioning one or more robotic catheter manipulator assemblies 300/302. As shown in FIGS. 7a and 7b for a second embodiment 550 of manipulator support structure, in use, manipulator support structure 510 can be wheeled to operation bed 518 and attached thereto by attachment assembly 516. Thereafter, wheels 514 can be retracted as shown in FIG. 7b. FIG. 2d illustrates an embodiment where multiple manipulator assemblies are provided on a common manipulator support structure 510. As generally illustrated in FIG. 2d, a second manipulator 301 can be identical to the first manipulator 300, though can include cartridges 403 and 405 that are designed to perform different tasks than the cartridges 402, 404 on the first manipulator 300.

In an embodiment, as generally illustrated in FIG. 2d, multiple manipulators 300, 301 can be used together during a single procedure. In such a procedure, each manipulator can control a catheter extending through a different anatomical lumen. For example, one catheter can extend into the left femoral vein, while another catheter can extend through the right femoral vein. Alternatively, or additionally, one or more catheters can extend through the right or left subclavian or internal jugular veins. In an embodiment, each manipulator 300, 301 can control the positioning of one or more distal tools, where the tools can be similar or different in nature. In one embodiment, two manipulators can control the positioning of two ablation electrodes. In another embodiment, one manipulator (e.g., manipulator 300) can control an ablation catheter, while a second manipulator (e.g., manipulator 301) controls a mapping electrode. In a another embodiment, the system can be configured to test the effectiveness of an isolation procedure by using one manipulator to stimulate tissue, while a second manipulator is configured to measure transmitted impulses (or lack thereof). It should be understood that any combination of ablation, mapping, stimulation, ultrasound, cautery, or surgical tips can be used in conjunction with any of the one or more manipulators.

Referring to FIGS. 7a and 7b, isometric diagrammatic views of the second embodiment of a manipulator support structure 550 are illustrated. Manipulator support structure 550 can generally include a support frame 552 including retractable wheels 554 and attachment assembly 556 for attachment to operation bed 518. A plurality of support linkages 558 can be provided for accurately positioning robotic catheter manipulator assembly 300. As shown in FIG. 7a, a handle 560 can be provided for assisting a user with extending attachment assembly 556 to an opposite side of bed 518. As shown in FIGS. 7a and 7b, in use, manipulator support structure 550 can be wheeled to operation bed 518 and attached thereto by attachment assembly 556. Thereafter, wheels 554 can be pivoted upwards upon release by a step-pedal system 562 to be positioned out of the path of operating personnel.

Figures 8B, 8C:
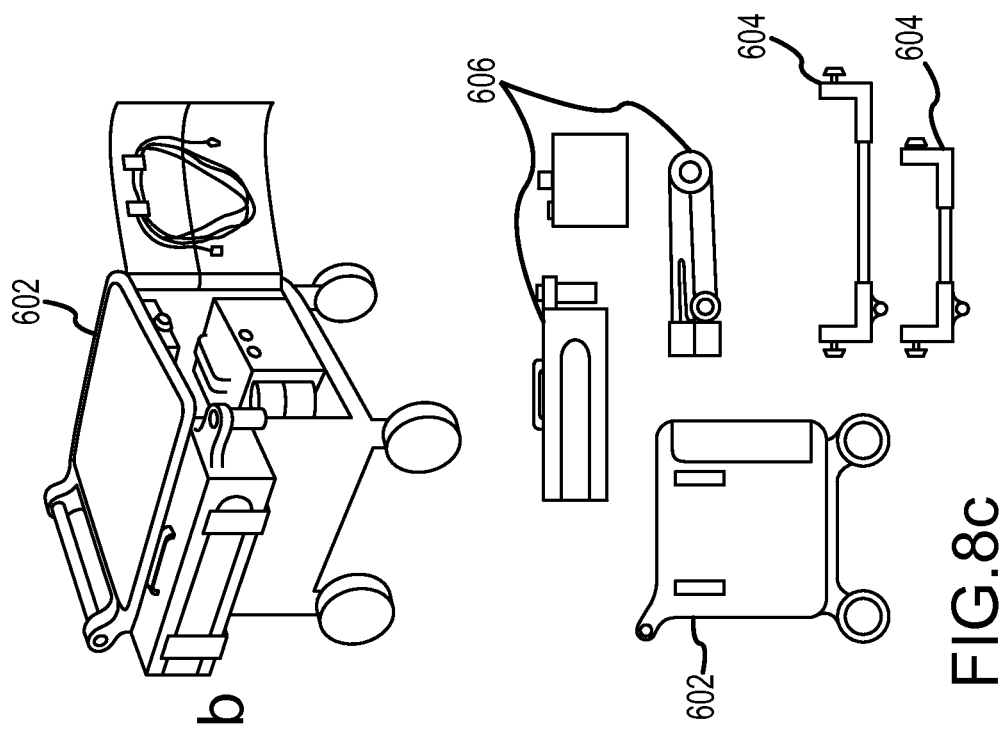
FIGS. 8a-8c are isometric and related diagrammatic views of a third embodiment of a robotic catheter manipulator support structure, and various components thereof.
Figure 8A:
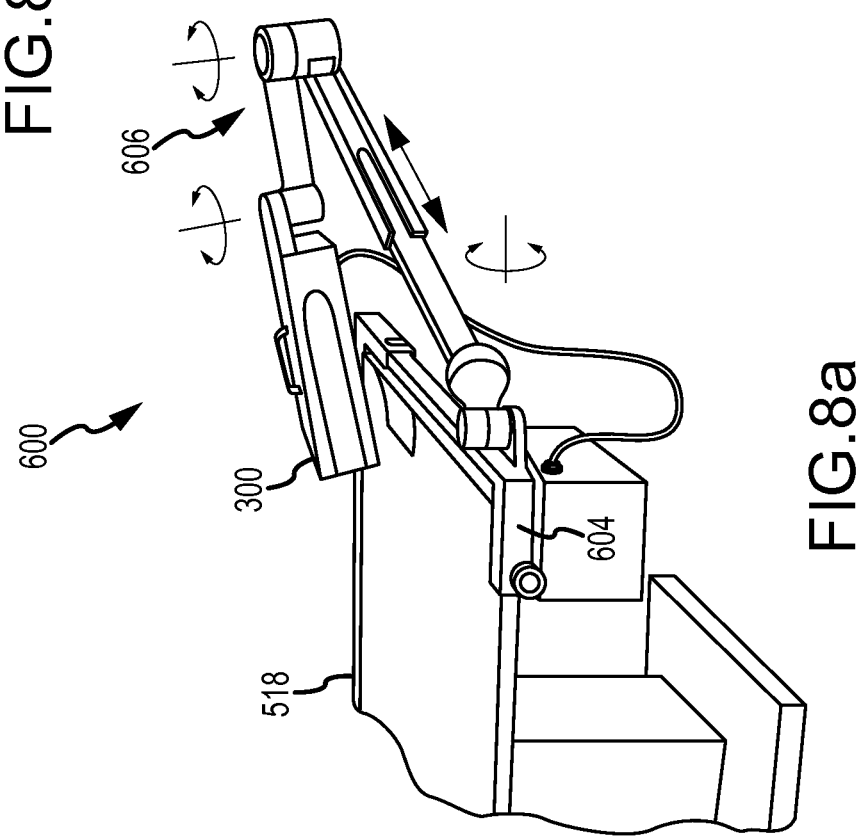

Referring to FIGS. 8a-8c, isometric and related diagrammatic views of a third embodiment of a manipulator support structure 600, and various components thereof are illustrated. Manipulator support structure 600 can generally include a portable unit 602 for transportation of manipulator support structure 600 and its related components. Structure 600 can include attachment assembly 604 for attachment to operation bed 518, and a plurality of support linkages 606 for accurately positioning robotic catheter manipulator assembly 300. Referring to FIGS. 8a and 8b, in use, manipulator support structure 600 can be wheeled to operation bed 518 and attached thereto by attachment assembly 604, and thereafter detached and placed in portable unit 602 for transportation.

Referring to FIGS. 9a and 9b, isometric and related diagrammatic views of a fourth embodiment of a manipulator support structure 650 are illustrated. Manipulator support structure 650 can generally include a track mounted unit 652 for movement of manipulator support structure 650 and its related components. Structure 650 can include attachment assembly 654 for attachment to ceiling or otherwise mounted track 656, and a plurality of support linkages 658 for accurately positioning robotic catheter manipulator assembly 300. Referring to FIGS. 9a and 9b, in use, manipulator support structure 650 can be positioned relative to operation bed 518 and locked in position during use, and moved out of the use position or otherwise re-configured to a stowed position by re-positioning of support linkages 658. As shown in FIG. 9b, manipulator support structure can be moved generally horizontally and vertically for positioning and removal from the area of operation bed 518.

Referring to FIGS. 10a-10c, isometric and related diagrammatic views of a fifth embodiment of a manipulator support structure 700 are illustrated. Manipulator support structure 700 can generally include a fixed unit 702 for movement of manipulator support structure 700 and its related components. Structure 700 can include attachment assembly 704 for attachment to the floor, and a plurality of support linkages 706 for accurately positioning robotic catheter manipulator assembly 300. In use, manipulator support structure 700 can be mounted in place relative to operation bed 518, or alternatively, bed 518 can be positioned adjacent structure 700. After use, structure 700 can be re-configured to a stowed position by re-positioning of support linkages 706.

Figure 11B:
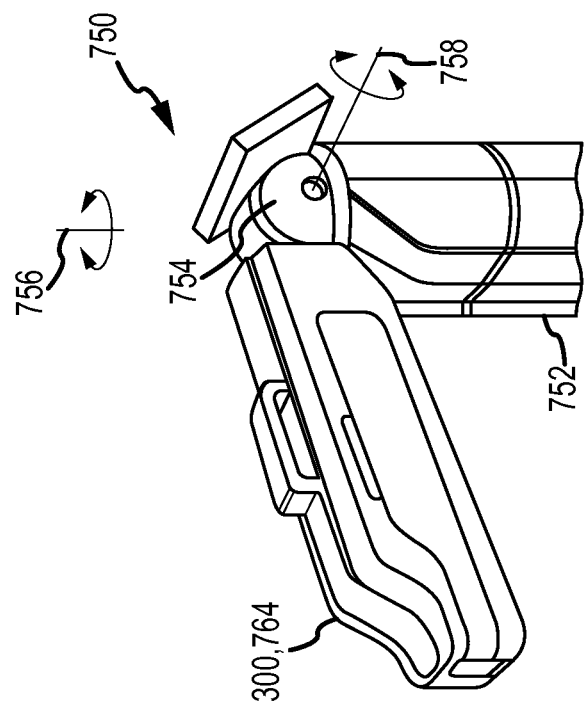
FIGS. 11a-11h are isometric and related diagrammatic views of a sixth embodiment of a robotic catheter manipulator support structure, and various components thereof.
Figure 11A:
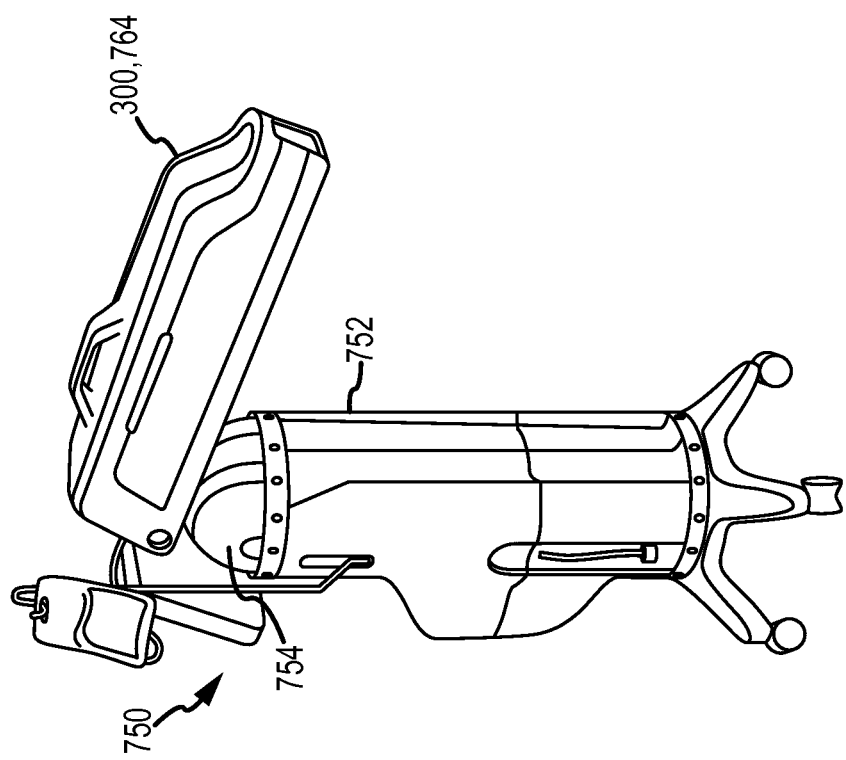
Figure 11C:
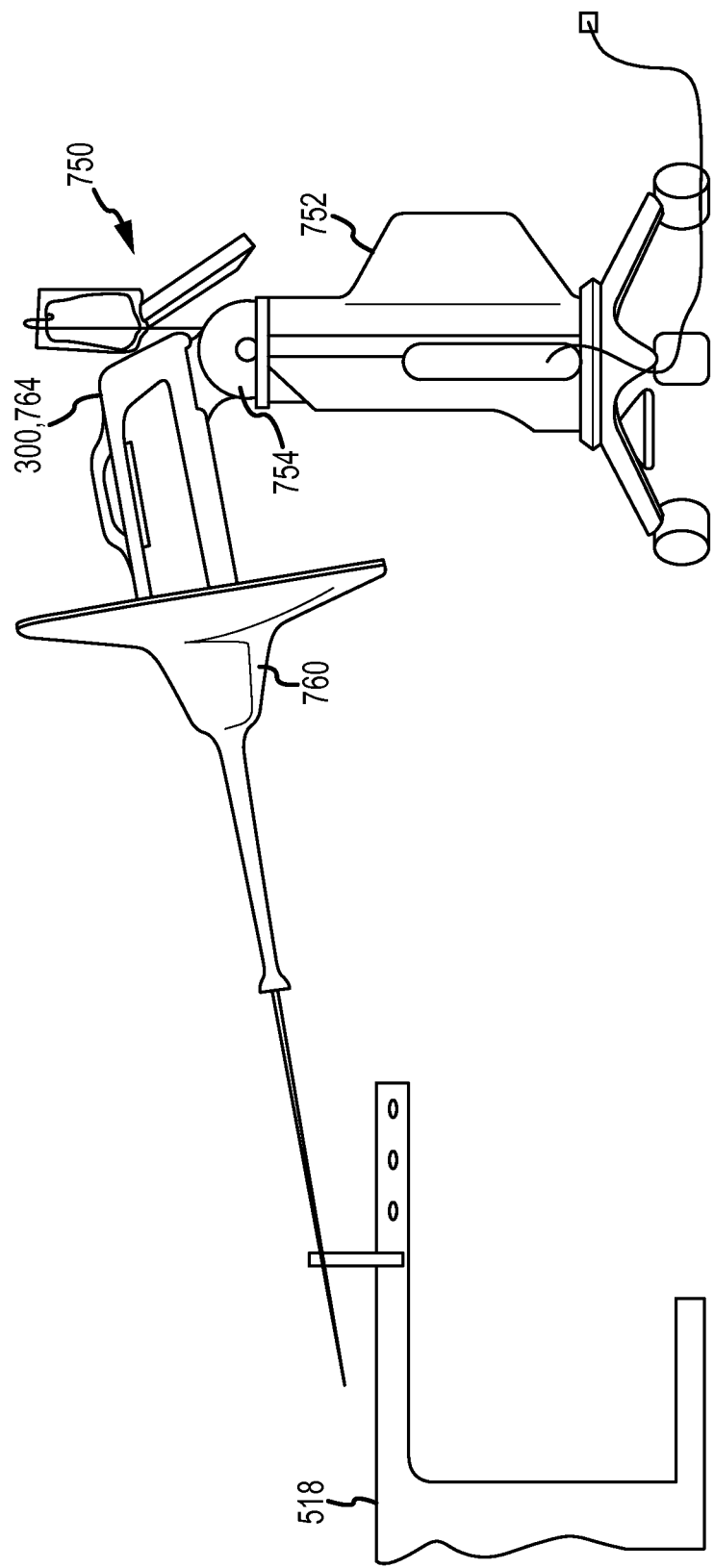
Figure 11D:
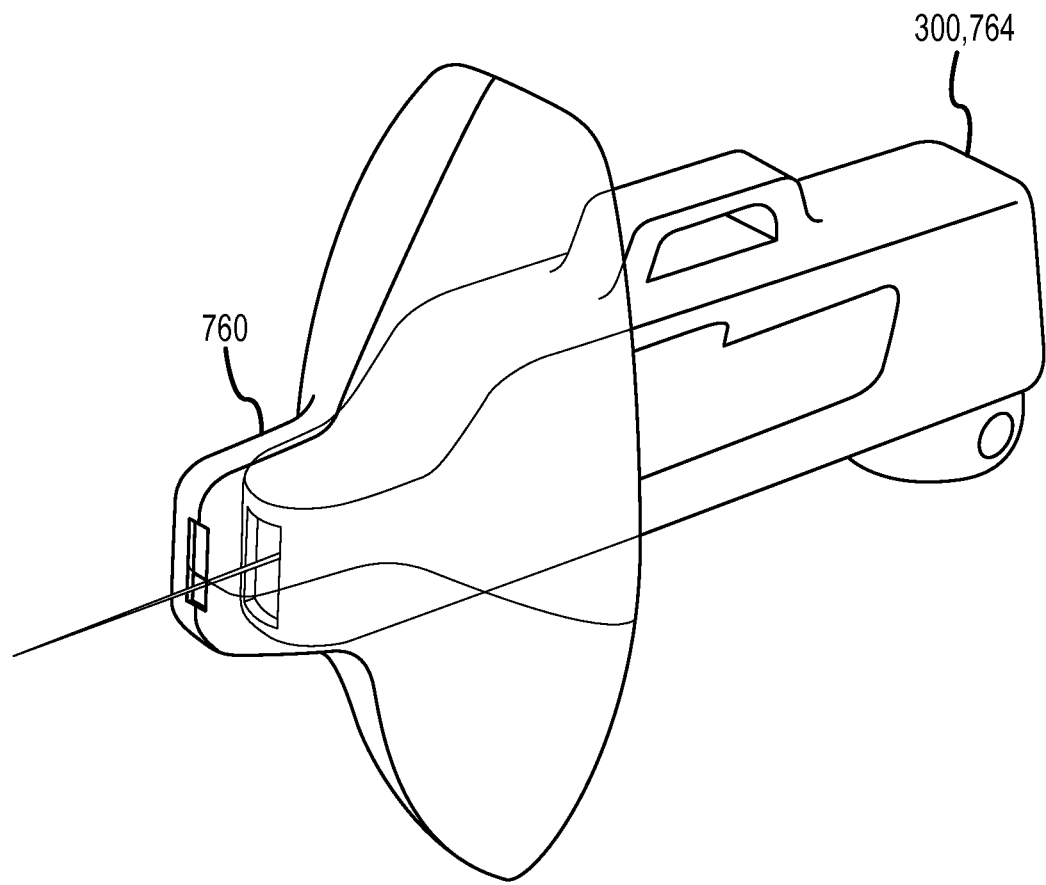
Figure 11E:
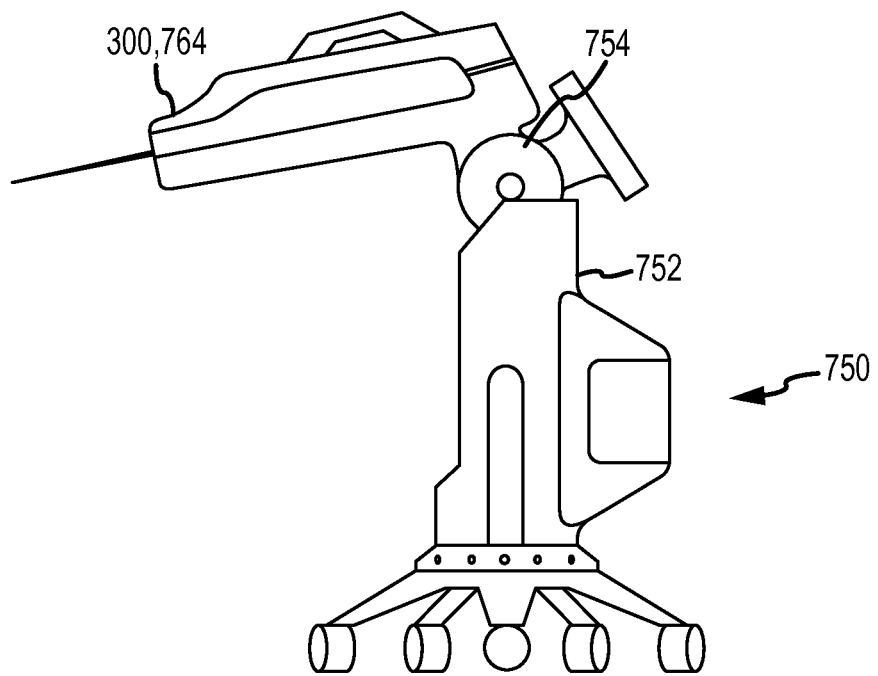

Referring to FIGS. 11*a*-11*h*, isometric and related diagrammatic views of a sixth embodiment of a manipulator support structure 750, and various components thereof are illustrated. Manipulator support structure 750 can generally include a portable unit 752 for movement of manipulator support structure 750 and its related components. Structure 750 can include a pivotable support 754 for accurately positioning robotic catheter manipulator assembly 300. Pivotable support 754 can be pivotable about generally vertical and horizontal axis 756, 758. As shown in FIGS. 11*c* and 11*d*, a disposable sterile shield 760 can be positionable on robotic catheter manipulator assembly 300. Sterile shield 760 can isolate the manipulator from a sterile field in an operating room/EP lab environment. The sterile interface can optionally include a sealing material or component, such as a pliable gasket-type material, to allow the manipulator fingers (e.g. 316, 318, 320 and 322) to interact with the cartridge (e.g. 402, 404) without operational interference, but while maintaining a necessary degree of sterility. Such a barrier or drape can permit the manipulator to be re-used without requiring additional sterilization.

Figure 11F:
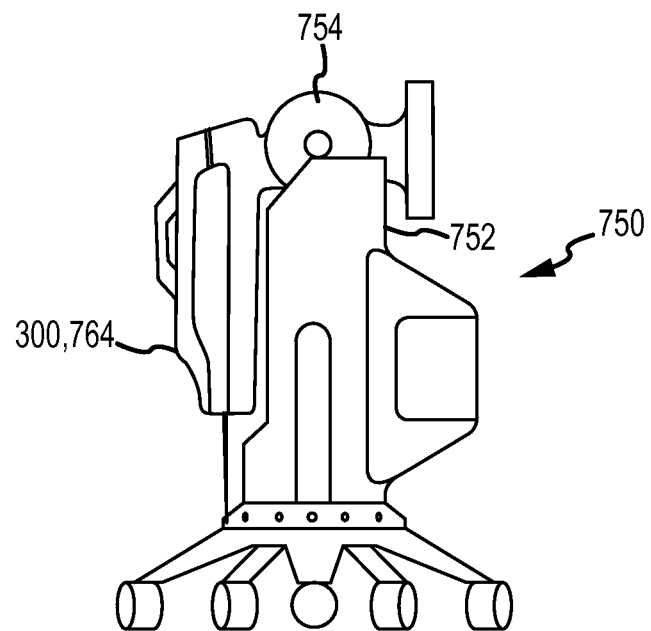
Figure 11G:
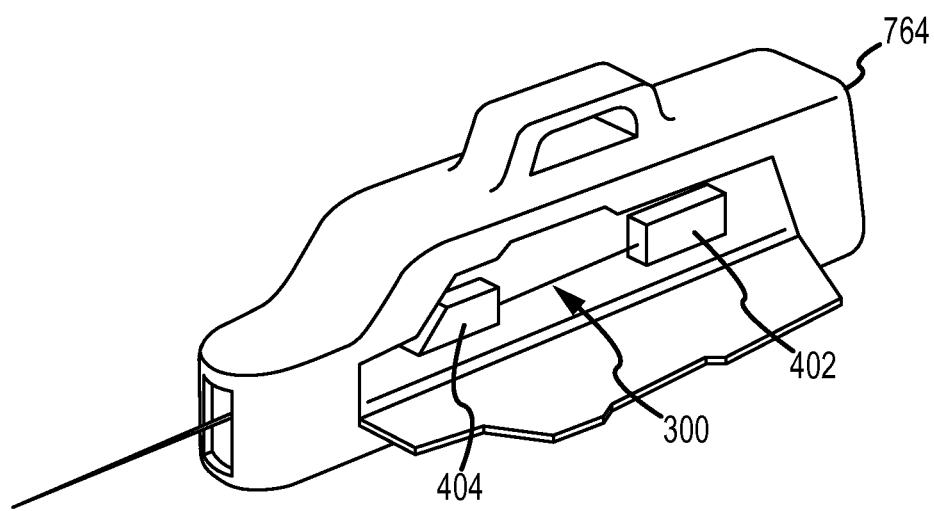
Figure 11H:
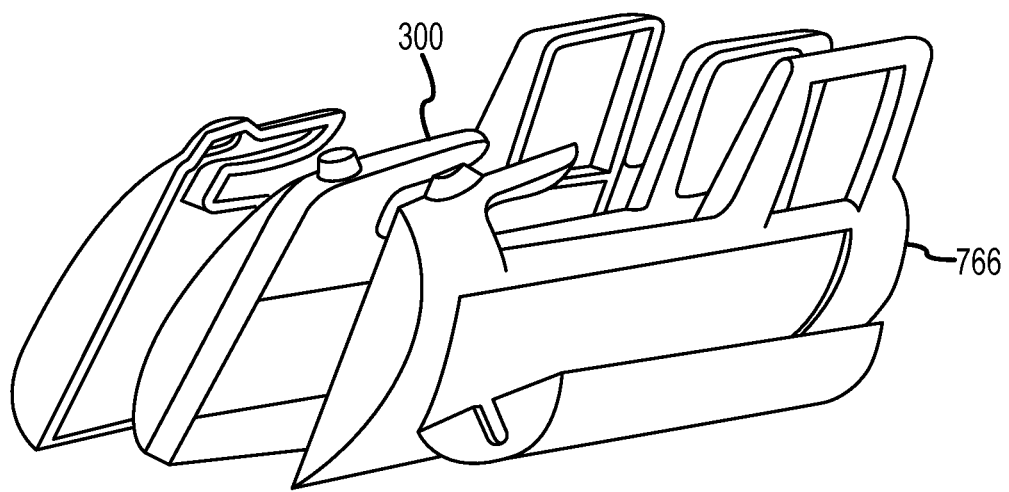

Referring to FIGS. 11*a*-11*h*, in use, manipulator support structure 750 can be placed next to operation bed 518, or alternatively, bed 518 can be positioned adjacent structure 750, with an appropriate sterile shield 760 disposed on robotic catheter manipulator assembly 300. After use, structure 750 can be collapsed as shown in FIG. 11*f*. As shown in FIG. 11*g*, cartridges 402, 404 can be attached or replaced as needed by access via a hinged cover of manipulator case 764, or alternatively, as shown in FIG. 11*h*, a sectioned case 766 can be provided for cartridge replacement or access to robotic catheter manipulator assembly 300.

Figure 12A:
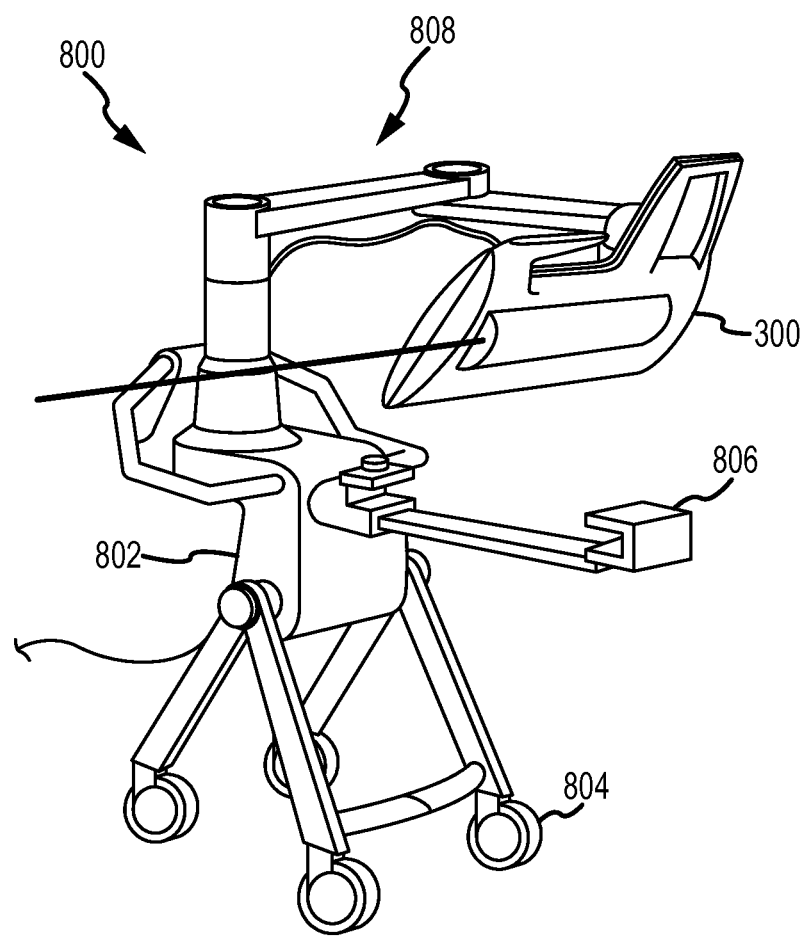
FIGS. 12a-12c are isometric and related diagrammatic views of a seventh embodiment of a robotic catheter manipulator support structure.
Figure 12B:
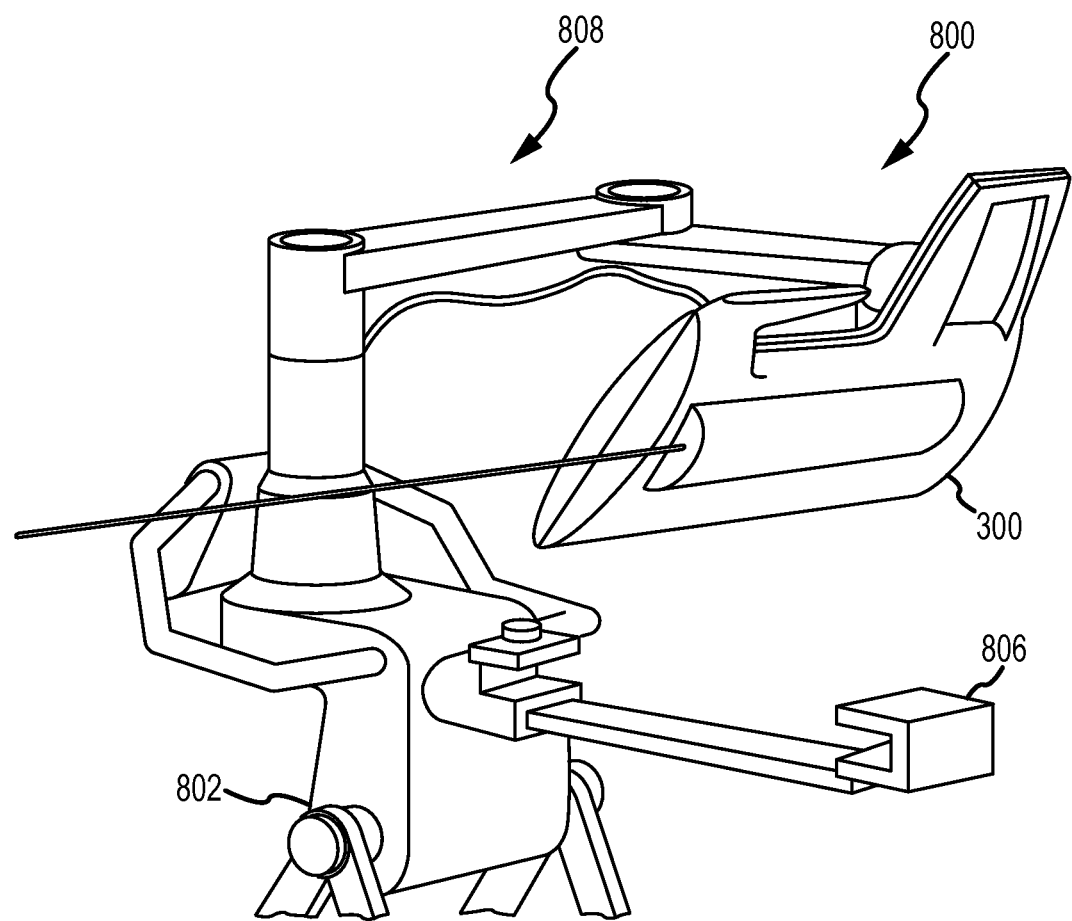
Figure 12C:
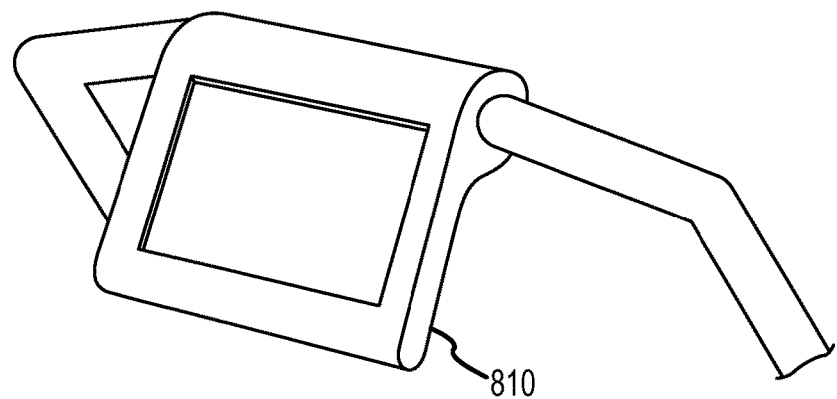

Referring to FIGS. 12*a*-12*c*, isometric and related diagrammatic views of a seventh embodiment of a manipulator support structure 800, and related components are illustrated. Manipulator support structure 800 can be similar in design to support structure 550 of FIGS. 7*a* and 7*b*. Manipulator support structure 800 can generally include a support frame 802 including wheels 804 and attachment assembly 806 for attachment to operation bed 518. A plurality of support linkages 808 can be provided for accurately positioning robotic catheter manipulator assembly 300. As shown in FIG. 12*c*, a touch-screen interface 810 can be provided for controlling operation of robotic catheter manipulator assembly 300. As shown in FIGS. 12*a* and 12*b*, and FIGS. 7*a* and 7*b* for support structure 550, in use, manipulator support structure 800 can be wheeled to operation bed 518 and attached thereto by attachment assembly 806.

Figure 13D:
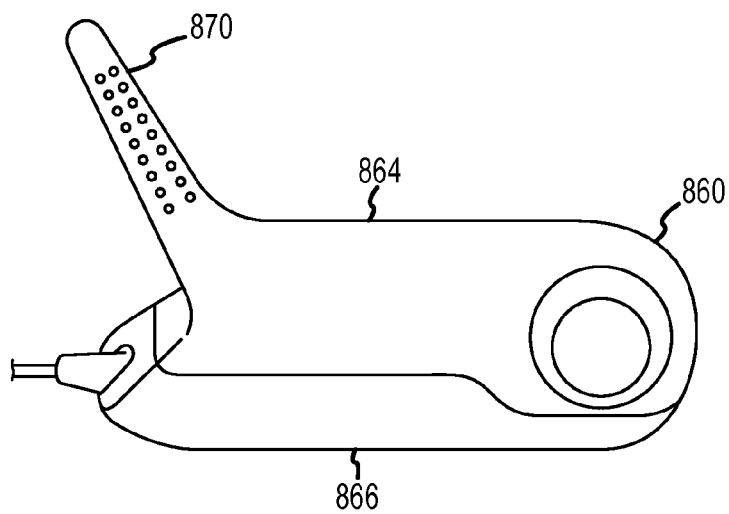
FIGS. 13a-13o are isometric and related diagrammatic views of a eighth embodiment of a robotic catheter manipulator support structure.
Figure 13E:
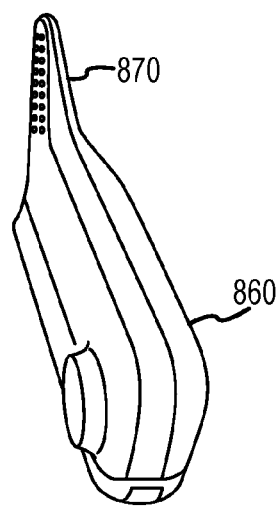
Figure 13F:
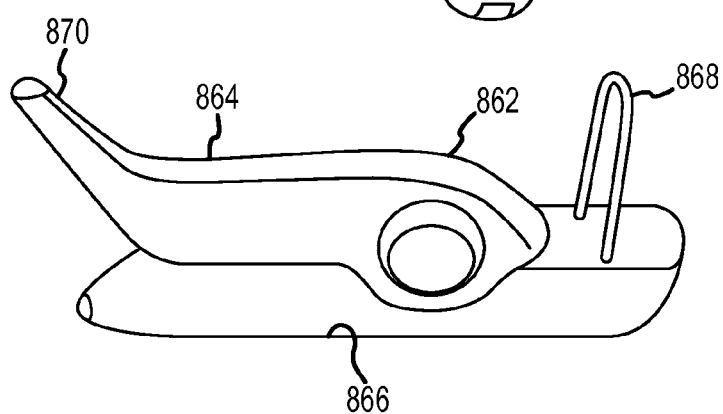
Figure 13G:
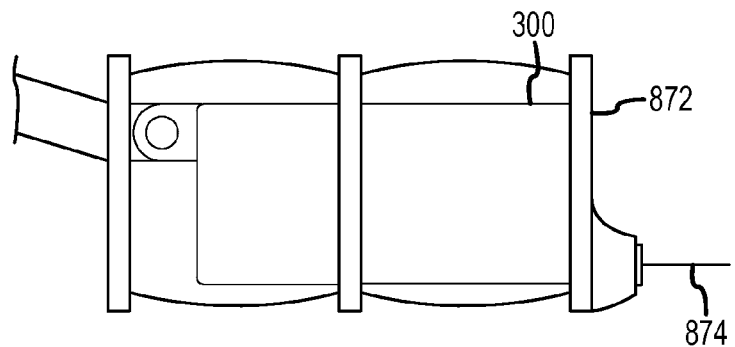
Figure 13H:
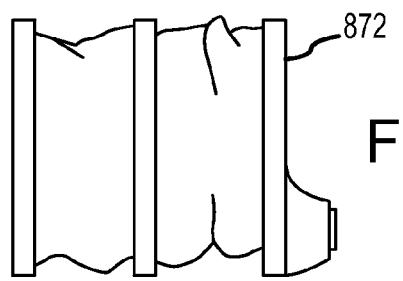
Figure 13I:
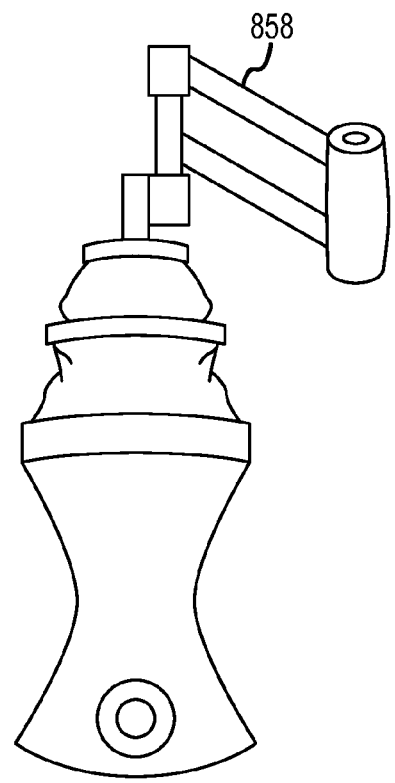
Figure 13O:
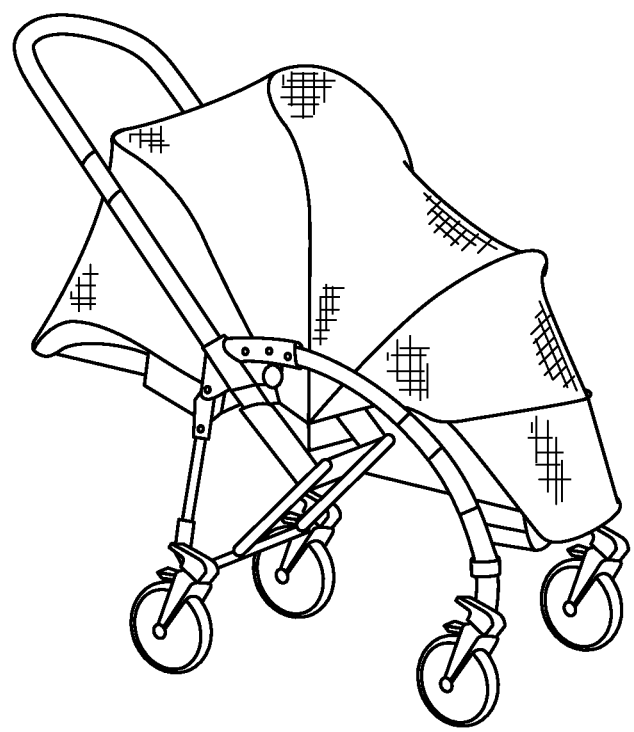

Referring to FIGS. 13*a*-13*o*, isometric and related diagrammatic views of an eighth embodiment of a manipulator support structure 850, and related components are illustrated. Manipulator support structure 850 can be similar in design to support structure 550 of FIGS. 7*a* and 7*b*. Manipulator support structure 850 can generally include a support frame 852 including wheels 854 and attachment assembly 856 for attachment to operation bed 518. A plurality of support linkages 858 can be provided for accurately positioning robotic catheter manipulator assembly 300. As shown in FIG. 13*a*, and FIGS. 7*a* and 7*b* for support structure 550, in use, manipulator support structure 850 can be wheeled to operation bed 518 and attached thereto by the attachment assembly 856. Referring to FIGS. 13*d* and 13*e*, a disposable cover 860 can be provided for robotic catheter manipulator assembly 300, with the cover being used with any of the embodiments of manipulator support structures disclosed herein. As shown in FIGS. 13*d*-13*f*, disposable covers 860 and 862 can include a two part top and bottom cover 864, 866, with a saline bag attachment loop 868 and integrated handle 870. As shown in FIGS. 13*g* and 13*h*, cover 872 can be collapsible for permitting use of robotic catheter manipulator assembly 300 by exposing catheter/sheath 874. As shown in FIGS. 13*j*-13*n*, a cover 876 can be opened and removed to permit unrestrained operation of manipulator assembly 300. As shown in FIG. 13*o*, another transportation system for the aforementioned manipulator support structures and related components is illustrated.

Figure 14A:
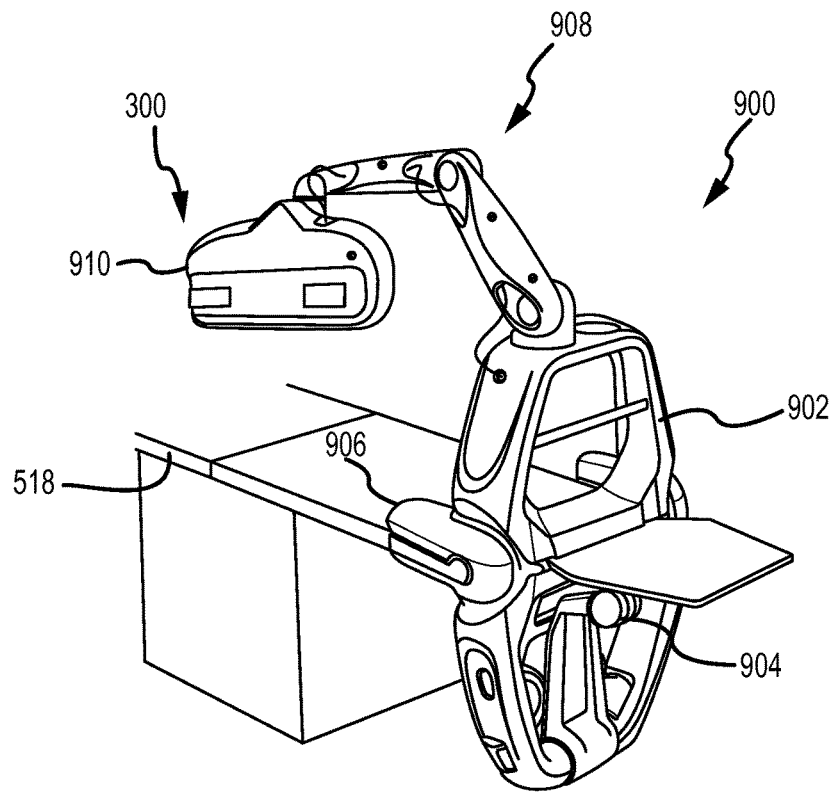
FIGS. 14a-14j are isometric and related diagrammatic views of a ninth embodiment of a robotic catheter manipulator support structure, and various components thereof.
Figure 14B:
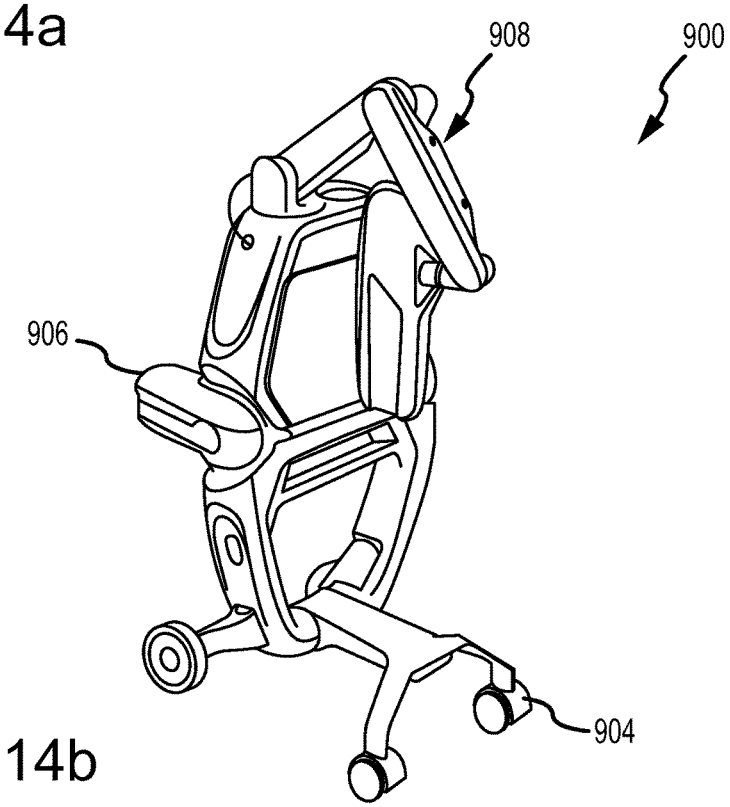

Referring to FIGS. 1 and 14*a*-14*j*, isometric diagrammatic views of a ninth embodiment of a manipulator support structure 900 and various components thereof are illustrated. Manipulator support structure 900 can generally include a support frame 902 including retractable wheels 904 and releasable attachment assembly 906 for attachment to operation bed 518. A plurality of support linkages 908 can be provided for accurately positioning robotic catheter manipulator assembly 300. As shown in FIGS. 14*a* and 14*b*, manipulator support structure 900 is illustrated as respectively disposed in the use and stowed/transport configurations. As shown in FIGS. 14*a* and 14*b*, in use, manipulator support structure 900 can be wheeled to operation bed 518 and attached thereto by attachment assembly 906. Thereafter, wheels 904 can be pivoted upwards upon release by a step-pedal (not shown) to be positioned out of the path of operating personnel.

Figure 14C:
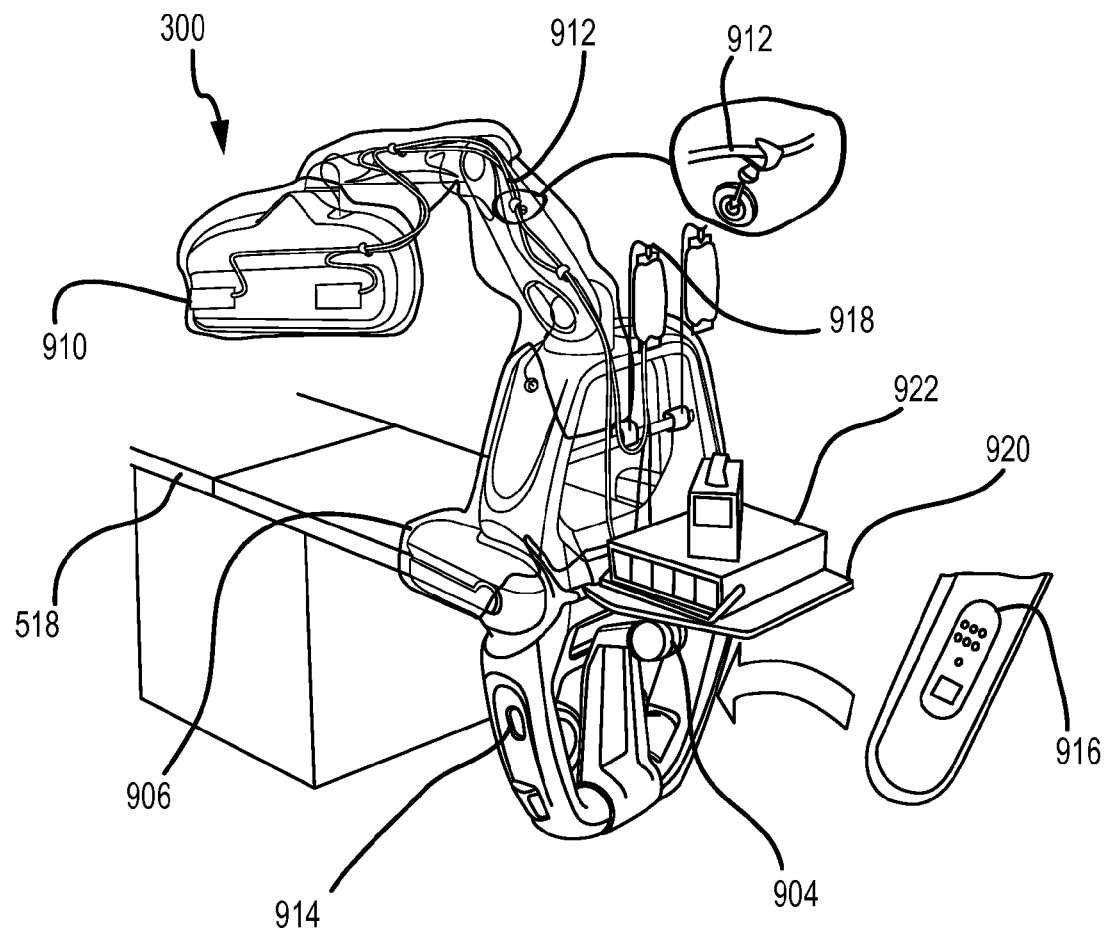

Referring to FIGS. 14*a*-14*c*, manipulator support structure 900 can include a sterile cover 910 disposed over manipulator assembly 300. Other components can include irrigation tubes 912, a USB/power connector 914, and a control module 916 including a power port, network port and an EnSite™ system connection. Saline bags can be removably hung at hangers 918, and a foldable shelf 920 can be provided for equipment, such as, a saline pump and/or ablation generator 922.

Figure 14D:
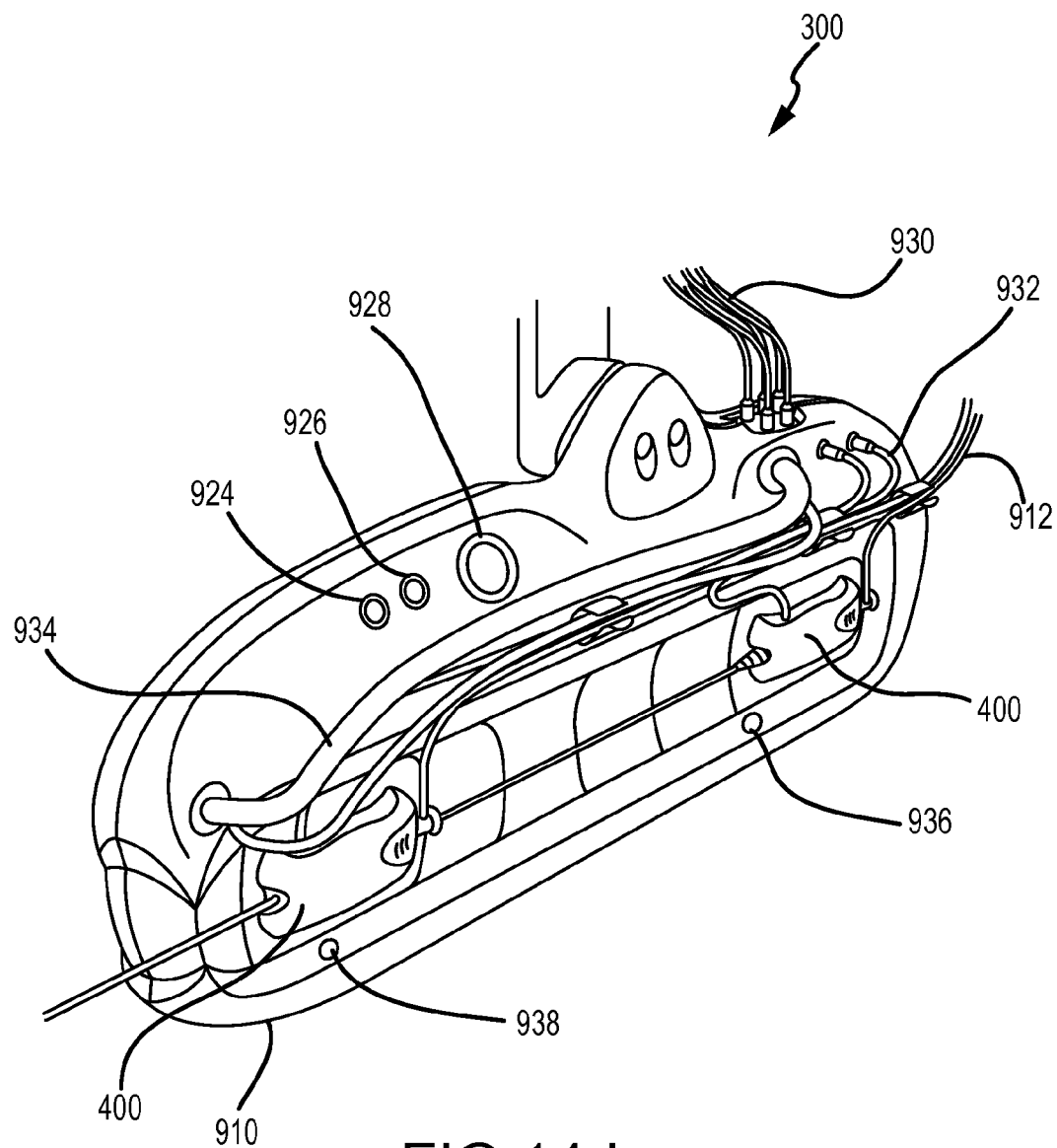
Figure 14E:
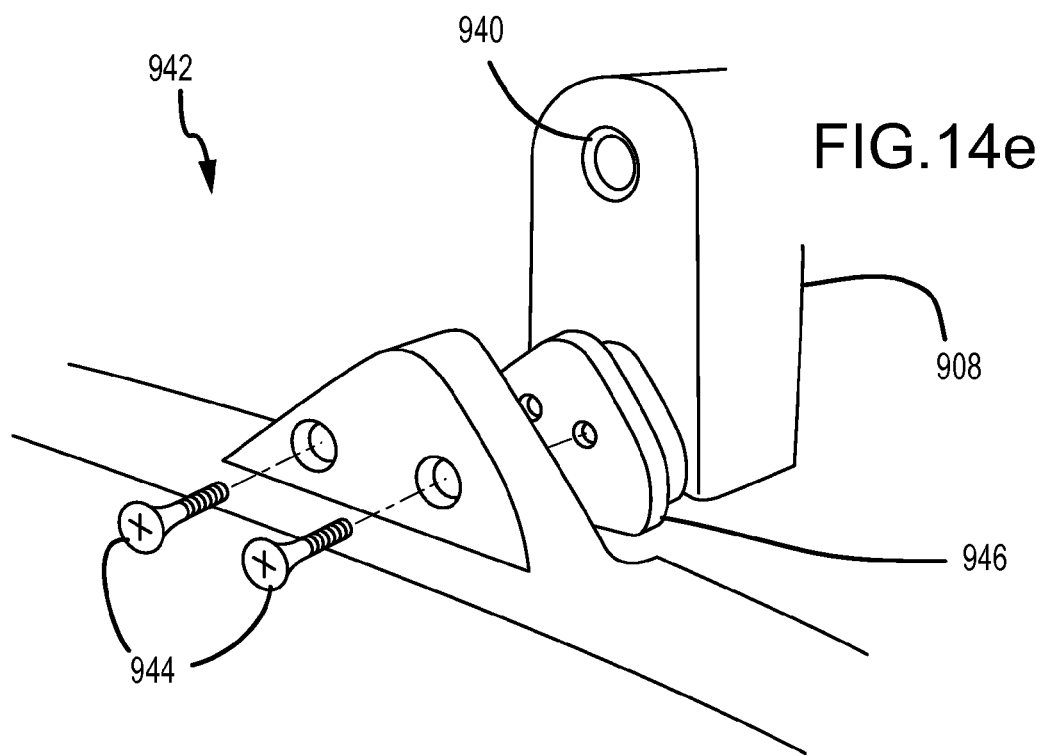
Figure 14F:
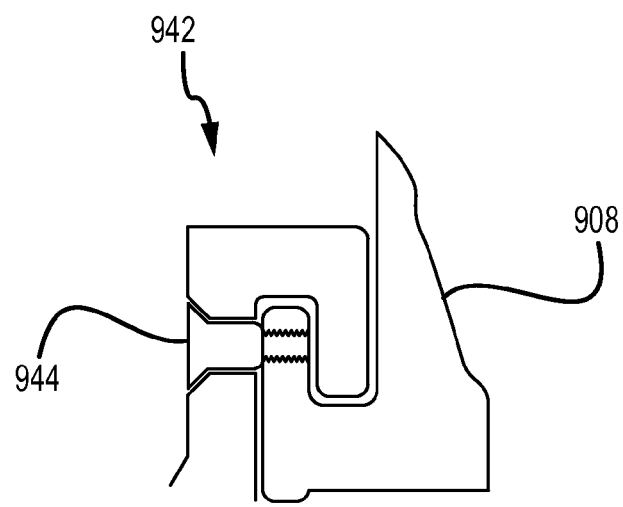

Referring to FIG. 14*d*, an enlarged view of manipulator assembly 300 of FIG. 1 is illustrated. As shown in FIG. 14*d*, manipulator assembly 300 including sterile cover 910 can further include power on/off switches 924, 926, and an emergency power switch 928. The manipulator and cartridge electrical/control connections can be provided at 930, 932. A handle 934 can be used to maneuver manipulator assembly 300 as needed. Appropriate LEDs 936, 938 can be provided for indicating proper connection of the catheter and sheath cartridges. As shown in FIGS. 14*d*-14*f*, manipulator assembly 300 can be pivotally connected to support linkages 908 at pivot point 940 by a two point rigid connection 942 including fasteners 944 and washer/aligner 946.

Figure 14G:
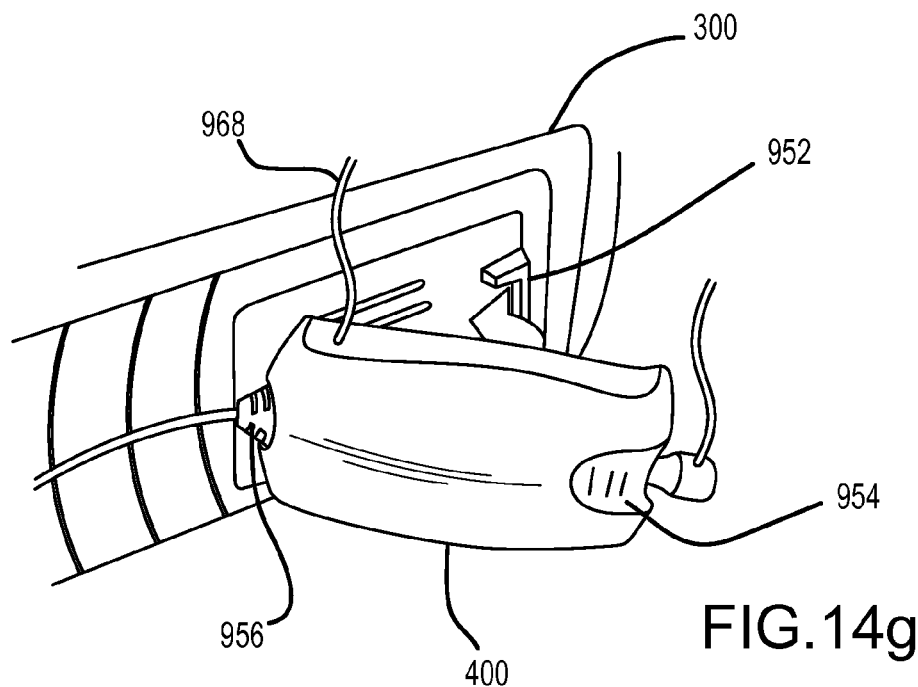
Figure 14H:
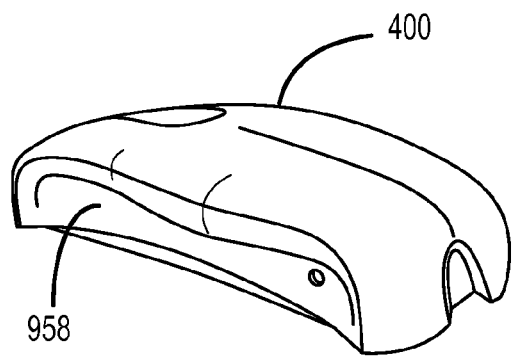
Figure 14I:
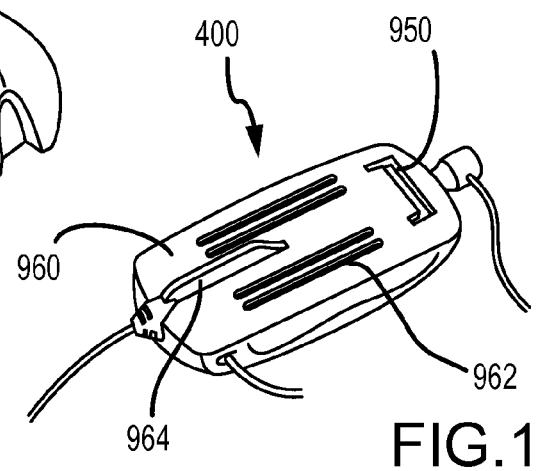
Figure 14J:
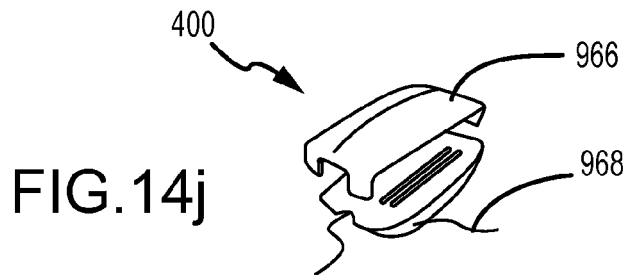

Referring to FIGS. 14*a*-14*c* and 14*g*-14*j*, for the ninth embodiment of manipulator support structure 900, cartridges 400 can include a cut-out 950 sized for a resistance snap-fit onto detent 952 of a manipulation base. A release button 954 can be provided for release of the cartridges from manipulator assembly 300. As shown in FIG. 14*g*, cartridges 400 can include a flexible connection for the catheter/sheath at strain relief connection 956, and electrical connection 968. As shown in FIG. 14*h*, an ergonomic grip area 958 can be provided for facilitating attachment, detachment and grasp of the cartridges. Referring to FIG. 14*i*, each cartridge can include a guide keel 960 including control pin slots 962 and control detent 964 engageable with respective detents and slots in the manipulation base (see FIG. 14*g*). Further, as shown in FIG. 14*j*, a sterile cap 966 can be provided for storage and transport of the cartridges, and removal of the cap for use. Those skilled in the art would readily appreciate in view of this disclosure that the cartridge designs of FIGS. 14g-14j can be utilized in combination with any of the other manipulator assemblies and sub-components disclosed herein, or in the above-identified commonly owned and copending applications.

Based on the discussion above, the aforementioned articulated support structures can hold manipulator assembly 300 in a position to better facilitate treatment or therapy (e.g., adjacent the femoral vein/artery to promote catheterization). Such support structures discussed in reference to FIGS. 2a-14j can, without limitation, include joints that can include a gas or hydraulic assist on each joint, and can further include a braking mechanism to decelerate or lock any moving component in place. The gas-hydraulic assist mechanisms can be provided on all joints to aid in vertical or other motion of the manipulator assembly. Additionally, electronic or electro-mechanical braking can be provided on all joints and at all degrees of freedom. The brake(s) can be configured to default to a locked state so that power is needed to enable any motion. A normally-locked configuration can be provided so that momentary power loss will not cause any unlocking or joint movement. The system can also be designed with sufficient stability to prevent movement, even under minor impacts.

Referring to FIGS. 1, 15a-19d, an embodiment of robotic catheter system 10 can include a user input device 1000. In an embodiment, the user input device 1000 can be a two or three dimensional input device that can be used to spatially manipulate a displayed catheter or a displayed target. Such an interface can be akin to, for example, a traditional computer mouse, a flight joystick, a three dimensional joystick, a 3D mouse, such as those commercially available from 3Dconnexion, a Falcon joystick from Novint Technologies Inc., a touch-screen monitor, or a spatially detected stylus. In an alternative embodiment, the interface device can allow a user to provide input to the system in a manner mimicking traditional catheter handle controls.

Figure 15A:
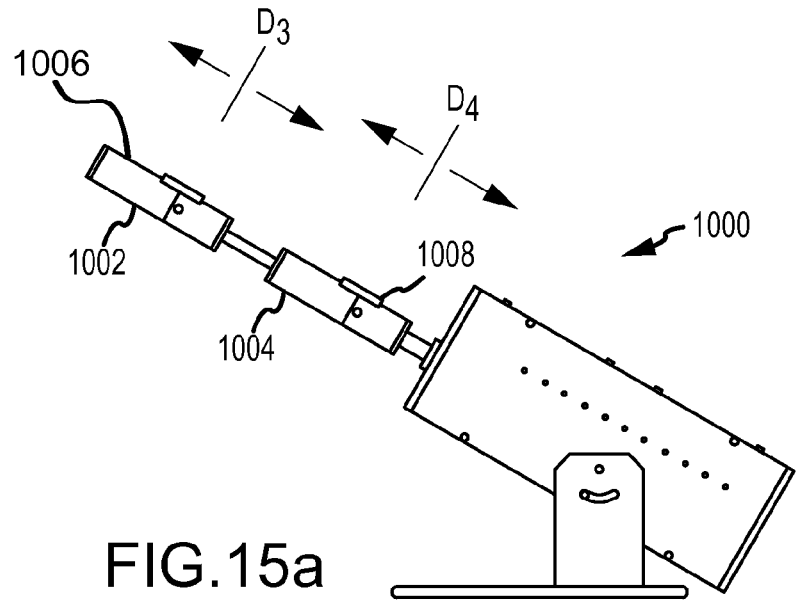
FIGS. 15a and 15b are exemplary joysticks usable with the robotic catheter system of FIG. 1.
Figure 15B:
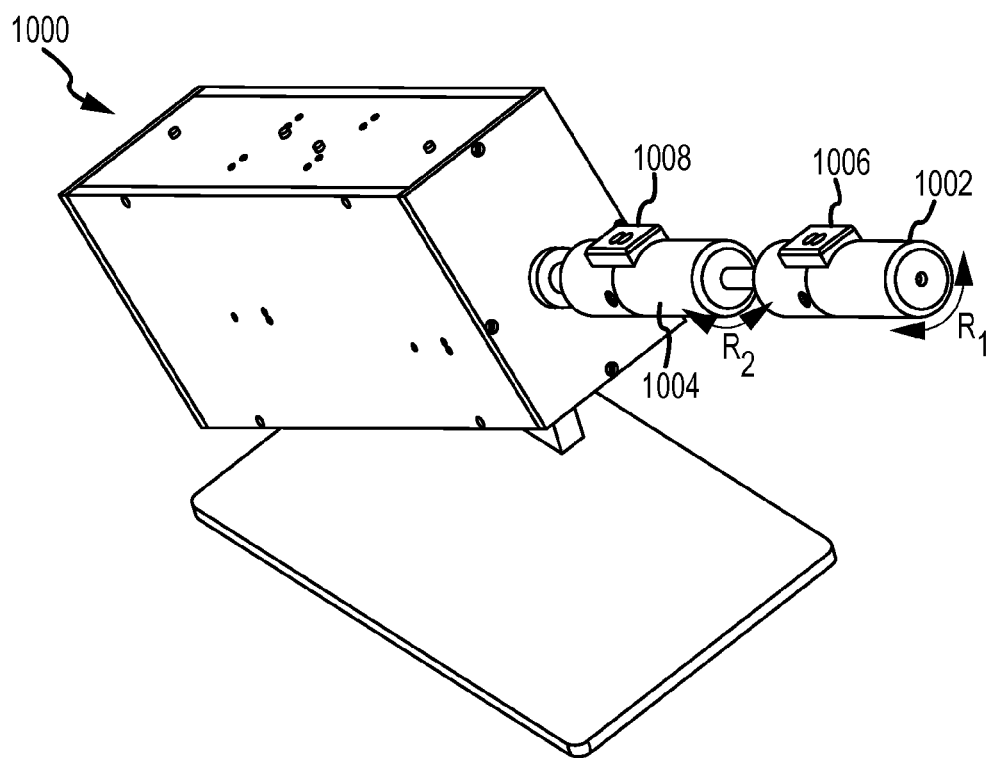

As generally shown in FIGS. 15a and 15b, an embodiment of the user input device 1000 can provide instrumented sheath and catheter handles 1002, 1004 (or vice-versa), respectively, that are able to longitudinally translate (e.g., in directions $D_3$ and $D_4$), independently rotate (in directions $R_1$ and $R_2$), and/or include one or more movable thumb tabs (e.g., elements 1006, 1008). To record the user's input, each degree of movement can be instrumented, for example, with a potentiometer or motor/encoder.

Mimicking traditional, manual catheter control, an embodiment of robotic catheter system 10 can be configured such that longitudinally translating the input handle can cause a respective longitudinal translation of the catheter/sheath distal tip. However, unlike the traditional, manual catheter, the automated catheter system would generally effectuate this translation by advancing or retracting the cartridge. Further, robotic catheter system 10 can be configured so that the rotation of either handle causes a virtual rotation of the catheter/sheath tip, and movement of a thumb tab causes a deflection in the current deflection plane.

In an embodiment of user interface device 1000, any or all motion controls of the device can be associated with/employ a spring centering feature that returns each control element to a set or "home" location after the element is released. Such a centering feature can allow for highly precise movement corrections of the distal tip by registering various input movements as incremental movement from the "home" location rather than by registering movement entirely in absolute terms.

In an embodiment, instead of thumb tab-type controls, user interface device 1000 can additionally include or substitute displacement dial controls. Furthermore, to suit the desires of the user, an embodiment of such a user interface device can permit the handles to be fully interchangeable so that various combinations of controls (e.g., dial and thumb tab handles) can be used for catheter/sheath input. In another embodiment, user interface device 1000 can further include safety buttons (e.g. "dead-man switches") that could be pressed for any joystick movement to be registered by the system. This design would prevent inadvertent motion from affecting the position of the actual catheter tip. In yet another embodiment, user interface device 1000 can further include a virtual reality surgical system, wherein the physician could be positioned within a cardiac environment (see FIG. 1), and physically position the catheter where desired or needed.

Figure 16A:
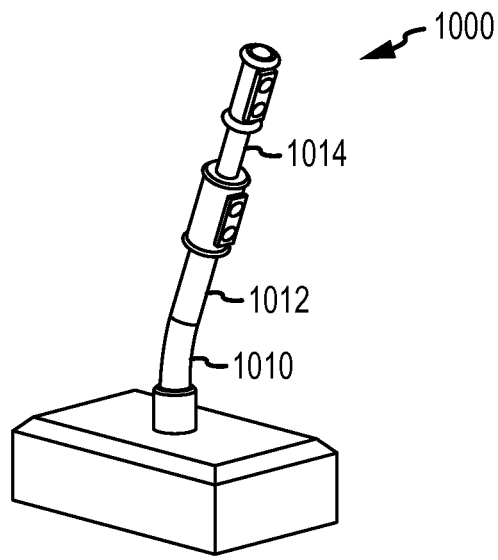
FIGS. 16a-16e are views of an exemplary construction of the joysticks of FIGS. 14a and 14b.
Figure 16B:
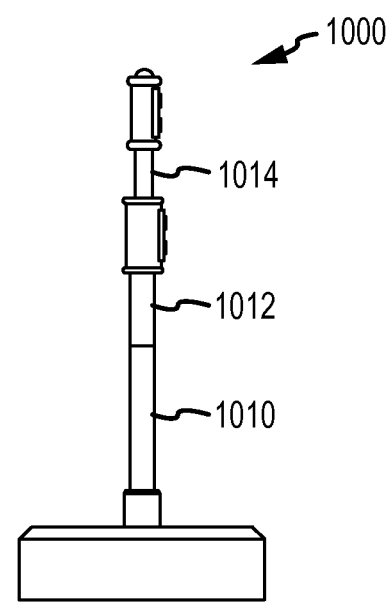
Figure 16C:
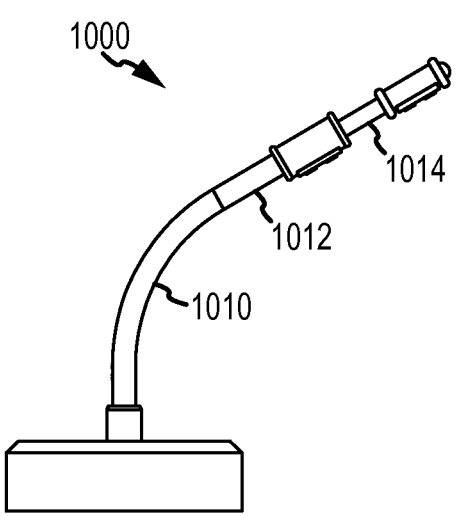
Figure 16D:
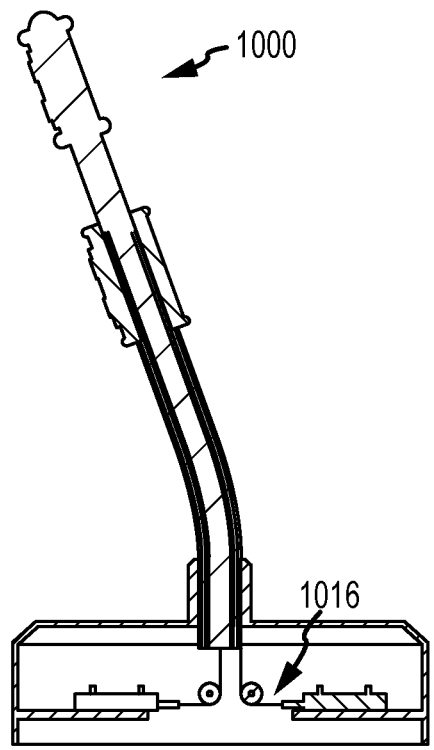
Figure 16E:
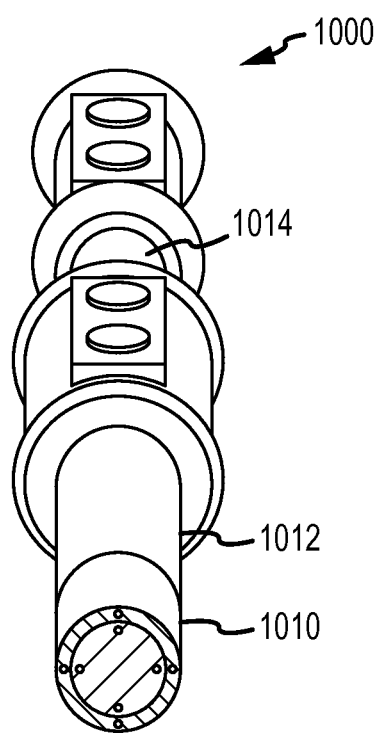

As generally shown in FIGS. 16a-16e, the physical construction of another embodiment of the user interface device 1000 can be similar to that of an actual catheter, though on a different scale. As shown in FIGS. 16d and 16e, by way of example, the various sections can be constructed with pull wires, wire ducts, and variable stiffness sections 1010, 1012, 1014 associated with a conventional catheter. In an embodiment, all motions of this device can be configured with a centering feature (e.g., a spring centering mechanism 1016), wherein the device inherently returns to an initial position when released. This configuration can be useful or suitable for an incremental input control scheme.

In other embodiments, the device can be constructed without a centering mechanism, where the absolute position of the device might instead be used to control the absolute position of the actual sheath and catheter. With such an absolute approach, the input device's physical limitations can be designed to mimic an actual catheter's and sheath's physical limitations (e.g., movement restrictions based on bend radius, catheter retracted into sheath, etc.).

To record user input, each degree of movement can generally be instrumented with either a potentiometer or motor/encoder. If a motor/encoder is used, the system can also provide haptic feedback upon certain events—such as a "feel" if the catheter were to contact a virtual wall. An embodiment of this invention can also include an ablation activation button on the distal end of the device.

Figure 17A:
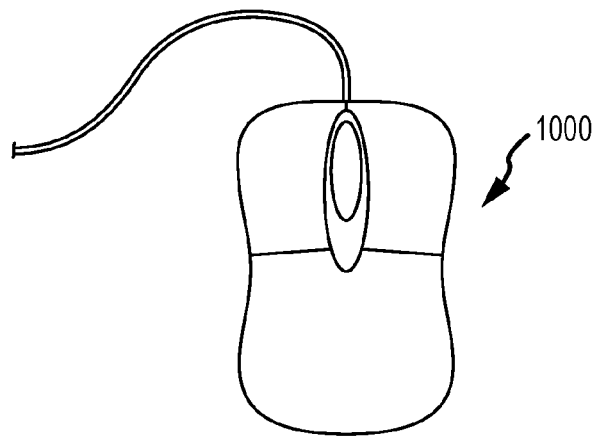
FIG. 17a is an exemplary two dimensional input device usable with a robotic catheter system.
Figure 17B:
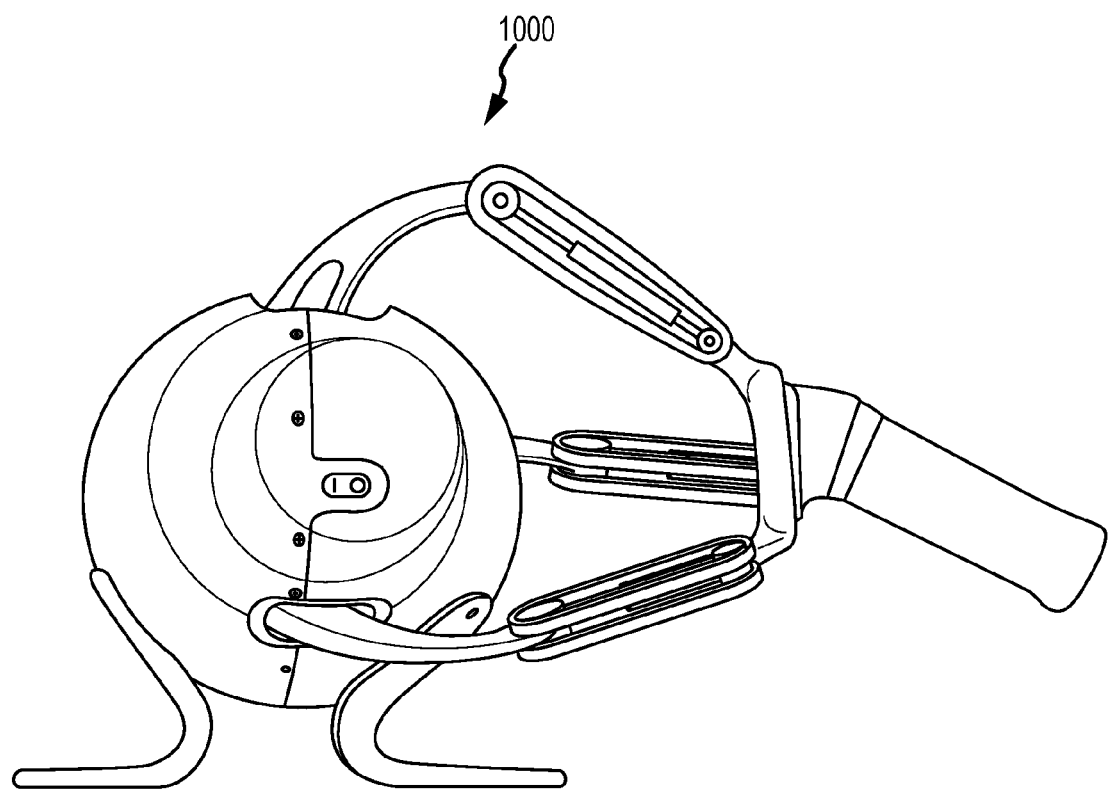
FIG. 17b is an exemplary three dimensional input device usable with a robotic catheter system.

As generally illustrated in FIGS. 17a, 17b, in an embodiment, the user input device 1000 can include a 2D or 3D input device, such as a mouse or 3D joystick. In another embodiment, the user input device 1000 can include a spatially detected glove or stylus as generally illustrated in FIGS. 18a-18b.

Figure 18A:
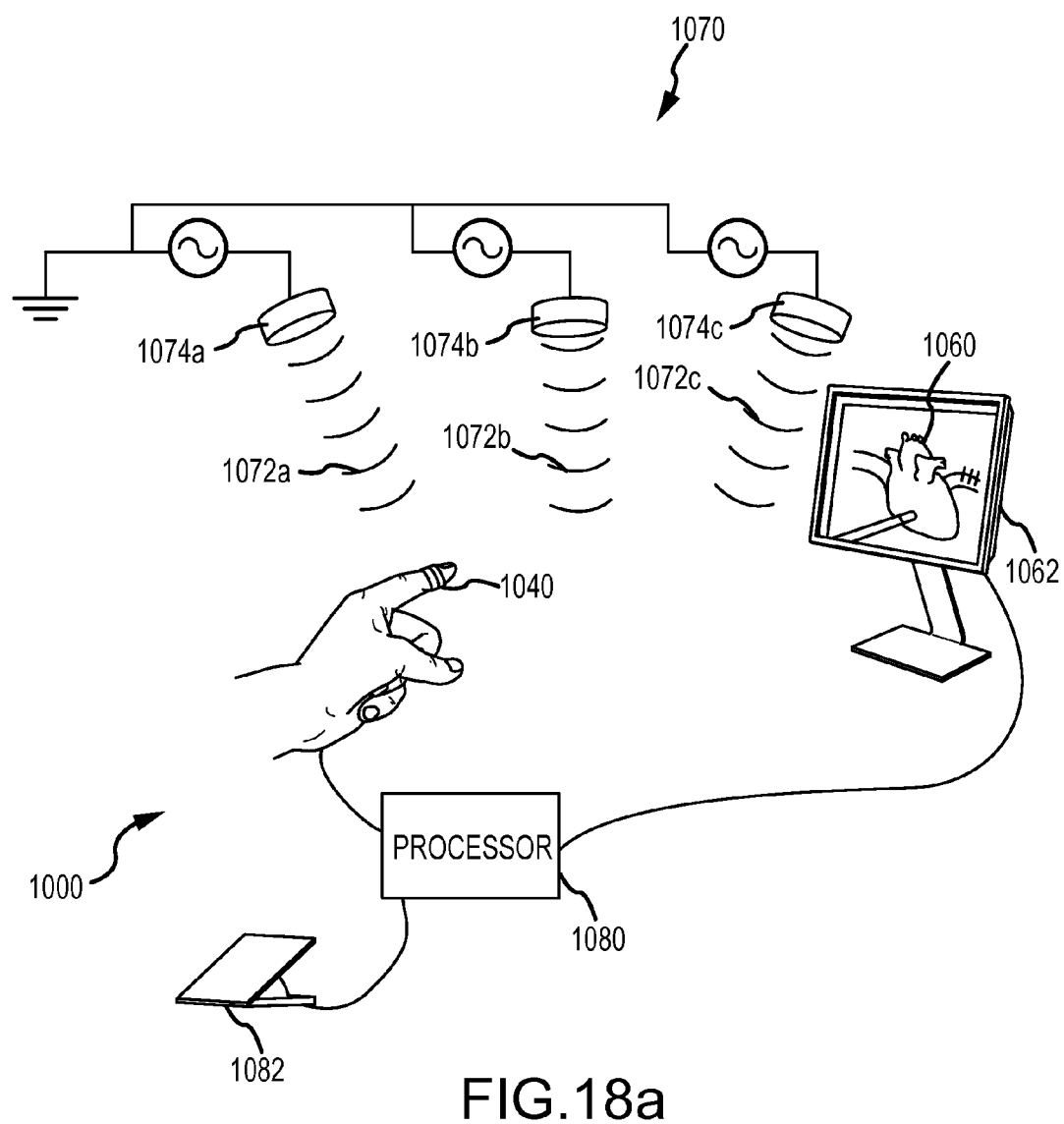
FIGS. 18a-18b are exemplary illustrations of a three dimensional input device usable with a robotic catheter system that employ non-contact position sensing.
Figure 18B:
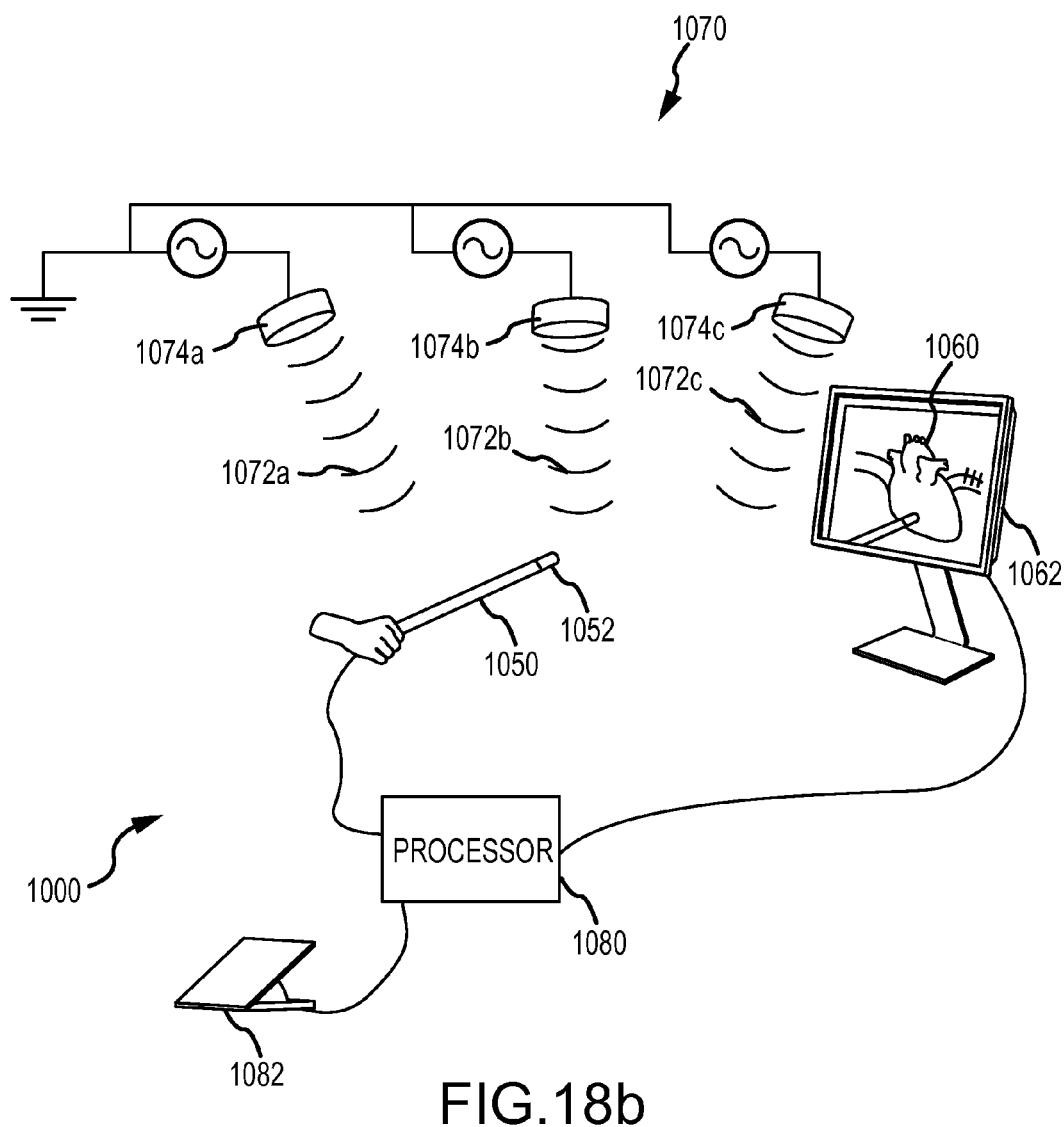

In an embodiment where the user input device 1000 includes a spatially detected glove, such as generally illustrated in FIG. 18a, the user's/wearer's index finger can be instrumented with various sensors 1040 (e.g., position and orientation sensors, and/or accelerometers). In this embodiment, the user can have the ability to manipulate the actual catheter tip by moving his/her instrumented finger. In another embodiment, as generally illustrated in FIG. 18b, a stylus 1050 can be substituted for the user's index finger, where the stylus 1050 is similarly instrumented with sensors 1052 configured to measure, for example, position, orientation, and/or acceleration.

In an embodiment, the user can be presented with a three dimensional visualization of the catheter and/or heart anatomy, such as through holographic imagery. Using the spatially detectable stylus or glove, the user can manipulate or interact with a visualization of the catheter, for instance, by moving the actual device within the holographic image. In such an embodiment, the real-time catheter position can be configured to track the three dimensional position of the user's index finger or stylus. Alternatively, as illustrated in FIGS. 18a-18b, the spatial positioning of the glove 1040 or stylus 1050 can be detected in three dimensional space and registered to a representation of a catheter or a target located within a model of the patient's anatomy 1060. The catheter representation within the model 1060 can be configured to be displayed to the user on a two-dimensional monitor 1062. By moving the instrumented finger or stylus, the user can control the movement of the catheter representation, which is in turn configured to control the movement of the actual catheter. Further, if desired, an incremental movement control scheme can be implemented by incorporating an activation switch, such as, for example, a foot pedal 1082. The actuation switch can indicate to the system that successive movements should be recorded or registered within the system for the purpose of control.

The glove or stylus input device can be locatable in 3-D space through the use of a positioning system employing a magnetic field, an electrostatic field, or through the use of an optical positioning system. These systems can include, for example, the EnSite NavX system from St. Jude Medical, the gMPS system from Mediguide, the CARTO system from Biosense Webster, the Aurora system from Northern Digital, or the RMT system from Boston Scientific.

In an embodiment, the positioning system can be implemented within a liquid tank (e.g., water tank), where field generators (such as those associated with the St. Jude Medical NavX™ control system) are externally attached. For such embodiments, an instrumented glove or stylus can extend into the tank while, for example, user's finger (e.g., index finger), or stylus can be instrumented with electrodes configured to measure parameters of the electric field. In an embodiment, the construction and/or placement of the sensors (e.g., NavX-type electrodes) can be similar to sensors on the distal portion of the catheter.

In another embodiment, the positioning system can be implemented using a magnetic positioning system. As generally illustrated in FIGS. 18a-18b, a magnetic positioning system 1070 can operate, for example, by emitting several magnetic fields 1072a-1074c from an array of field generators 1074a-1074c. Sensor coils (e.g., sensors 1040 or 1052) located on the glove or stylus can then sense the magnetic field strength emanating from each sensor coil. By selectively energizing each field generator at a different time or frequency, a processor 1080 can be able to resolve the sensor's position and orientation relative to each field generator or to a fixed reference sensor. Detected changes in the position and orientation of the glove or stylus sensor can then be registered and scaled by the system as a movement of a displayed catheter.

A user interface (UI) (sometimes also referred to herein as a user interface device) that utilizes a touch screen or a multi-touch display will now be described with reference to FIGS. 19a-19i. Before proceeding to the detailed description of various embodiments, however, a brief overview of touch screen technologies and associated challenges will be set forth.

Figure 19A:
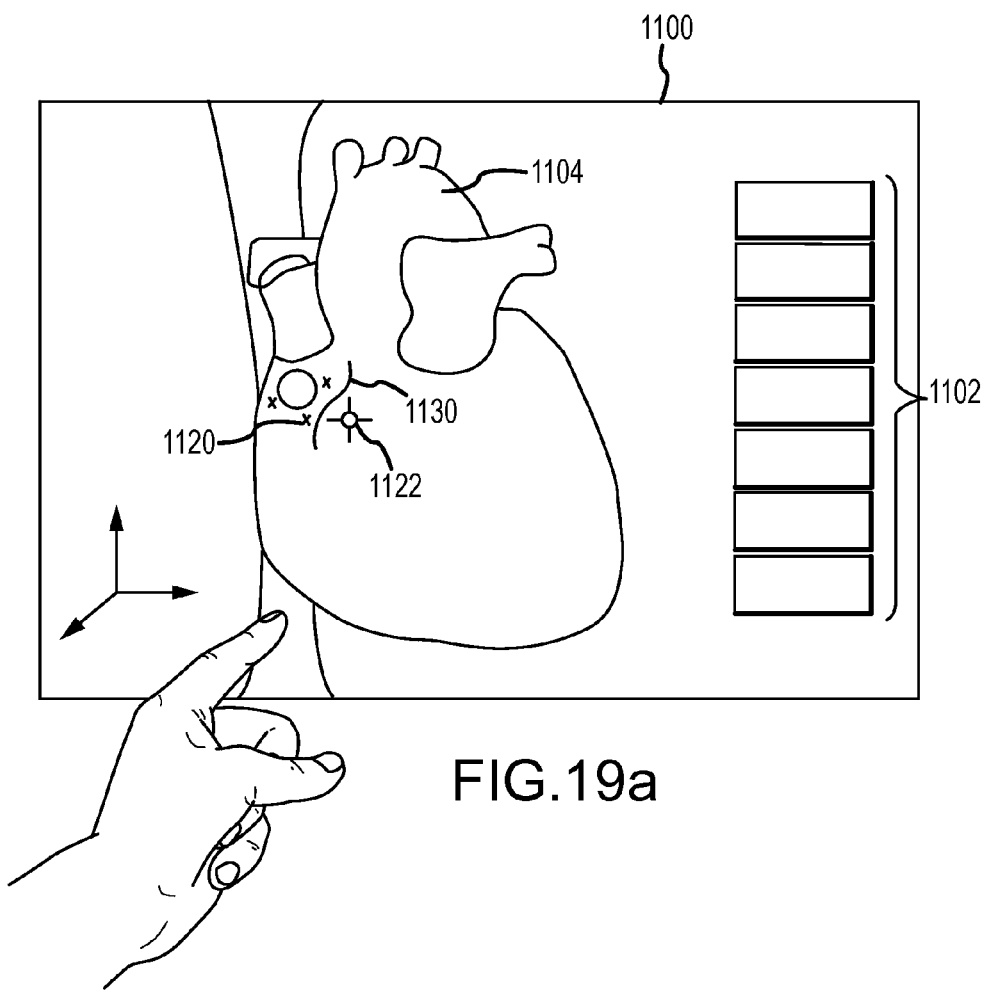
FIGS. 19a-19c are exemplary embodiments of a touch-sensitive input device usable with a robotic catheter system.

FIG. 19a is a simplified plan view of an exemplary user interface. An embodiment of user interface device can include a touch or contact responsive display, such as included in a touch screen display interface or a multi-touch display interface 1100 (as in FIG. 19a) and related hardware and software that can allow a user to physically interact with the robotic catheter system without the need for a keyboard, mouse, or other additional input device—though additional input devices can be used in conjunction with a multi-touch display interface. Such a display can be configured to recognize multiple finger or hand contacts with or along the screen, and can allow a user to directly interface with the objects, anatomy, or devices displayed on the screen. In this regard the entire contents of issued U.S. Pat. No. 5,825,352 to Bisset, et al. entitled, "Multiple fingers contact sensing method for emulating mouse buttons and mouse operations on a touch sensor pad" are hereby incorporated in their entirety as if fully set forth herein.

Many different types of so-called "touch screens" can be utilized to perform a surgical operation according to this disclosure, including resistive-type (e.g., displays having several layers including two thin metallic and electrically conductive spaced-apart layers acting like a pair of voltage dividers), surface acoustic wave (SAW)-type (e.g., displays having ultrasonic waves passing over the display surface), capacitive-type (e.g., displays having an insulator and a transparent conductive coating such that when a conductor, such as a human hand, a magnet, or active metallic element, touches the screen it changes the capacitance at the site of contact) which include surface capacitance-type displays in which the conductive coating or layer has an electrical voltage imposed upon it and the conductor forms a dynamic capacitor upon contact. Capacitive-type displays also include projected capacitance-type (PCT) displays in which the conductive layer is etched to form a grid pattern or perpendicular patterns, thus creating a grid of discrete capacitive elements (the latter of which is particularly suited for multi-touch operation(s)). Other types of display technology usable according to this disclosure include strain gauge (also known as force panel technology, or FPT), in which the FPT display screen is spring-mounted and the gauges determine deflection when the screen is touched. One advantage of FPT is that the magnitude of force applied to the screen is measured (in the Z-axis) and thus can be used. An FPT or other display also can indirectly measure (or approximate) the magnitude of contact by a relatively malleable or deformable instrument (including a human digit) by measuring the rate of change of the contact surface or "patch" (e.g., from a relatively small area to a relatively larger or growing area and vice versa). Another touch screen type usable with the present disclosure is optical imaging, wherein two or more image sensors (e.g., two pairs of opposing cameras) are placed around the edges of a display screen and the display is backlit, such that contact appears as a shadow. Each pair of cameras triangulates the shadow to locate the position of the contact. Another technology is dispersive signal technology (DST) in which the mechanical energy imparted to a glass display screen is detected upon contact, but ongoing stationary contact is not detected. Thus, DST technology can be readily applied for dynamic or continuously-moving control of a catheter displayed upon a glass display screen. Yet another technology more recently introduced involves acoustic pulse recognition (APR) technology wherein two or more piezoelectric transducers translate mechanical energy of contact (vibration) into an electronic signal. As with DST, APR technology does not detect ongoing stationary contact.

One potential negative effect of using a touch screen display (or multi-touch display) to control a cardiac catheter in three dimensional space via a two-dimensional display screen (translated and registered in 3D space with a computerized visualization system) for a four-dimensional (4D)

procedure (i.e., 3D space plus time) relates to undesirable inadvertent or inaccurate contact with the control surface (i.e., the touch screen). As described hereinafter, the inventors have substantially ameliorated this effect with a variety of safety features and capabilities. For example, a variable or fixed degree of temporal latency can be implemented such that an operator could essentially retract or retrace an input desired catheter motion. In addition or alternatively, the system can include a safety switch, movement activation switch, or another device or feature configured to interrupt physical movement effected by the system. The safety switch can have a default "off" status and require an affirmative input before catheter motion can occur, or the safety switch can have a default "on" status and require affirmative input to disable catheter movement. The safety switch can be a separate device from the touch screen (e.g., a foot pedal, a force sensor disposed on a handle or a seat and the like). Alternatively or additionally, the safety switch can be an input or button displayed in a prominent location on the touch screen. Alternatively or additionally, an acoustic sensor can be coupled to the control system with a sound recognition capability to, for example, stop, slow, or change the mechanical motion of a catheter or other medical device upon the detection of a predetermined sound or sounds. Alternatively or additionally, the control system can also include a means for suppressing recognition of a touch-based input when predetermined criteria indicative of an inadvertent, incorrect, or too rapid touch are satisfied. The criteria can include, for example, a dynamic or changing area of contact or other criteria known in the art. The means can also be responsive to actuation of another safety switch in the system.

Figure 19B:
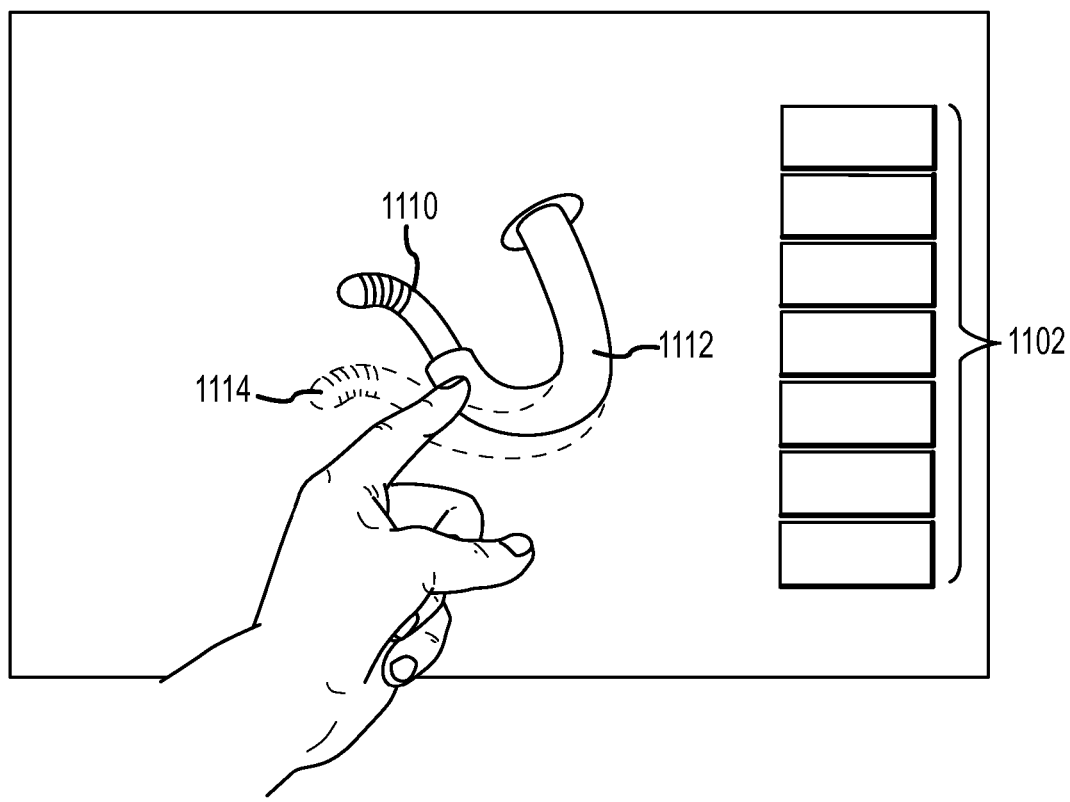

As shown in FIG. 19a-19b, an embodiment of the multi-touch interface 1100 can include multiple on-screen menu buttons 1102 that allow a user to toggle between various active functions (or modes) within the image by simply tapping, touching, and/or dragging a digit, stylus, or pen (e.g., a magnetically- or optically-active pen or pointer) on a desired location or button 1102 or scroll-down menu (not specifically depicted in FIG. 19a) or the like displayed on the interface 1100. Such functions can include, for example, the ability to pan, rotate, or enlarge or reduce in size (e.g., "zoom") 3D objects and models within the display, select and/or direct movement of the catheter or sheath, place lesion markers, waypoints, virtual sensors, or automated movement targets and lines within the anatomic model.

In an exemplary approach, when in rotate mode, a user can rotate a 3D cardiac geometry 1104 by touching the screen with a finger and dragging across the screen to spin the 3D model about an axis orthogonal to both the surface normal of the screen and the direction of the dragging motion. When in pan mode, a dragging motion across the screen can move the model across the screen. Additionally, the zoom can be controlled, for example, through a pinching (zoom out) or expanding motion (zoom in) of multiple fingers, or through the use of an on-screen slider.

As shown in FIG. 19b, in an embodiment, the multi-touch interface 1100 can be used to control the movement of a displayed catheter 1110 or sheath 1112 by entering a desired movement via one or more touch-based inputs. For example, the displayed catheter 1110 or sheath 1112 can be moved by first pressing on the image of the catheter or sheath to select it, followed by dragging the selected device in the direction of intended travel. Alternatively, the catheter 1110 or sheath 1112 can be selected by using a pinching motion as if the user is virtually grabbing the image. In an embodiment, while the user is dragging a virtual representation of the catheter or sheath, a ghost image 1114 of the current position of the device can be displayed as a reference. The ghost image 1114 can be based on real-time feedback of the actual catheter position as provided by a catheter positioning system such as Ensite NavX™. In an alternate embodiment, the ghost image 1114 can be the target position to which the virtual representation of the catheter or sheath is dragged. Once the user is satisfied with the movement, the user can release the selected catheter or sheath by removing his/her finger from the screen. The system can then be configured to then move the actual catheter in accordance with the user intended motion (subject to a safety switch), and can update the ghost image 1114 to reflect the actual movement. In another embodiment, the user can move a control point on the catheter or sheath and the actual catheter can be configured to track this point in real-time.

Figure 19C:
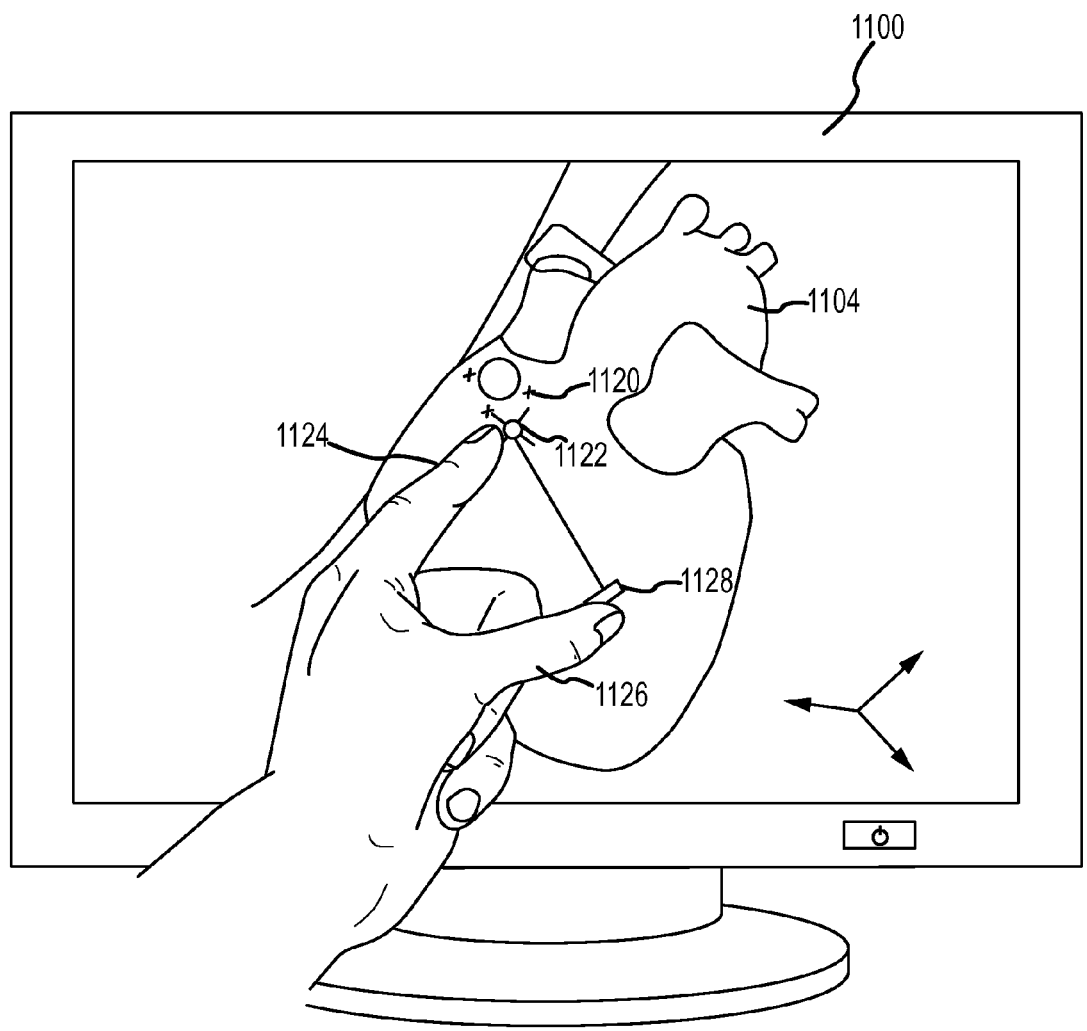

In an embodiment, as generally illustrated in FIG. 19a, 19c, the user can use the multi-touch interface 1100 to select target points 1120 within the image. These target points can be used to identify lesion points for intended or completed therapy delivery, waypoints for semi-automated step-wise catheter movement, destination points for fully automated movement, or as relative markers or virtual electrophysiology sensors that can have no impact on relative movement. In an embodiment, a target point can 1120 be initially set by tapping on the touch screen in a position where a target point is desired. Once a point has been set, it can be subsequently selected by re-tapping on the point. When a point is "selected," it can change appearance, such as selected point 1122. If the user desires to move target point, the user can for example, select it by tapping it, and then drag the point to a new location. Additionally, after selecting a point, the software can call up a list of menu options that can allow the user to configure or view one or more parameters of the point. Such parameters can include, for example, the nature of the point (e.g. marker, lesion point, waypoint, sensor) the distance of the point above the surface, or specific data recorded or computed at the point.

Once a user taps the screen in the desired location of the target point, the software can be configured to place the target point 1120 directly on the surface of the model 1104 as displayed ("surface target point"). In such a configuration, the system can know the relative depth of each pixel or primitive on the display. By touching on a displayed element, the system can map the target point directly to the anatomical surface. The software can further allow the user to specify a fixed or minimum distance from the displayed anatomical surface where the point should be located. or example, if the user specifies a distance of 10 mm prior to selecting a point, the software can locate the target point 10 mm off of the selected surface in a direction normal to the screen/viewing plane. Alternatively, the software can generate a virtual surface located 10 mm interior to the surface of the anatomical model and then map the point to the virtual surface. (i.e. 10 mm normal to the anatomical model surface). In another embodiment, as shown in FIG. 19c, the user can select a point 1122 with one finger 1124, and use a second finger 1126 to control a variable slider 1128 to specify a distance above the surface. The slider 1128 can likewise be located on the side of the screen and/or can appear only after a point has been selected. The display can also be configured to display a secondary projection of the catheter and model to aid the user in positioning the target point in three dimensional space ("3D target point") (e.g., using a right anterior oblique (RAO) projection as the primary display, and a left anterior oblique (LAO) projection as the secondary display). The multiple views displayed on the display can be orthogonal to each another, or can be views at other angles relative to each other.

In an embodiment, different symbols, or glyphs, can be used to represent surface target points, 3D target points, and dragging control points. In addition, the color of a symbol can change to illustrate the status of the catheter relative to the intended movement represented by the symbol. For example, a target point or dragging control point can be blue when placed, yellow when the catheter is being physically moved to the point, and green when the movement associated with the point is successfully completed. The point can be red if the movement associated with the point could not be successfully completed.

Referring back to FIG. 19b, in an embodiment, as the user is dragging an image or representation of the catheter 1110 (or sheath 1112), the user can use a second finger to modulate a slider (such as a slider generally illustrated in FIG. 19c) to control the catheter's distance from the anatomical surface in real time. Using this technique, the user could achieve a motion where, for example, the catheter begins in contact with the tissue, gradually lifts off from the tissue while traversing a distance, and gradually lands back on the tissue. Alternatively, for either free catheter motion, or for positioning a target point, the user can use a physical slider or wheel, apart from the display, to modulate the distance from the surface. Using the touch screen, the user can also control the extension of the catheter from the sheath by placing one finger on the catheter 1112 and a second finger on the sheath 1114 and expanding or squeezing his/her fingers together.

In addition to setting individual target points, as illustrated in FIG. 19a, the user can also specify a line or path 1130 along the surface of the model 1104 by touching and dragging a finger across the screen. Such generated line 1130 can be similar to a splined series of waypoints. Furthermore, in an embodiment, the user can select a point along the line and "lift" that point away from the surface by, for example, using a slider or numerical input. Points adjacent to the selected point can additionally be lifted off as if they were tied to the selected point.

Figure 19D:
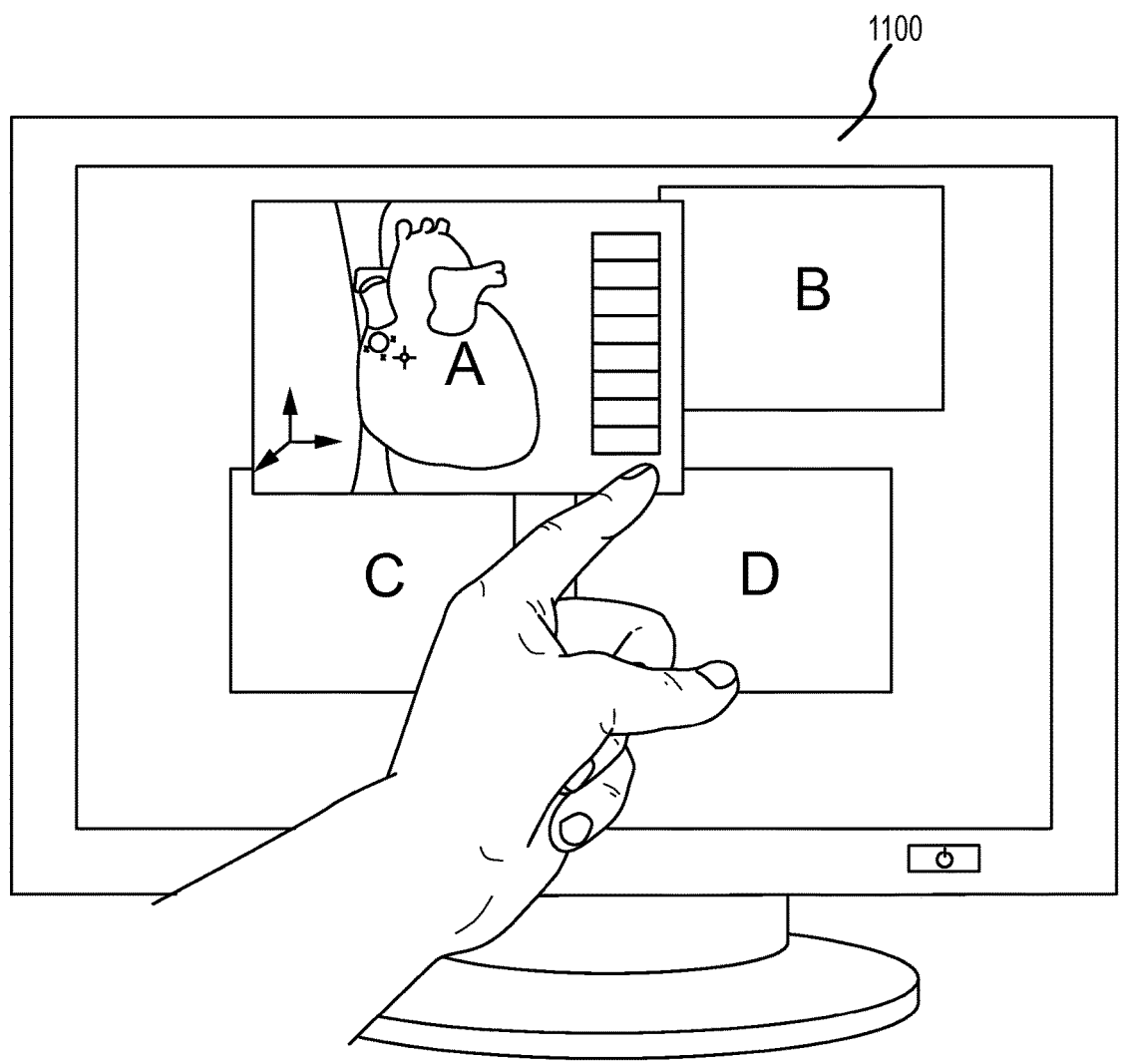
FIG. 19d is an embodiment of a touch-sensitive input device used to manage multiple displays.

In an embodiment, as shown in FIG. 19d, the multi-touch interface 1100 can be used to manage multiple displays (such as displays A-D) in an integrated electrophysiology environment. Using the interface for display management purposes can include the ability to resize, move, minimize, or maximize windows that display, for example, EnSite NavX models, digital fluoroscopic displays, patient vital information, patient hospital records, real time electrocardiograph traces, CT imagery, MRI imagery, and/or any other displays desired by the user. In an embodiment, a user can move or expand a window using on-screen buttons to, for example, freeze the touch screen input for the respective displays, followed by touching and dragging the window to move it, or using a multi-finger expanding motion to, for example, expand the window.

In another embodiment, a multi-touch interface 1100 can be implemented on a separate device from the main display of the system, such as a tablet computer or other touch-screen device, which can have an independent processor. In such an embodiment, the separate input device can display menu buttons 1102 and one or more views of anatomical model 1104 for catheter movement control (i.e., the separate device can display an interface similar to that shown in FIGS. 19a-19b), while the main display can show menu buttons 1102 and model 1104 and additional information and/or additional views of model 1104 and/or show additional windows. The separate input device can also be configured to show multiple windows, as in FIG. 19d, or the main display can be a clone of the separate input device.

In another embodiment, the user input can be obtained through a spatial operating environment that is configured to monitor hand or body gestures without any required direct contact with a screen or device. The interface can operate together with either a two dimensional display or a three dimensional holographic image, and can allow the user to selectively manipulate, for example, the catheter or sheath, the cardiac model, various markers or waypoints within the model, or the positioning of other informational windows or displays. Such a gestural interface can include, for example the "G-Speak" Spatial Operating Environment, developed by Oblong Industries, Inc.

Figure 19E:
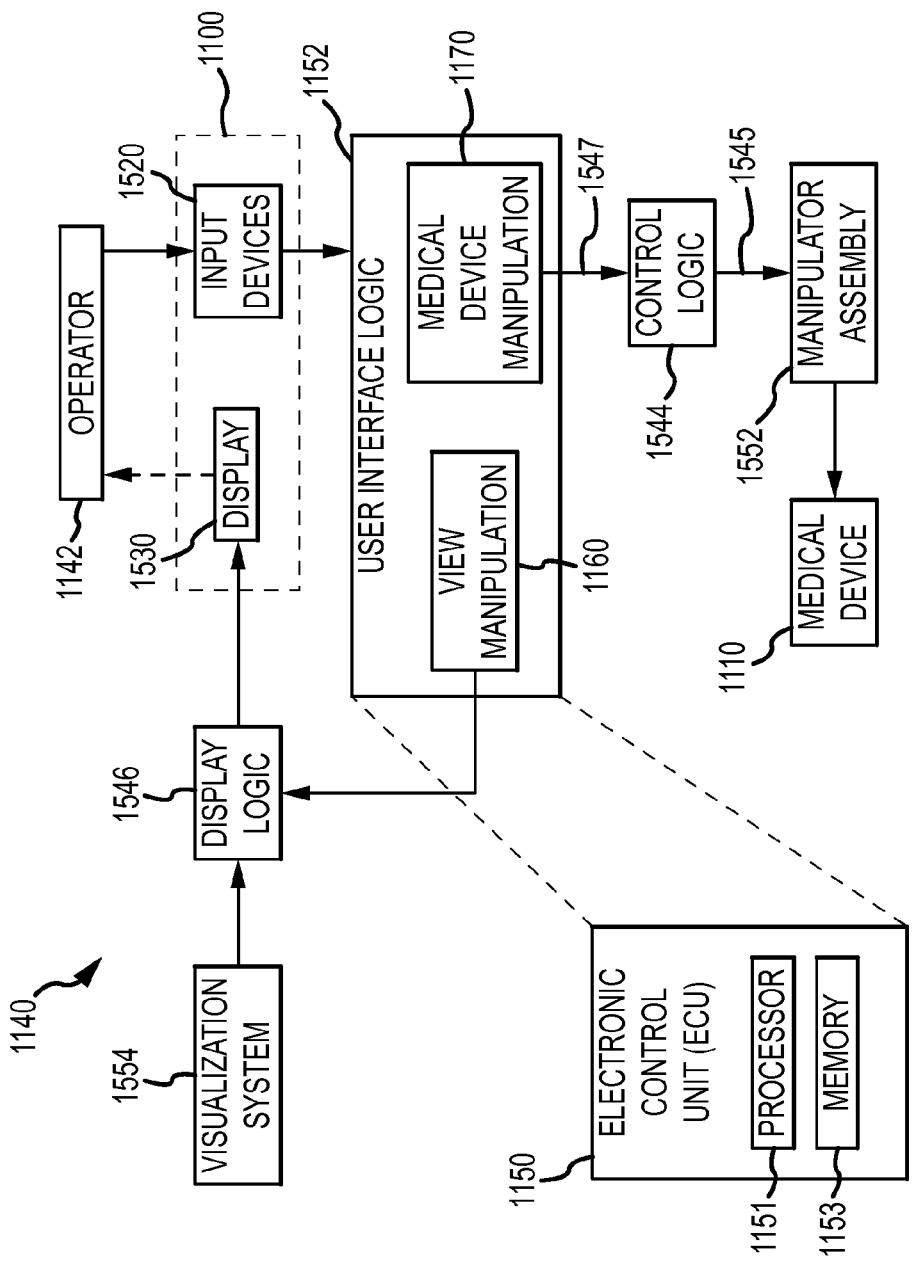

FIG. 19e is a simplified block diagram of a control system 1140 for user-guided robotic control of a medical device 1110 that includes touch screen or multi-touch screen user interface functionality as described herein. Control system 1140 can include the components and features necessary for a user to view the status of the robotic system, input a desired movement of a medical device, and confirm that the robotic system performs the desired movement.

As generally shown in FIG. 19e, an embodiment of control system 1140 for user-guided control of a medical device 1110 includes a programmed electronic control unit (ECU) 1150 having a processor 1151 and a computer readable memory 1153 (or other computer readable media suitable for information storage). The system 1140 further includes a plurality of logic modules to be described below, which in an embodiment can take the form of software stored in memory 1153, configured for execution by the processor 1151. The ECU 1150 can otherwise comprise conventional apparatus known in the art.

System 1140 further includes one or more input devices 1520 with which a user or an operator 1142 can directly interact and one or more displays 1530 which the operator 1142 can view. In an embodiment, the operator or user input function and display function, at least in part, are integrated in a composite device in the form of a touch screen display or multi-touch screen display, which is designated by reference numeral 1100 in FIG. 19e (and enclosed in dashed lines).

Control system 1140 further includes a visualization system 1554, which is configured to provide a view of an anatomical model of a feature of a patient (e.g., the heart or chambers thereof). The visualization system 1554 may comprise the visualization and navigation system described above in connection with FIG. 1. Control system 1140 further includes display logic 1546, which is configured to facilitate communication of the above-mentioned views of the anatomical model to display 1530 or touch screen display 1100. In an embodiment, the display logic 1546 may be incorporated into the visualization system 1554. In other words, the visualization system 1554 and the display logic 1546 are shown separate solely for convenience of description.

With continued reference to FIG. 19e, control system 1140, and the ECU 1150 in particular, is configured with user interface (UI) logic 1152 that is stored in the memory 1151 and configured to be executed by ECU 1150. The UI logic 1152 is configured, generally, to obtain input from input device 1520 or touch screen display 1100 with respect to a view of an anatomical model (as described above).

In addition, control system 1140 includes control logic 1544, which can also be stored in memory for execution by ECU 1150. Control logic 1544 is configured to produce an actuation control signal 1545 to control actuation of one or more manipulator assemblies 1552. The control logic 1544 is configured to produce such an actuation control signal 1545 based at least in part on the signal 1547 from UI logic 1152, and corresponding touch screen input originating with touch screen display 1100. Embodiments of input device(s) 1520, display 1530, control logic 1544, display logic 1546, visualization system 1554, and manipulator assembly 1552 are all described in greater detail in conjunction with FIG. 27. UI logic 1152, control logic 1544 and display logic 1546 can be stored in the memory 1151 of ECU 1150 or elsewhere in the other components of system 1140.

It should be understood that ECU 1150 can be implemented as a part of electronic control system 200, robotic controller 1540 (shown in FIG. 27), or in another computing portion of the system. Furthermore, it should be understood that the functionality of visualization system 1554, ECU 1150, controller 1540, and electronic control system 200 may all be combined into a single apparatus, or may be divided into separate devices.

UI logic 1152 includes a view manipulation block 1160 and a medical device manipulation block 1170, to be described in greater detail below. In this regard, UI logic 1152 obtains input from input device 1520 (i.e., touch screen display 1100 in an embodiment) and is configured to recognize the input as one of multiple types of actions such as, for example: (1) a view manipulation action (as recognized by block 1160), corresponding to the manipulation of a user's view of an anatomical model as shown on display 1530 or (2) a medical device manipulation action (as recognized by block 1170), corresponding to the user's desired or commanded manipulation of the medical device 1110, whose movement is controlled by the robotic system.

Generally, when the input obtained by UI logic 1152 corresponds to the user's manipulation of the displayed view of the anatomical model, block 1160 of UI logic 1152 provides such input to the display logic 1546 to update the display 1530 (i.e., touch screen display 1100) with a new or updated view of the model. On the other hand, when the input obtained by the UI logic 1152 relates to a manipulation (e.g., translation, deflection, virtual rotation) of the medical device 1110, the UI logic 1152 provides such input to control logic 1544, which, as noted above, is configured to produce an appropriate actuation control signal destined for the manipulator assembly 1552, which is adapted to implemented the desired movement of the medical device 1110. To recognize the input, the UI logic 1152, in an embodiment, can determine the origin, magnitude, and direction of an input vector in the coordinate system of the input device.

As described above, in an exemplary embodiment, input device 1520 and display 1530 can be integrated into a composite device. In the exemplary embodiment, the UI logic 1152 is configured to obtain input from the touch screen display corresponding to a variety of user actions. For example, some possible user actions include: designation of a targeted lesion location on the touch screen display (relative to the model view); selection of one of a plurality of menu items from (i) a drop-down menu and (ii) a list of menu items; enlargement or reduction of a portion of a displayed structure of the model view; adjustment (e.g. pan) of a portion of a displayed image (i.e., the model view); activation of a replay feature of a stored, temporally varying physiologic parameter; activation of a replay of a stored video clip (e.g., of a part of a procedure); rotation of a view of an anatomical model; change one or more display attributes, including color and screen location; and, where the medical device includes at least a catheter and a sheath, selection of one or more of the catheter and the sheath for navigation and/or manipulation purposes.

Figure 19F:
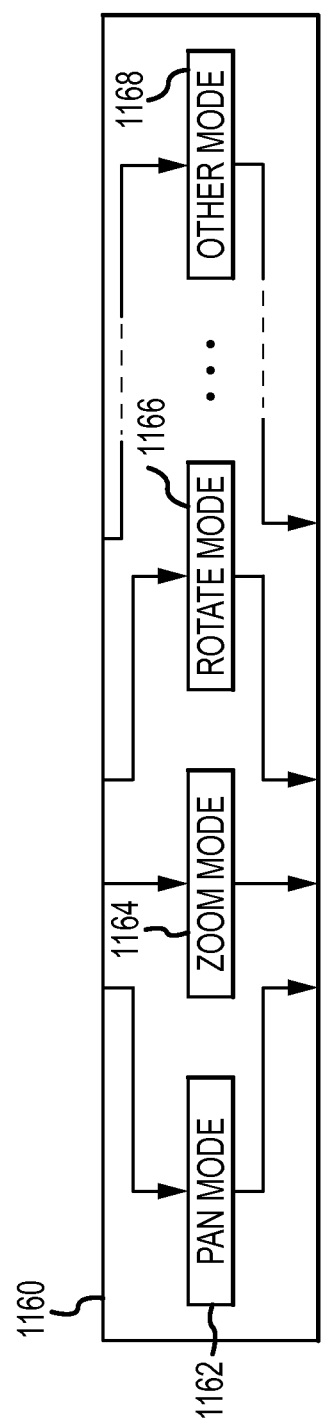

FIG. 19*f* is block diagram showing, in greater detail, the view manipulation block 1160 of FIG. 19*e*. Block 1160 includes various functionality, consistent with the overall need of UI logic 1152 to obtain and recognize input indicative of several different modes of anatomical model view manipulation. It should be understood that FIG. 19*f* shows exemplary modes available when the UI logic 1152 is operating in the view manipulation mode. The view manipulation mode may be entered by virtue of a specific user instruction (i.e., a screen button for that purpose), or may be implicit by the nature of the touch or multi-touch (i.e., a finger swipe can be interpreted as a pan command in all operating modes of the UI logic 1152). In this regard, then, possible particular modes include a pan mode 1162, where the UI logic interprets a user touch input for purposes of translational movement of the model view across the screen, a zoom mode 1164, where the UI logic interprets the user touch input for purposes of enlarging and/or shrinking a view of the model, and a rotate mode 1166, where the UI logic interprets a user touch input for purposes of rotating the view of the model about an axis. View manipulation 1160 can have multiple, other modes of operation, represented by other mode 1168. Regardless of the mode, either the user interface logic 1152 or the display logic 1546 can relate the input to the display coordinate system to determine the appropriate modification of the model view.

FIG. 19*g* is a block diagram showing, in greater detail, the medical device manipulation block 1170. The user interface logic 1152 can be configured to obtain and recognize user touch input as calling for several different modes of medical device manipulation. A first mode, designated control point drag mode 1172, can result in user-guided movement of the medical device substantially as described herein in conjunction with FIG. 19*b* (i.e., dragging a catheter across a display with a mouse or a touch-based motion on a touch screen). Control point drag mode 1172 can have multiple operating modes such as, for example, translation and deflection (full control), translation-only, or deflection-only. In translation-only mode and deflection-only mode, the control logic 1544 constrains usage of the available robotic movements of manipulator assembly 1552 to only translation movements (in translation-only mode) or deflection movements (in deflection-only mode). The manipulator assembly 1552 would therefore be configured to use deflection-only movement or translation-only movement to bring the catheter as close as possible to the desired position indicated by user input. Such an embodiment can find use when the user wishes to form a particular shape of the catheter that the controller 1520 would not necessarily form in an embodiment of the control scheme in which the control logic 1544 employs all degrees of freedom available in the robotic system (i.e., translation and deflection).

A second mode, designated target point mode 1174, can result in user-guided movement of the medical device substantially as described herein in conjunction with FIG. 19*c* (i.e., designating target points and allowing the system to determine a path to or through the target points). Target point mode can have multiple operating modes such as, for example, 3D target point placement and surface target point placement. The number of medical device manipulation modes can be expanded as needed, indicated by mode 1176. The user interface logic 1152 can be configured to obtain user-specified parameters for each additional mode. Control point drag mode 1172, target point mode 1174, and other modes 1176 can also be utilized in conjunction with multiple input devices, such as, for example, a touch screen display or mouse 1000.

Figure 19H:
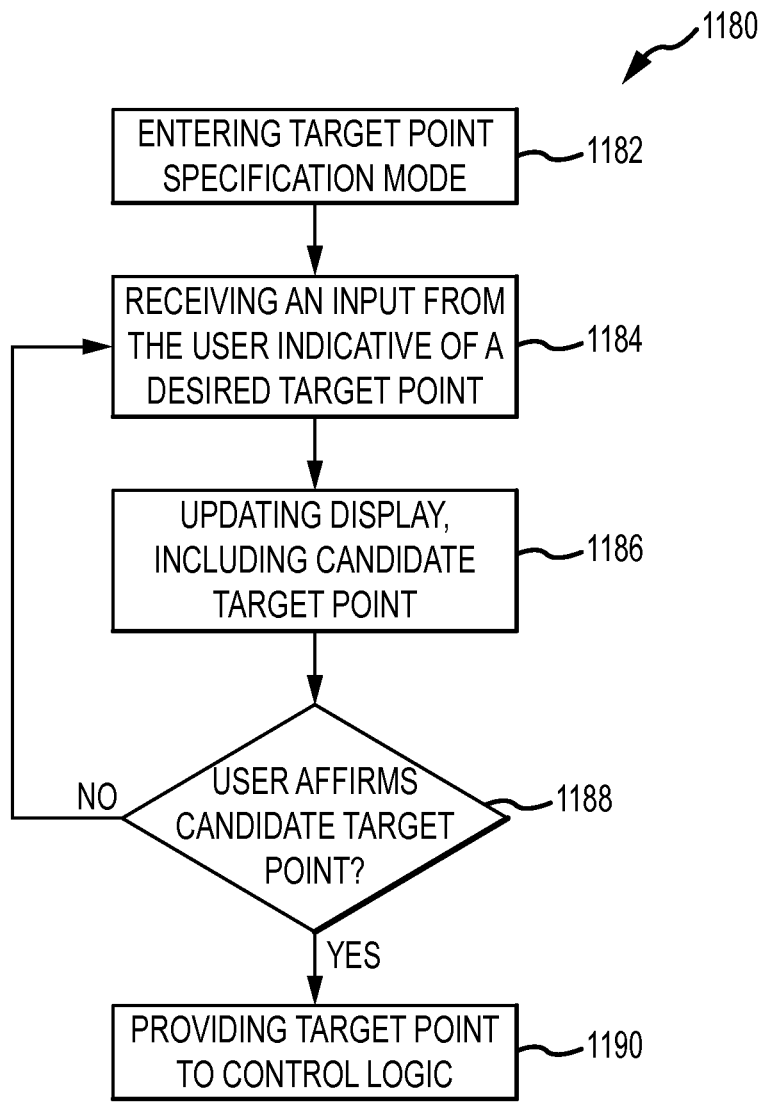
FIG. 19h is a flow chart of a method of operation of the control system depicted in FIGS. 19e-g.

FIG. 19h is flowchart showing an exemplary method (designated method 1180) of specifying a desired target point, for example, for use in an automated catheter movement procedure, using some of the features of the UI logic 1152 described herein. The method begins at step 1182 with the UI logic 1152 entering a mode where the user or operator can specify the target point through an input device 1520 (e.g., a touch screen or mouse). The method proceeds to step 1184.

At step 1184, UI logic 1152 obtains an input from the user or operator 1142 indicative of a desired target point. In one embodiment, the user may enter the desired target point through input device 1520 by, for example, clicking a mouse at a particular display location or tapping a touch screen at a particular location. In an embodiment, upon the initial "click" or "tap", the UI logic 1152 interprets such input in light of the current catheter position (i.e., the current catheter position, in a three-dimensional reference coordinate system, becomes the initial candidate target point, also in the 3D reference coordinate system). In another embodiment in which input devices 1520 include a touch screen, UI logic 1152 can be configured to recognize certain cues, or gestures, made on or in proximity to the touch screen. Based on the input cue and the active mode, or function, of UI logic 1152, logic 1152 can associate the cue with a user's desired input through the use of a pre-defined lookup table. The method proceeds to step 1186.

At step 1186, the UI logic 1152 updates the display, including a representation of the candidate target point, by prompting display logic 1546 to provide a new view of the anatomical model. In this regard, the UI logic 1152 and display logic 1546 are configured to display the candidate target point as the user input changes (i.e., as the user moves the mouse around or as the user moves his finger around on the touch screen).

Figure 19I:
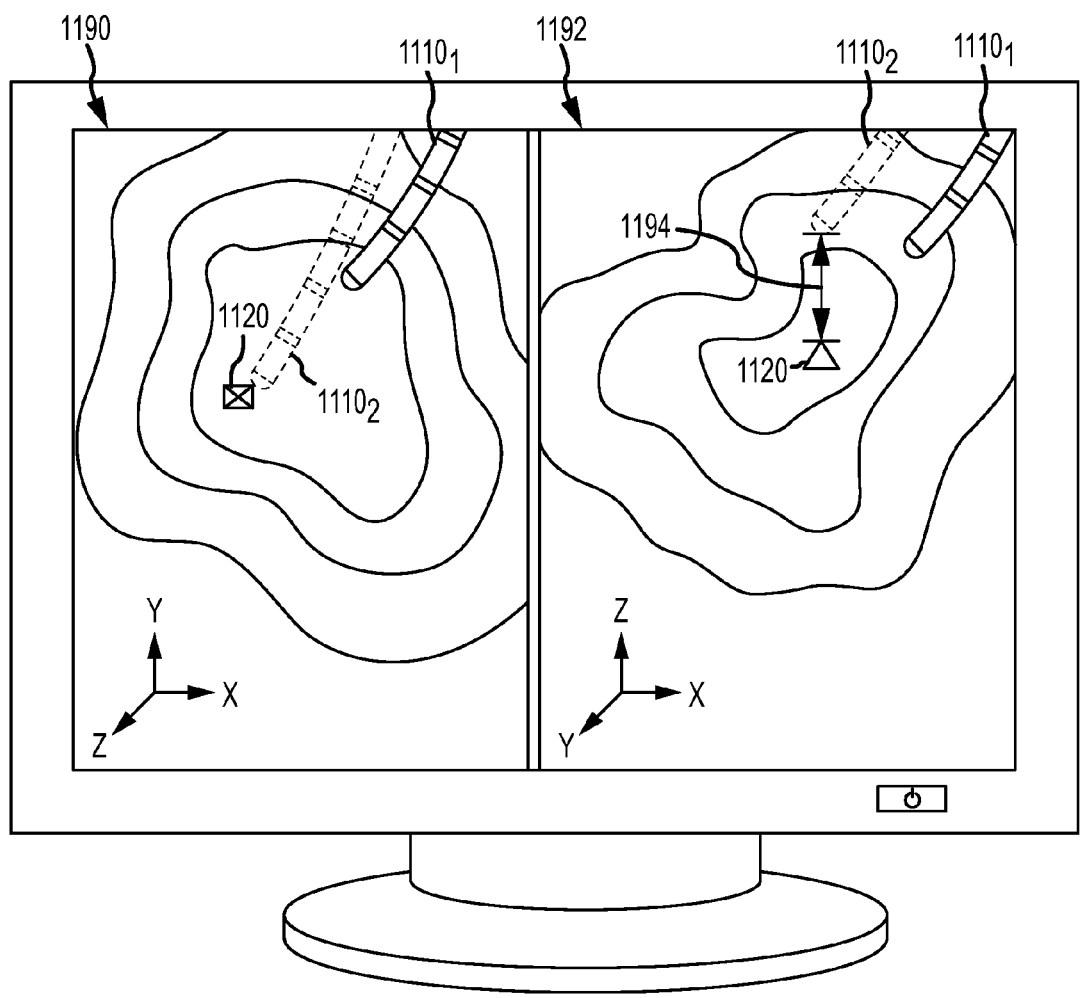
FIG. 19i is an embodiment of a display displaying multiple views of an anatomical model.

In an embodiment, UI logic 1152 and display logic 1546 can be configured to provide two views of an anatomical model on which the representation of the catheter and target point are specified, as shown in FIG. 19i. A first view 1190 can be the primary view of the anatomical model to which the input coordinate system is aligned. That is, a movement of catheter 1110 to the left with input device 1520 can be a move to the left in first view 1190. Second view 1192 can be configured to remain constantly orthogonal with respect to a point in first view 1190. In particular, when placing a target point 1120 (shown as a 3D square-base pyramid symbol), second view 1192 can be of a plane that is orthogonal to the plane of first view 1190 and that includes target point 1120. Thus, first view 1190 shows the "top" of target point 1120, and second view 1192 shows the "side." By showing dual, mutually-orthogonal views 1190 and 1192, method 1180 and control system 1140 allow a user to set the depth of a target point without requiring a separate input device to set depth, such as a wheel or slider. However, a separate input device, such as a wheel or slider, can be used in conjunction with a dual view of the anatomical model to provide an additional or alternative way to set the depth of a target point. For example, actuation of a mouse wheel or on-screen slider while a target point is selected can move the target point "in" or "out" of the plane of the display. Furthermore, by showing dual orthogonal views 1190, 1192, control system 1140 allows the user to see the distance between medical device 1110 and the target point 1120. For example, in first view 1190 (showing the X-Y plane), a movement of catheter 1110 from a first position (designated $1110_1$) to a second position (shown in phantom and designated $1110_2$) appears to bring catheter 1110 to target point 1120. However, as can be seen in second view 1192 (showing the X-Z plane), catheter 1110 actually remains a non-zero distance 1194 away from target point 1120. Dual orthogonal views 1190, 1192 allow a user to quickly make such distance determinations. The method proceeds to step 1188.

At step 1188 (FIG. 19h), the UI logic 1152 is configured to determine whether the user affirms that the candidate target point should be at the currently specified location (i.e., the location as per step 1186). The user can be prompted, for example, by setting the target point symbol to a particular color as a candidate point, by verbally prompting the user, or the UI logic 1152 can be configured to recognize some predetermined input as an affirmation that the candidate target point should be the final target point. If the answer in step 1188 is "YES" (i.e., the user affirms the target point location, such as by clicking (mouse) or tapping (touch screen) on the displayed target point, or by clicking or tapping an affirmative response to a verbal prompt), then the method proceeds to step 1190. On the other hand, if the answer in step 1188 is "NO" (i.e., the user declines to adopt the current candidate target point location as the final location), then the method branches to step 1184 (i.e., the UI logic 1184 awaits a "new" input corresponding to the new candidate target point location). The "new" desired target point input can be a different target point, or can be the relocation of the original candidate point.

At step 1190, the method passes the final target point location to the control logic 1544, for further processing consistent with the pre-programmed movement strategies described elsewhere herein.

Haptic feedback based on actual sensed forces on a distal catheter tip will now be discussed.

An embodiment of user interface device 1000 that incorporates movement of a physical input device can include touch-type feedback, often referred to as "haptic feedback" This type of feedback can involve forces generated by a motor connected to user interface device 1000 that the user can feel while holding the device, also disclosed in commonly owned U.S. Patent Application Publication 2010/0073150, titled "Robotic Catheter System including Haptic Feedback," which is hereby incorporated by reference in its entirety. These forces can be based on actual or computed forces being applied to a physical catheter tip. In an embodiment, the unit can sense forces using a force and/or impedance sensor in the tip of the catheter and generate a corresponding force on an input handle. In other embodiments, the forces can be based on a computed geometric model of the cardiac anatomy, such as that associated with the St. Jude Medical, Inc. EnSite™ system.

In an embodiment, haptic feedback can be conveyed to a user by employing an input device instrumented with motors/encoders on each degree of freedom. Though the motors can operate in a passive mode for a majority of the procedure, if feedback is required by the system, the motors can be energized to produce a torque on the input controls capable of retarding the user's movement in particular degrees of freedom. While in a passive mode, the motor typically will not produce a significant retarding force, however the attached encoder can record the input for use in visualization and control routines.

Prior to a haptic response being conveyed, the system can first calculate the appropriateness and magnitude of such a force. In an embodiment, such a force can attempt to replicate a contact between an actual catheter tip and a portion of the cardiac anatomy. In an embodiment, such contact can be either directly sensed through one or more force sensors on the distal tip of the catheter/sheath, or can be calculated based on a virtual catheter/sheath position within a rendered geometric computer model.

In an embodiment where haptic forces are based on actual catheter contact, the catheter's distal tip can be instrumented with a force sensor configured to provide an indication when physical contact is detected. Such a force sensor can include, without limitation, load cells, shape memory alloy based force sensors, piezoelectric force sensors, strain gauges, or optical-based or acoustic-based force sensors. One example of a contact sensor that can be used is described in detail in U.S. patent application Ser. No. 11/941,073 entitled "Optic-Based Contact Sensing Assembly and System," which is hereby incorporated by reference in its entirety herein. In other embodiments, a contact or proximity sensor can be used, such as those associated with detected electrical impedance. One example of a proximity sensor that can be used is described in detail in U.S. patent application Ser. No. 12/465,337, entitled "System and Method for Assessing the Proximity of an Electrode to Tissue in a Body," which is incorporated by reference in its entirety.

In an embodiment employing actual contact sensing, the sensor can generate a signal representative of the actual physical or electrical contact. Based on the magnitude and direction of the sensed force, as well as the current position of the input device, the system can produce a corresponding torque or force on the input device that can resist further movement through the obstructing anatomy. The system can be configured so that the user would feel this reaction force as if the input device was impacting a "virtual wall."

Based on the system calibration, the resistive force the user feels at the input joystick could be more or less "spongy." That is, the system could be tuned so that a tip impact with the cardiac wall is either felt like a rigid impact with an immovable object, or perhaps as a contact with a soft sponge.

Haptic feedback based on virtual catheter tip proximity to virtual cardiac anatomy will now be discussed.

As discussed above, in an embodiment, haptic feedback forces can be conveyed to a user based on contact forces computed from the proximity between a virtual catheter model and a computer-generated representation of the cardiac anatomy. In an embodiment, the positioning of the virtual catheter model can be obtained through an impedance-based position detection system (e.g., such as associated with St. Jude Medical's NavX™ system), or through a magnetic-based position detection system (e.g., such as associated with Mediguide's gMPS positioning system). Further such a computer-generated representation of the cardiac anatomy can be derived from prior CT or MRI data, or a model (such as that created or maintained by St. Jude Medical's EnSite™ system).

With such embodiments/configurations, a user can have a previously obtained geometric model of the cardiac anatomy. This model can be visible to an electrophysiologist user through a visualization system (such as, for example, St. Jude Medical's EnSite™ system or another system free of ionizing radiation). This model can be assembled using, for example, previously captured CT or MRI images, and/or "skinned" geometry obtained by sensing actual position data of a mapping catheter (e.g., with St Jude Medical's NavX™ system or the gMPS system). Once the model is assembled, a catheter locating system (e.g., St. Jude Medical's NavX™ System or the gMPS system) could then place the working catheter inside the computed geometric model. In an embodiment, as the catheter is moved within the geometry, a haptic system could be used to compare the positioning of the catheter to that of the generated geometry. If the catheter is perceived to be in contact with the generated geometry, a resistive force could then be generated in connection with the associated input device—e.g., using attached motors.

In an embodiment, the geometric model can be registered to a repeating physiological signal such as, for example, the cardiac rhythm or respiration rhythm. As this signal is sensed in the actual procedure, the model geometry can dynamically change. This can then enable computed haptic feedback to provide a more accurate representation of the contact actually occurring within the patient.

A displayed orientation vector within the visualization software to show direction of planar, thumb switch deflection will now be discussed.

With some traditional, non-robotic catheter procedures, a thumb switch on the catheter handle causes catheter deflection by tensioning a corresponding steering wire. Such a switch typically allows the distal tip of a catheter to laterally deflect in one of two opposing directions in a single plane. If deflection is desired in more than one plane, a user commonly could physically rotate the catheter about its longitudinal axis to cause the deflection plane to rotate.

In an embodiment of robotic catheter system 10 incorporating instrumented traditional catheter handle input controls, as described above, an indicator can be provided within a computer visualization to give the user an idea of which direction the distal tip will deflect if the deflection thumb switch is actuated. In an embodiment, such a representation (e.g., deflection plane vector) can include an arrow superimposed near the tip of the virtual representation of a physical catheter. Such an arrow can indicate the direction the catheter would move if the thumb switch were pulled toward the user. Similarly, pushing a control (e.g., thumb switch) can cause the catheter to deflect in the opposite, arrow tail direction. The user can then cause a rotation of this vector by rotating an input handle, which can then be sensed by the attached motor/encoder or potentiometer. Similarly, a deflection vector could be associated with sheath visualization.

The general mechanics of the catheter and sheath movement will now be described with reference to FIGS. 20-22.

Figure 20:
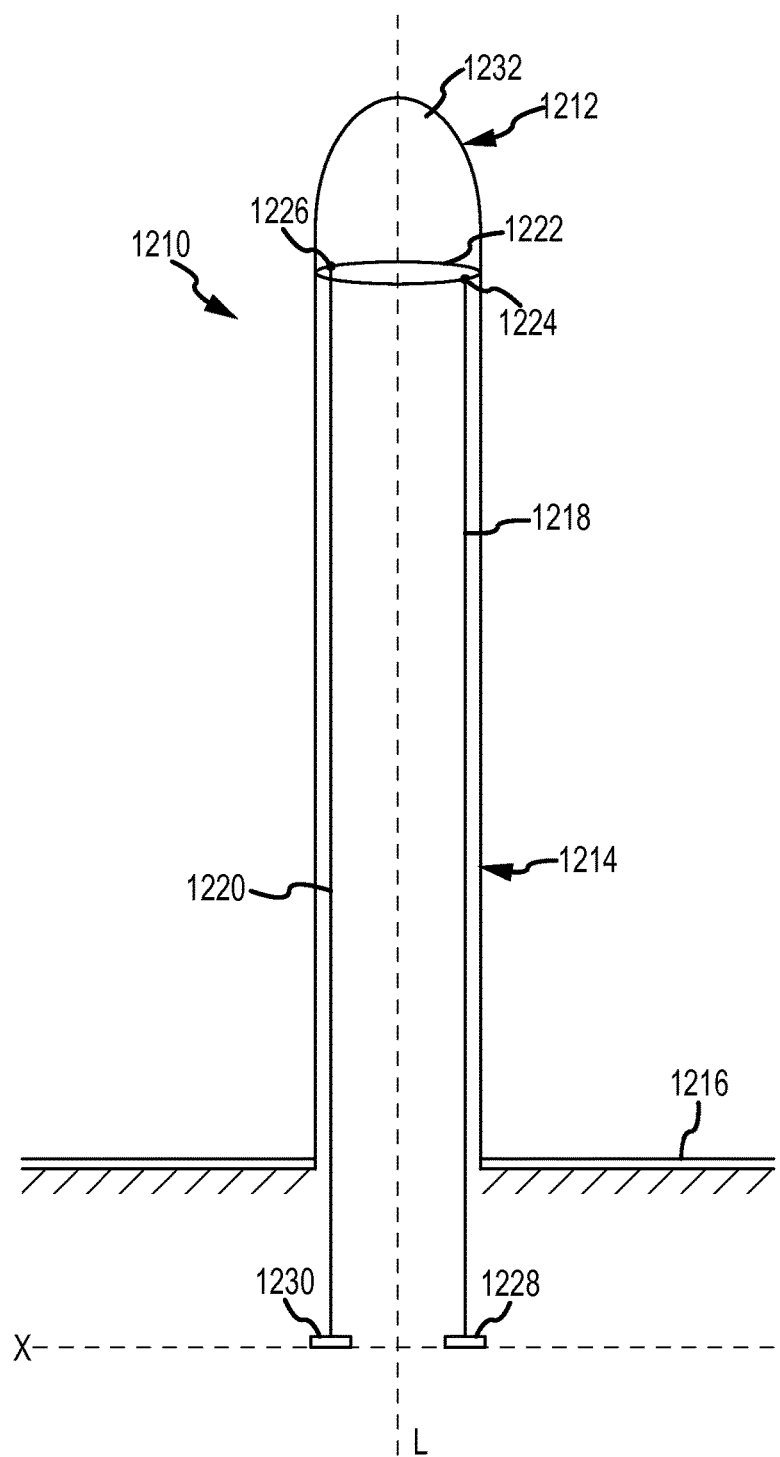
FIG. 20 is a general representation of a catheter according to an embodiment of the invention, shown in an undeflected state.

As generally illustrated in FIG. 20, the catheter 1210 can include at least two steering wires 1218, 1220, each longitudinally situated within and along a substantial length of the catheter 1210. In an embodiment, the steering wires 1218, 1220 can be comprised of a material having a high elastic modulus—such as, for example, steel or aluminum. The catheter 1210 can further include a pull ring 1222, which can take the form of a rigid ring firmly connected or affixed within a portion of the distal portion 1212 of the catheter 1210. Each steering wire can be rigidly connected to pull ring 1222, for example, via a rigid connection or coupling 1224, 1226. In an embodiment, such a rigid connection or coupling can comprise a weld, braze, or other known means of attachment.

As generally depicted in the illustrated embodiment, proximal portions of the steering wires 1218, 1220 can be respectively connected to control members 1228, 1230. Control members 1228, 1230 can be, for example, slider blocks such as those mentioned above, and can be used to interface or operatively connect control devices, such as the fingers of the manipulator assembly, to the steering wires 1218, 1220. For illustrative purposes, as generally shown in FIG. 20, when catheter 1210 is configured in an undeflected state on longitudinal axis L, control members 1228, 1230 can both be situated at a one or more initial or common reference levels or datum (e.g., common datum X shown in FIG. 20). However, for some embodiments, no initial relationship of control members 1228, 1230 is necessary, and the positioning of each can, for instance, simply be a consequence of initial assembly.

Figure 21:
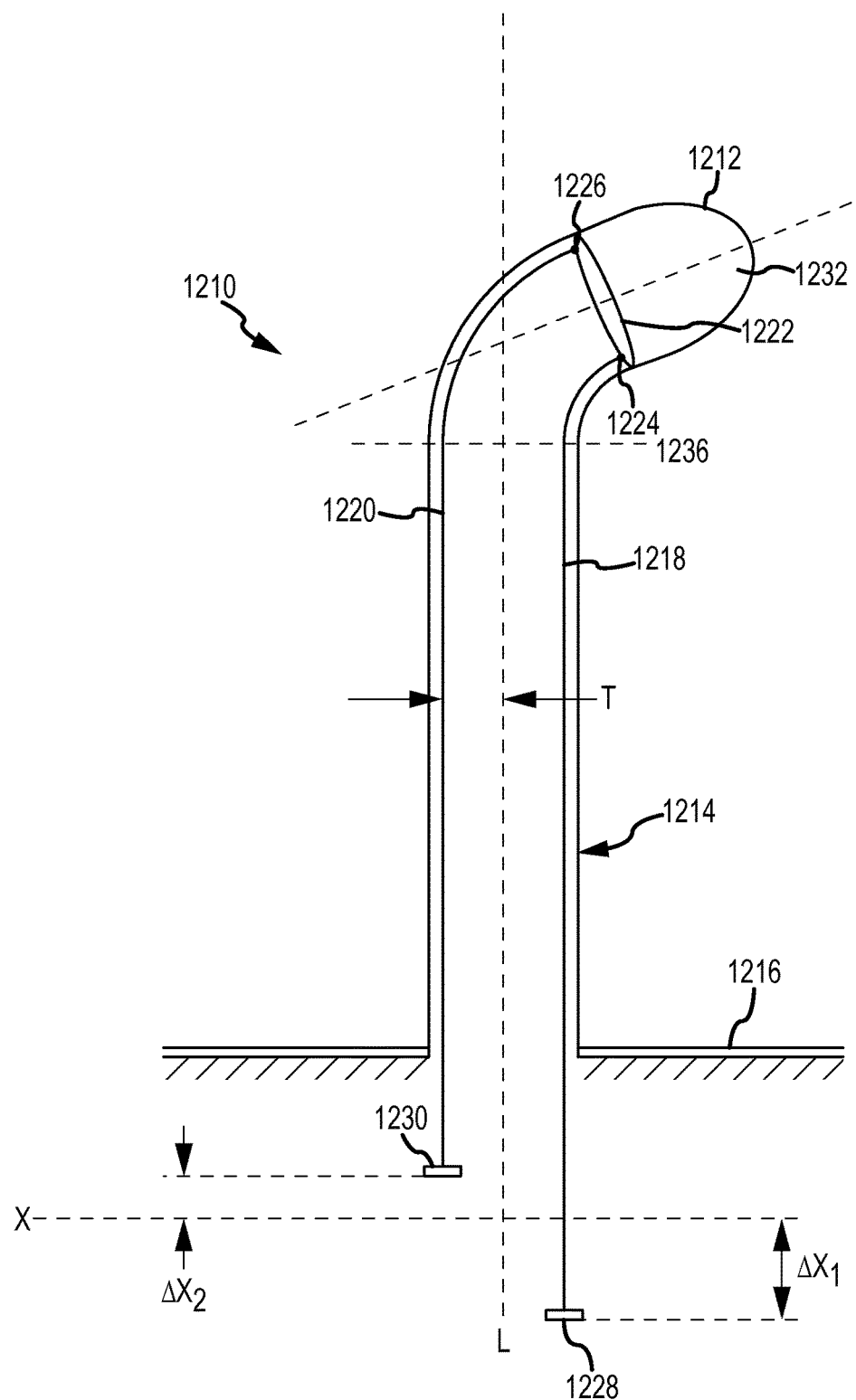
FIG. 21 is a general representation of a catheter of the type illustrated in FIG. 20, shown in a deflected state.

As generally shown in FIG. 21, the distal portion 1212 of catheter 1210 can be deflected or displaced away from longitudinal axis L by selective actuation or tensioning of one or more steering wires. For example, as generally illustrated in FIG. 21, control member 1228 can be translated in a proximal direction a distance $\Delta X_1$, which causes a tension response in steering wire 1218. The actuation of steering wire 1218 causes a corresponding deflection of the bendable section (i.e. the portion of catheter 1210 between fulcrum point 1236 and pull ring 1222) in a direction toward steering wire 1218. In the illustrated embodiment, the fulcrum 1236 generally defines the point along the length of the catheter at which the catheter 1210 transitions from a stiffer, proximal portion, to a more bendable, distal portion. In an embodiment, such increased bendability can be caused by using a material of a lesser durometer in the distal portion than in the proximal portion of the catheter. Alternatively, the fulcrum point 1236 can define a transition point of the catheter where the internal structure of the catheter is modified in a manner known in the art to promote distal bending.

As further illustrated in FIG. 21, while control member 1228 is actively deflected a distance $\Delta X_1$ in a first proximal direction, control member 1230 reactively moves or retracts a distance $\Delta X_2$ in a second, substantially opposing distal direction. The reactive motion of control member 1230 and steering wire 1220 can depend on the difference in arc lengths between the two steering wires within the bendable section of the catheter. Assuming the distal portion bends with a constant radius of curvature, the arc lengths of the steering wires would then be a function of a transverse distance—e.g., distance T between steering wire 1218 and the central longitudinal axis L—and the bending radius of curvature of the distal portion 1212. While, theoretically, displacements $\Delta X_1$ and $\Delta X_2$ can bear a linear relationship to each other, non-uniform axial compression of catheter 10 can cause the relationship between $\Delta X_1$ and $\Delta X_2$ to be non-linear.

To cause catheter 1210 to move or retract back to an undeflected state along longitudinal axis L, a user could, for example, actively translate control member 1230 in a proximal direction. Such a motion could cause the distal portion 1212 to rotate and deflect toward steering wire 1220, while control member 1228 would be reactively translated in a distal direction. In an embodiment, due to memory effects of catheter 1210, such as caused by plastic deformation, upon restoring catheter 1210 to an undeflected state along longitudinal axis L, control members 1228, 1230 can not necessarily return to their original positions (e.g., on datum X).

It is noted that while FIGS. 20-21 illustrate the operation of a catheter having two steering wires oriented in a planar configuration, other embodiments can include three or more steering wires that can cause three dimensional motion of the distal portion of the catheter. FIG. 22 generally shows an axial cross-section of a catheter embodiment, taken at the fulcrum point, that includes four steering wires 1240a, 1240b, 1240c, 1240d. While this illustration displays all steering wires spaced approximately 90 degrees apart, various other configurations can be provided.

Figure 22:
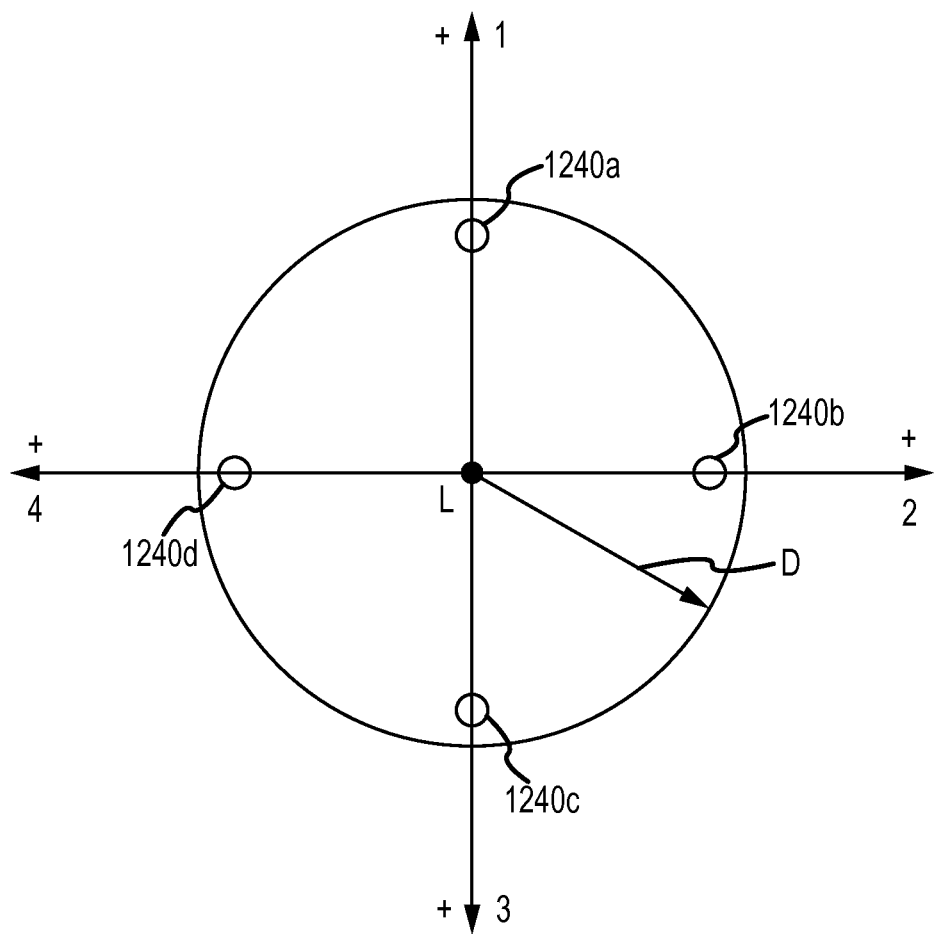
FIG. 22 is a graph of catheter deflection as a function of steering wire tension.

As generally illustrated in FIG. 22, the respective tensioning of adjacent steering wires can cause a deflection of the distal portion 1212 of catheter 1210 in a unique direction, e.g., direction D. Through selective actuation of pairs of steering wires, the distal portion of the catheter can be made to traverse circles of varying radii about longitudinal axis L (as viewed transverse to the page). The embodiment illustrated in FIG. 22 is similar to the two-steering wire embodiments shown in FIGS. 20-21, since, when any wire or wires are actively tensioned, the opposing wires is permitted to reactively move a distance in an opposing distal direction. For example, as shown in FIG. 22, to cause a distal motion in direction D, steering wires 2 and 3 (1240b, 1240c) can be positively tensioned, while steering wires 1 and 4 (1240a, 1240d) would move reactively.

Figure 23A:
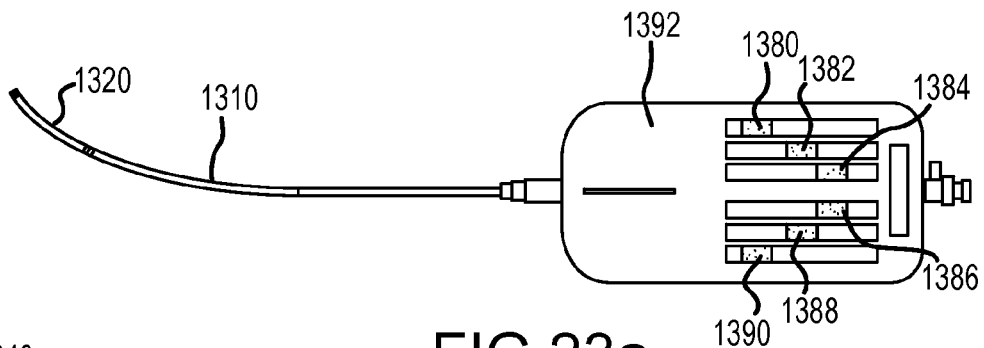
FIGS. 23a-23d are illustrations of a robotic catheter device cartridge employing multiple deflection zones.
Figure 23B:
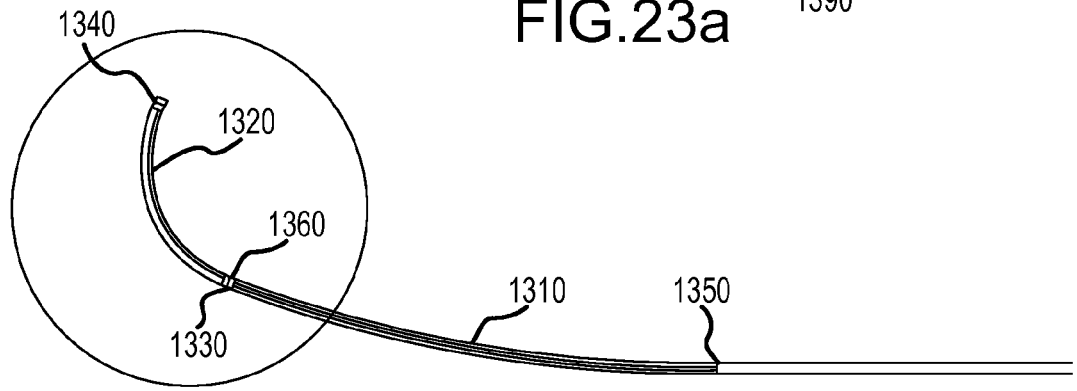
Figure 23C:
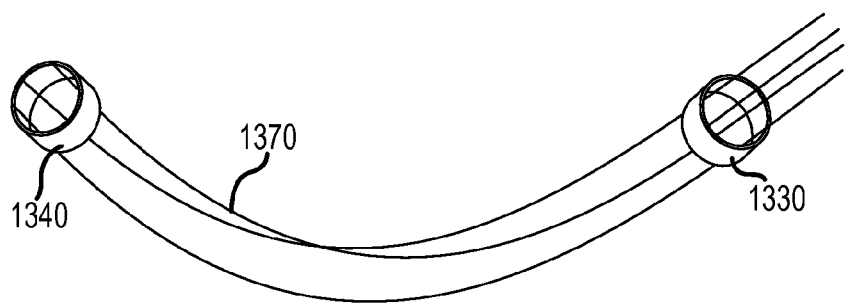

In an embodiment, as illustrated in FIGS. 23a-23c, the catheter can include multiple bendable sections (e.g., sections 1310, 1320), each having a separate pull ring (e.g., pull rings 1330, 1340), fulcrum point (e.g., fulcrum points 1350, 1360), and associated steering wires coupled with each pull ring. The inclusion of multiple bendable sections can allow a user to achieve compound bending postures with only a single device. In an embodiment, the catheter can include a first bendable section 1310 and second bendable section 1320 that are capable of independently directed bending motions. In other embodiments, the catheter can include three or more bendable sections.

In the embodiment illustrated by FIGS. 23b-23c, each bendable sections has a proximal fulcrum point 1350, 1360, a pull ring 1330, 1340 located distal to the fulcrum point, and a set of steering wires attached to the pull ring. The steering wires for both sections extend from the proximal end of the catheter, through the body of the catheter, and are affixed to the respective pull rings, as shown in FIG. 23c. In an embodiment, the fulcrum point for the second bendable section can be located at the pull ring for the first bendable section, as shown in FIG. 23c. In another embodiment, the fulcrum point can be located distal to the first pull ring.

Figure 23D:
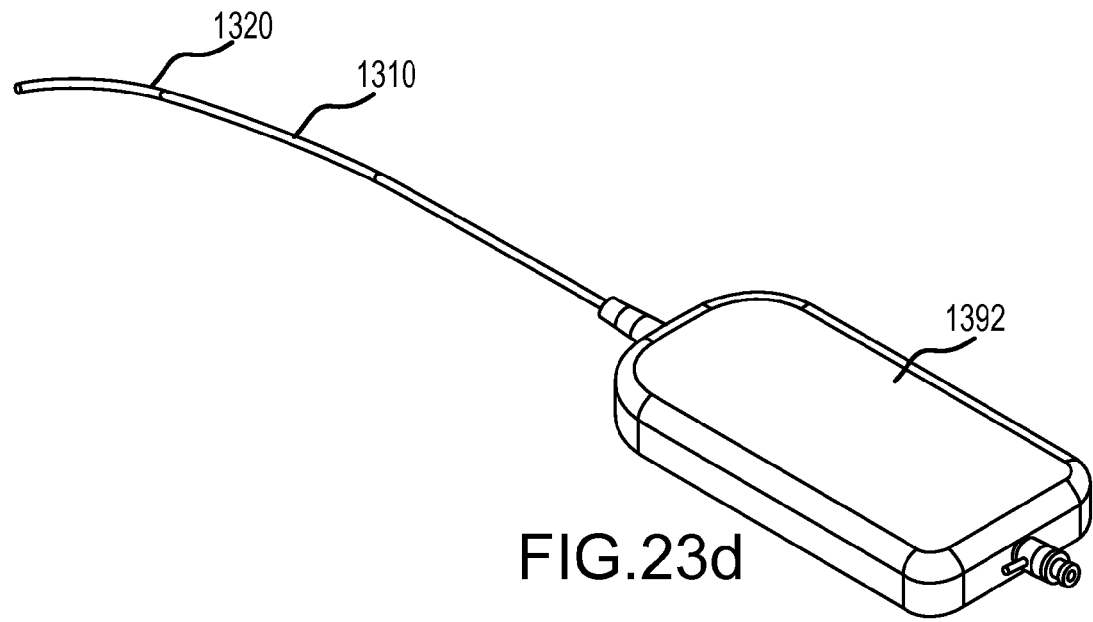
Figure 23E:
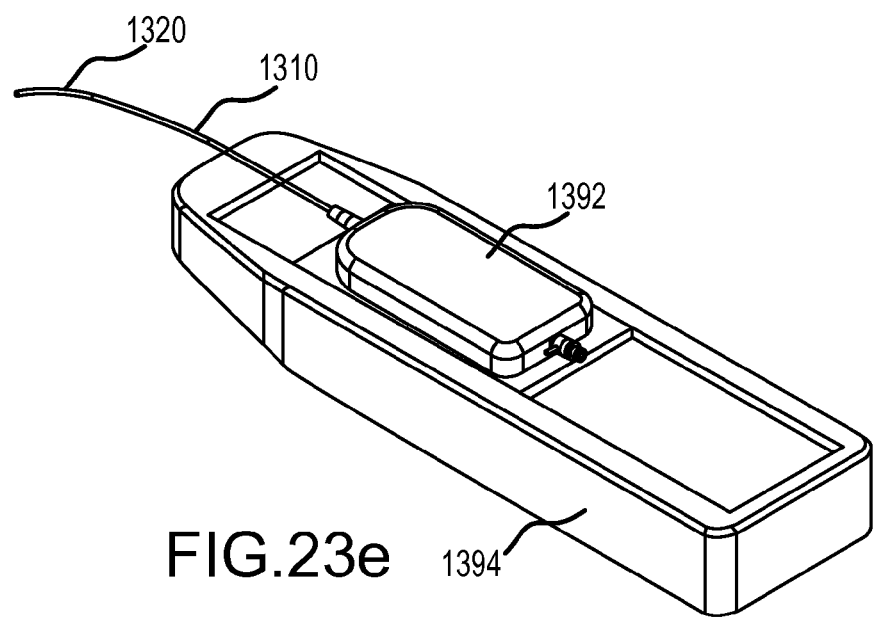
FIG. 23e is an isometric view of an embodiment of a robotic catheter device cartridge having multiple deflection zones coupled with an embodiment of a robotic catheter manipulator.

Similar to the cartridges described above with respect to FIGS. 5a-e, as shown in FIG. 23a each of the six steering wires can be coupled with a respective slider block (e.g., slider blocks 1380, 1382, 1384, 1386, 1388, 1390) within a proximal cartridge 1392. The cartridge 1392 can, in turn, be configured to interface with a robotic manipulator 1394, as shown, for example, in FIGS. 23a, 23d, 23e. While FIGS. 23a, 23d, 23e depict the multi-deflection zone catheter operating in a single cartridge system, it should be understood that the catheter can also be used in conjunction with a sheath cartridge as described above.

Active tensioning of "passive" steering wires will now be briefly discussed with reference to FIGS. 5a-5e (as discussed above) and 24-25.

Figure 24:
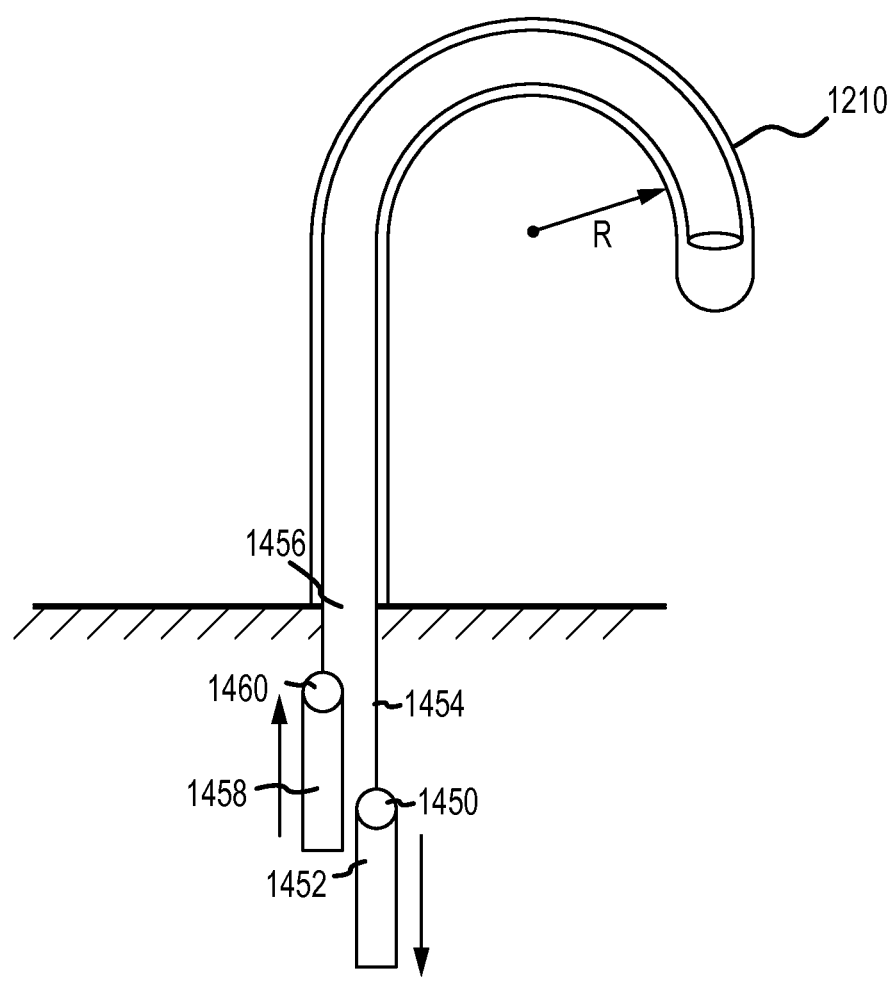
FIG. 24 is an exemplary view of steering wire movement for a two-wire catheter.

As described above, an embodiment of robotic catheter system 1210 can provide for tensioning of the steering wires (e.g., by moving fingers/slider blocks in a proximal direction). As generally shown in FIG. 24, active manipulator finger 1450 pushes slider block 1452 in a proximal direction. This motion causes the attached steering wire 1454 to tension, resulting in a distal deflection of the catheter tip. To allow the displacement, steering wire 1456 could move in a distal direction due, in part, to the radius of curvature R of the catheter bend. This causes the attached slider block 1458 to be pulled in a distal direction. In an embodiment, the manipulator fingers are not allowed to freely move due to their mechanical mounting (e.g., on a high-precision drive mechanism). To then allow the passive slider block 1458 to move distally, manipulator finger 1460 can be compelled to move in a distal direction.

Figure 25A:
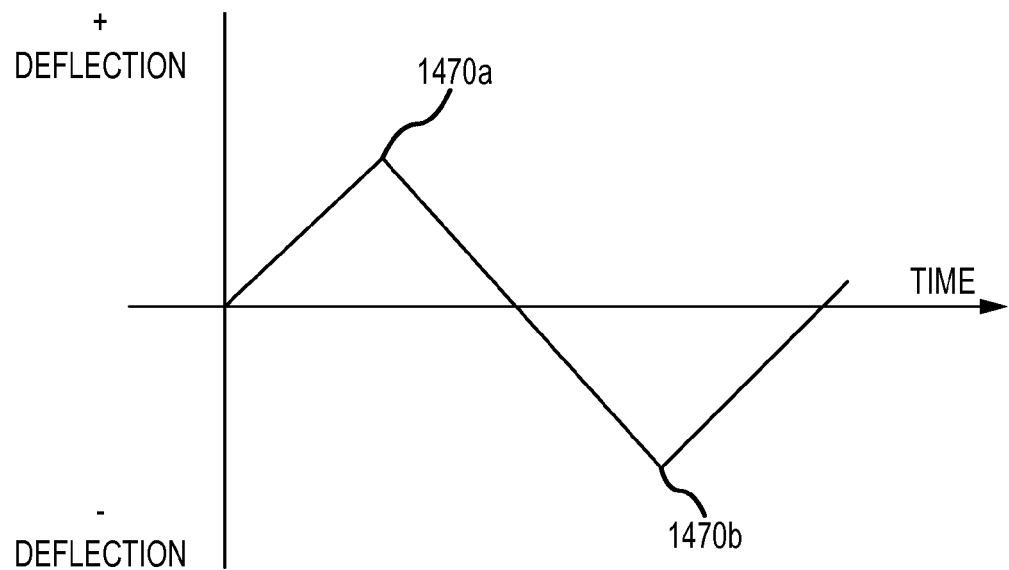
FIG. 25a is a graph that generally illustrates a dynamically responsive catheter motion and FIG. 25b is a graph that generally illustrates a catheter motion with transition latencies.
Figure 25B:
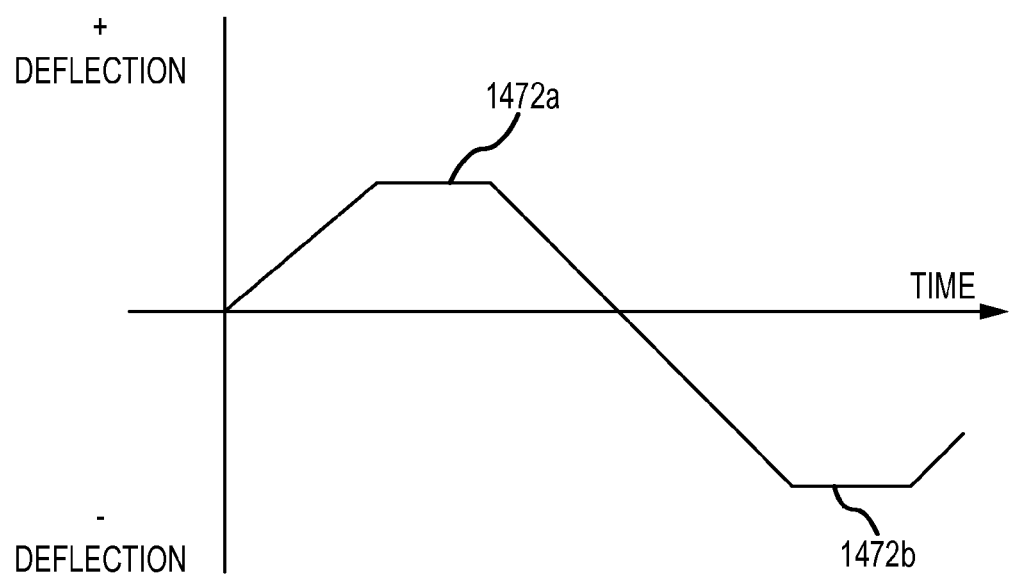

In an embodiment, to help prevent fingers 1460 from impeding passive steering wires 1456, each finger can be retracted to a "home" position when it is not controllably tensioning a steering wire. Such a return-to-home configuration can, at least in part, help ensure that each finger 1460 will not obstruct the distal motion of passive slider blocks 1458. It can be desirable, however, for such a configuration to include features to address issues associated with reduced system response time and potential step-wise distal tip motion, attributable to the time needed to move fingers 1460 back into contact with slider-blocks 1458 when the passive slider blocks could be tensioned to cause a desired movement. FIG. 25*a* includes a graph that generally illustrates a desirable, dynamically responsive catheter motion. This graph demonstrates a motion with sharp transitions 1470*a*, 1470*b* between active and reactive steering wires. In contrast, FIG. 25*b* illustrates a catheter motion that exhibits somewhat undesirable unresponsive states 1472*a*, 1472*b*, which can be occasioned by a need to re-tension reactive steering wires during a transition period.

It can be desirable, for example during a medical procedure, for the distal portion of a catheter to be capable of prompt dynamic, back and forth movements, such as those illustrated in FIG. 25*a*. To help facilitate such movement, it can be beneficial to maintain a minimal tension on all steering wires, even when such a steering wire can be reactively translating in a distal direction. Such a base or minimal tension can help ensure that no undesirable measure of slack is created in any steering wire that could potentially cause an unresponsive state (even if only momentarily) during a transition from a motion in one direction to motion in another direction. In an embodiment, passive slider blocks 1458 can be allowed to freely retract yet avoid contact latencies by incorporating a force sensor in mechanical communication each manipulator finger 1460. In such an embodiment, each passive finger 1460 can be controllably positioned such that a minimal contact force between finger 1460 and the passive steering wire slider block 1458 is always maintained. This ensures that all passive steering wires 1456 are maintained in a "ready" state yet are not significantly impeded. Such "active tensioning" can involve a closed loop algorithm that constantly monitors the force exerted on each finger 1460 through the use of, for example, strain gauges. The "active tensioning" control routine then can translate corresponding passive fingers 1460, by actuating a connected drive mechanism, to maintain contact force between finger 1460 and slider block 1458 within a bounded range (e.g., 50-100 grams of force).

Figure 26:
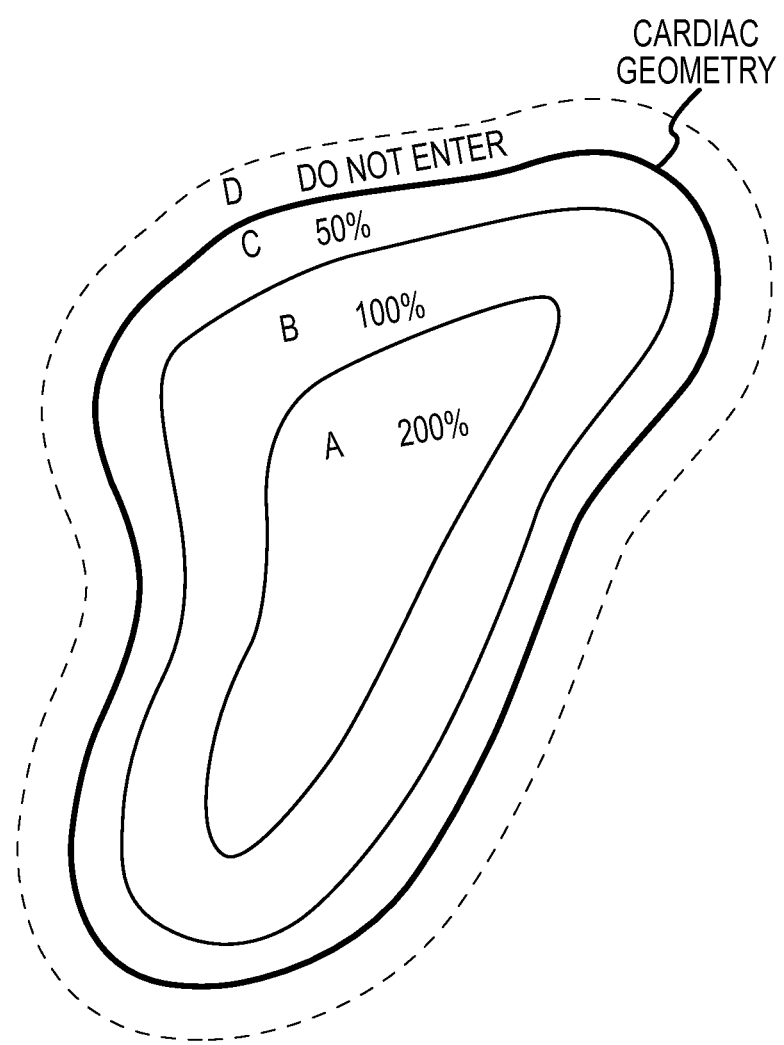
FIG. 26 is an exemplary view of speed-zones for optimizing movement of a catheter tip.

Pre-defined catheter "speed zones" will now be briefly discussed with reference to FIG. 26.

To aid users in navigating a catheter safely, yet quickly, around a cardiac chamber, robotic catheter system 10 can employ pre-defined "speed zones" to optimize the movement of the catheter tip. In an embodiment of the robotic catheter system, the user can have the ability to configure the maximum allowable catheter speed, or alternatively configures the scaling factor that relates the user input to the catheter motion, as a function of the orthogonal distance between the catheter and the nearest cardiac tissue. As described in relation to FIG. 26, zone A can be defined as the most central, and safest area in the cardiac chamber. In zone A, the catheter tip can be sped up so that the catheter tip can traverse this area at a faster than normal rate, e.g., 200% of the input motion. As the user moves the catheter closer to the cardiac wall, he/she can desire enhanced precision rather than speed. Therefore, zones B and C can purposefully and gradually reduce the scaling factor between input motion and tip movement. Finally, the user can have the ability to define a region exterior to the geometry, e.g., zone D, into which the catheter is prevented from entering. Alternatively, this "exterior zone" can be modeled to provide a force that would "push" the catheter back into the acceptable area.

If desired, the system can include a corresponding haptic response in the input joystick. For zones A, B, and C, such a haptic response can involve changing the dampening force on the handle (e.g., as the tip moves closer to the wall, the user might feel as if the tip is caught in an increasingly dense sludge). Once the tip starts to cross the barrier between zone C and zone D, this feeling can be accompanied by a force that prevents inadvertent continued motion.

User guided robotic control will now be discussed with reference to FIGS. 27-43.

Figure 27:
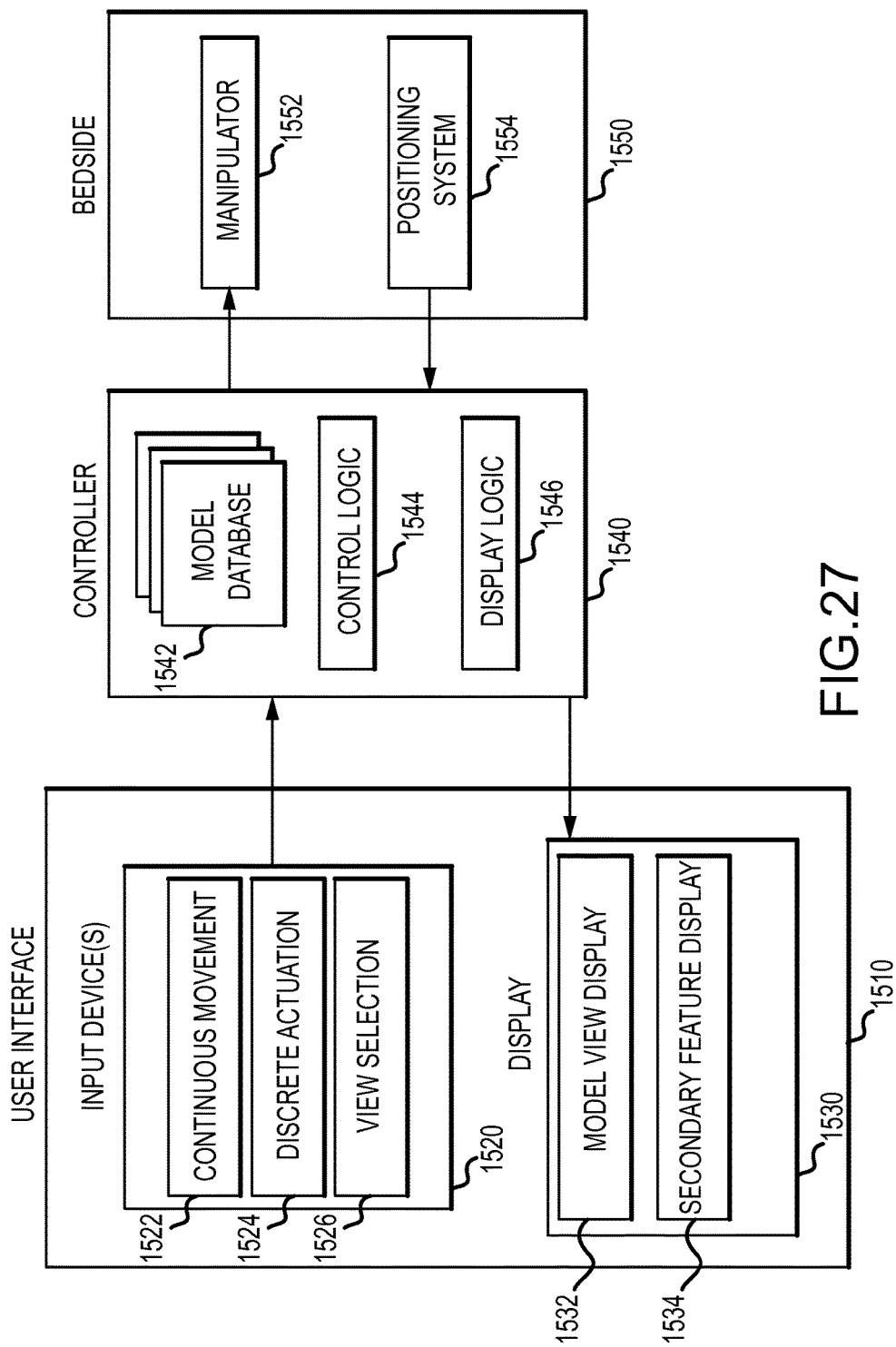
FIG. 27 is a diagram of one embodiment of a robotic catheter system.

As schematically represented in FIG. 27, and described above, the robotic catheter system 10 generally includes three primary components: a user interface 1510, a robotic controller 1540, and a bedside system 1550. The user interface 1510 generally includes one or more input devices 1520 and one or more displays 1530. The controller 1540 generally includes an anatomical model 1542, control logic 1544, and display logic 1546. The bedside system 1550 generally includes one or more manipulator assemblies 1532, and a positioning system 1554.

In an embodiment of the user interface 1510, the one or more input devices 1520 can be configured to receive input from a physician corresponding to both a continuous movement 1522 of the input device 1520 and a discrete actuation 1524 of the input device 1520. The user interface can further provide the physician with a means of selecting a particular viewing perspective 1526 of a three dimensional anatomical model 1542. As used herein, a continuous movement input is one that can be represented on a continuous spectrum, such as the movement of a joystick, mouse, or slider. While it is understood that current digital computing operates in discrete increments, the term "continuous movement" as herein used, is intended to only distinguish from a discrete actuation, such as a button press, which could be represented as a finite state. The input device 1520 is configured to provide the various forms of user input from the physician to the controller 1540 for processing.

The user interface 1510 can further include one or more visual displays 1510 that are capable of displaying one or more views 1532 of an anatomical model 1542. The display 1534 can further be configured to display one or more secondary features 1534 either together with, or apart from the displayed view of the model 1532. In an embodiment, secondary features can include markers, targets, sliders, menu buttons, patient vital data, or other useful visual information that cannot be strictly representative of the anatomical model 1542. In an embodiment, the displayed view 1526 of the anatomical model can be selected by the user via the input device 1520.

As will be described in greater detail below, the controller 1540 can be configured to maintain a three dimensional anatomical model 1542 of the cardiac geometry, and execute both control logic 1544 and display logic 1546. In an embodiment, the control logic 1544 is configured to relate intended user actions into a controlled physical movement of the catheter and sheath. Such control logic can include the use of, for example, control algorithms, forward and/or inverse kinematic computations, and real-time feedback from the catheter, manipulator, or positioning system. In an embodiment, the display logic 1546 is configured to use three dimensional view rotation, translation, and/or projection techniques to present the user with a displayed representation 1532 of the anatomical model 1542 corresponding to the provided view selection input 1526. The display logic 1546 can further be configured to relate a user input 1522 made with respect to a presently displayed view 1532 into the coordinate system of the anatomical model.

The bedside system 1530 generally includes one or more manipulator assemblies 1532 configured to manipulate a catheter and sheath, and a positioning system 1534 configured to detect the real-time positioning of the catheter and sheath devices within the patient.

In an embodiment of the general control scheme, the controller 1540 can be configured to receive inputs from an input device 1520 configured to resemble a traditional catheter handle, as discussed above with reference to FIGS. 15a-15b. In such a scheme, the controller 1540 can be configured to actuate the manipulator 1552 in a manner that translates the traditional inputs into a resulting motion of the catheter distal tip as if the handle and tip were physically connected. In this configuration, the control logic 1544 can be designed to mimic the feel and operation of a non-robotic catheterization.

In another embodiment of the general control scheme, the controller 1540 can be configured to register user inputs as they are made with respect to a displayed third-person view of the catheter and anatomic model 1542. The physician can therefore be able to use the input device 1520 to move the virtual catheter across the display 1530 in much the same manner as in a traditional computer experience, where a user can use a mouse to drag an object across a display screen. Said another way, a leftward motion of the input device 1520 would result in a leftward movement of the displayed catheter within the currently displayed view 1532 of the anatomical model 1542. The controller 1540 would then be configured to resolve the intended Cartesian (i.e., in the coordinate system of the input device) distal catheter movements into deflection and translation manipulator actuation commands (i.e., in the coordinate system of the manipulator) through control logic 1544 that can cause the actual catheter tip to follow the intended movements.

In another embodiment of the general control scheme, the controller 1520 can be configured to register user inputs as they are made with respect to a displayed third-person view of the catheter and anatomic model 1542 solely for the purpose of controlling directional bending of the catheter. In such an embodiment, translation of the catheter can be separately controlled through the use of a slider, wheel, unused input device axis, or other similar device. The controller 1540 would therefore be configured to resolve the intended display-plane distal catheter movements into deflection-only manipulator actuation commands through control logic 1544, which would cause the actual catheter tip to follow the intended movements within the display plane, but would allow movement orthogonal to the display plane to be controlled by the mechanics of the catheter.

In another embodiment of the general control scheme, the controller 1520 can be configured to register user inputs as if the user was navigating the catheter from a first person point of view. In such an embodiment, the display 1530 would represent the anatomic model 1542 as if the viewing camera was positioned on the tip of the catheter. The physician would therefore be able to use the input device 1520 to steer the catheter in much the same way a driver steers a car while looking out of the front windshield.

Figure 28A:
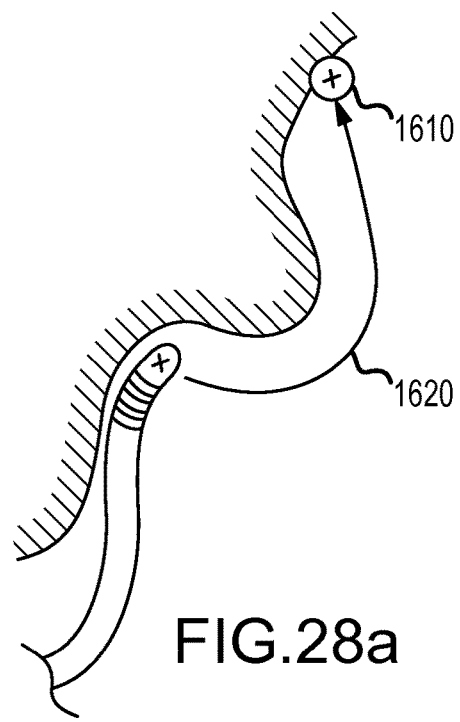
FIGS. 28a-28b are illustrations of embodiments of specifying an intended robotic catheter movement path.
Figure 28B:
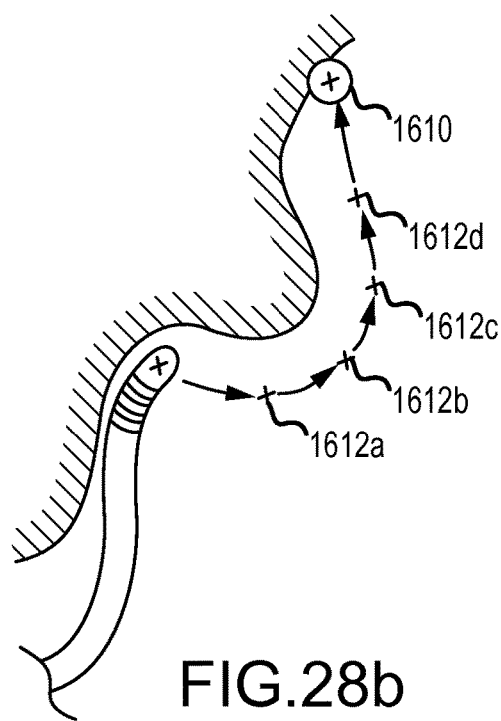

In yet a further embodiment of the general control scheme, as generally illustrated in FIGS. 28a-28b, the controller can be configured to accept static target locations 1610 or a series of waypoints (e.g., waypoints 1612a-1612d), for automated movement. In such a scheme, a user can, for example, select a target point 1610 within the model that he or she intends the catheter to move to. The controller can then construct a path 1620 between its current location and the target. In an embodiment, prior to movement, the controller can employ various optimization and/or path planning routines to construct an optimal path, traversing potential obstructions within the model. In another embodiment, the controller can cause the catheter to move in a direction toward the target location, while employing real-time proximity feedback from the actual catheter to avoid contact with obstructing tissue. Using either method, the controller can determine the necessary steering wire movement required to cause the catheter to progress toward the target while avoiding contact with the tissue. In an embodiment, as shown in FIG. 28a, the physician can use a target destination as an end-point destinations where a particular therapy can be administered. In an embodiment, as shown in FIG. 28b, the physician can use interim way points (such as waypoints 1612a-1612d) or incremental target locations to construct a specific course for the catheter.

Referring back to FIG. 27, the ability to control the ultimate motion of the catheter (via the manipulator actuation) is complicated because each of the input device 1520, the display 1530, the anatomical model 1542, the manipulator 1552, the distal motion of the catheter resulting from manipulator actuation 1552, and the positioning system 1554, can reside in different domains, having different coordinate systems. As used herein, a "coordinate system" or "coordinate frame" is intended to refer a collection of variables representing controllable or perceivable qualities of an object or device. These variables can primarily include position and/or orientation, though should not necessarily defined in Cartesian space. Additionally, other temporal or environmental variables that are not strictly related to position or orientation can be included in a given coordinate system (e.g., time, breathing phase/magnitude, ECG phase/magnitude). It should also be noted that while a given unit can represent a physical distance, it can be represented in various forms, such as for example, inches, millimeters, volts, ohms, impedance, encoder counts, or other such quantities.

Figure 29A:
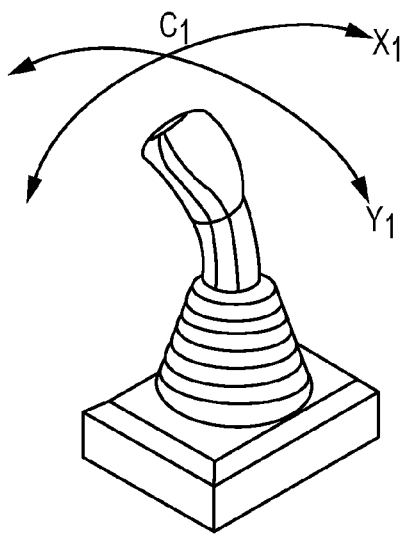
FIGS. 29a-29e illustrate exemplary coordinate systems used in a robotic catheter system.

FIGS. 29a-29e illustrate the various coordinate systems described above. As illustrated in FIG. 29a, an input device, shown as a generic joystick, can operate in a first coordinate system $C_1$. As illustrated, the input coordinate system $C_1$ can include two continuous positional degrees of freedom, $\{x_1, y_1\}$. Depending on the nature of the input device, $C_1$ can further include additional degrees of freedom meant to reflect additional motion, orientation, and/or discrete event triggers.

Figure 29B:
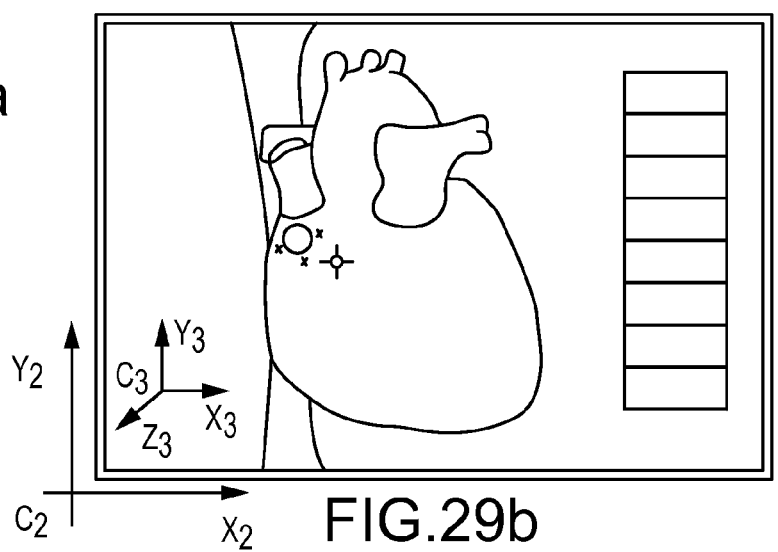
Figure 29C:
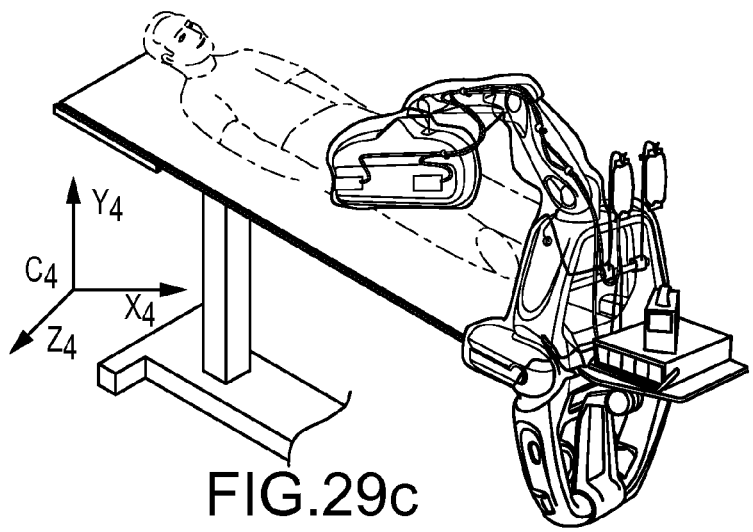
Figure 29D:
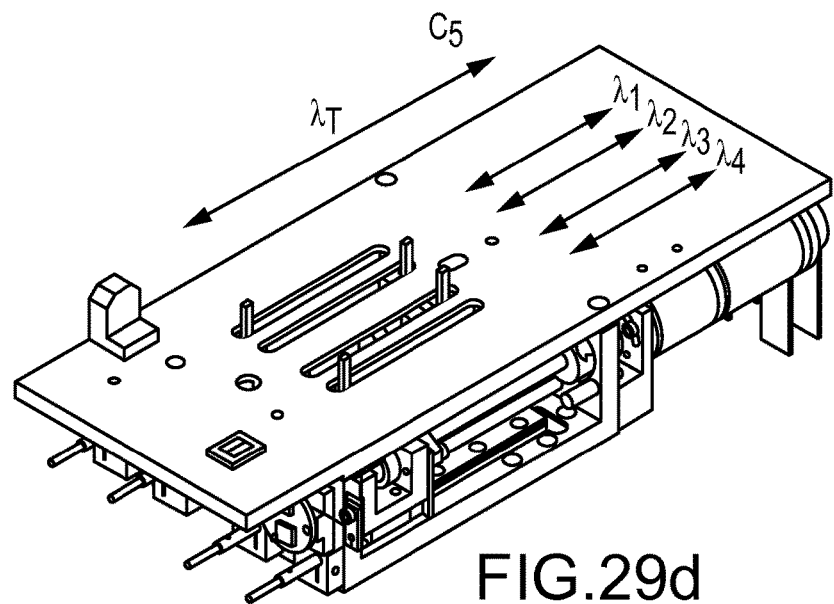

As illustrated in FIG. 29b, the display can have a second coordinate system $C_2$ that can be capable of displaying an image in two dimensional Cartesian space, $\{x_2, y_2\}$. The computerized anatomical model representing the patient's physical anatomy can be registered in the controller as a collection points in a third coordinate system $C_3$, where each point can be defined in a three dimensional Cartesian space $\{x_3, y_3, z_3\}$. As generally illustrated in FIG. 29c, the actual catheter and patient anatomy can exist in a fourth coordinate frame $C_4$, that can have six degrees of freedom $\{x_4, y_4, z_4, \theta_4, \varphi_4, \psi_4\}$ established by the positioning system, where $\{x_4, y_4, z_4\}$ are registered positional coordinates of a given object, and $\{\theta_4, \varphi_4, \psi_4\}$ define the object's orientation in three dimensional space. As shown in FIG. 29d, the manipulator can operate in a fifth coordinate system $C_5$, where each carriage has, for example, four degrees of freedom that relate to the motion of the four steering wires, and one degree of freedom that relates to the translational motion of the carriage $\{\lambda_1, \lambda_2, \lambda_3, \lambda_4, \lambda_T\}$. In two carriage system (i.e., where the manipulator capable of independent catheter and sheath control), each carriage can have, for example, five degrees of freedom, thus providing a manipulator with 10 total degrees of freedom $\{\lambda_1^1, \lambda_2^1, \lambda_3^1, \lambda_4^1, \lambda_T^1, \lambda_1^2, \lambda_2^2, \lambda_3^2, \lambda_4^2, \lambda_T^2\}$.

Figure 29E:
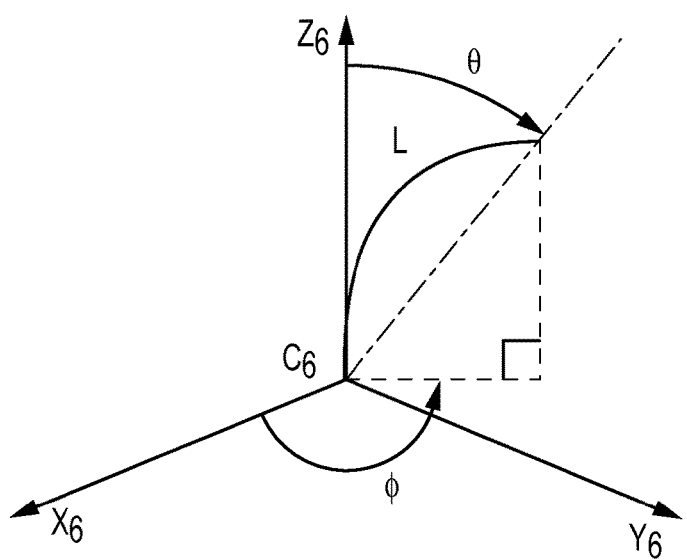

Finally, as shown in FIG. 29e, the distal motion of the catheter can be locally described in a sixth coordinate system, $C_6$, that can be located at the fulcrum point of the catheter. The distal motion within $C_6$ can be described either in a Cartesian space $\{x_6, y_6, z_6\}$ with the z-axis oriented along the longitudinal axis of the catheter, or in a pseudo-spherical space $\{\theta_6, \varphi_6, L_6\}$. In addition to the degrees of freedom listed above, the coordinate systems of the computerized model $C_3$ and the positioning system $C_5$ can be configured to record temporal and environmental degrees of freedom, such as, for example, time, ECG phase, ECG rate, respiration rate, respiration phase, and/or respiration magnitude.

Figure 30:
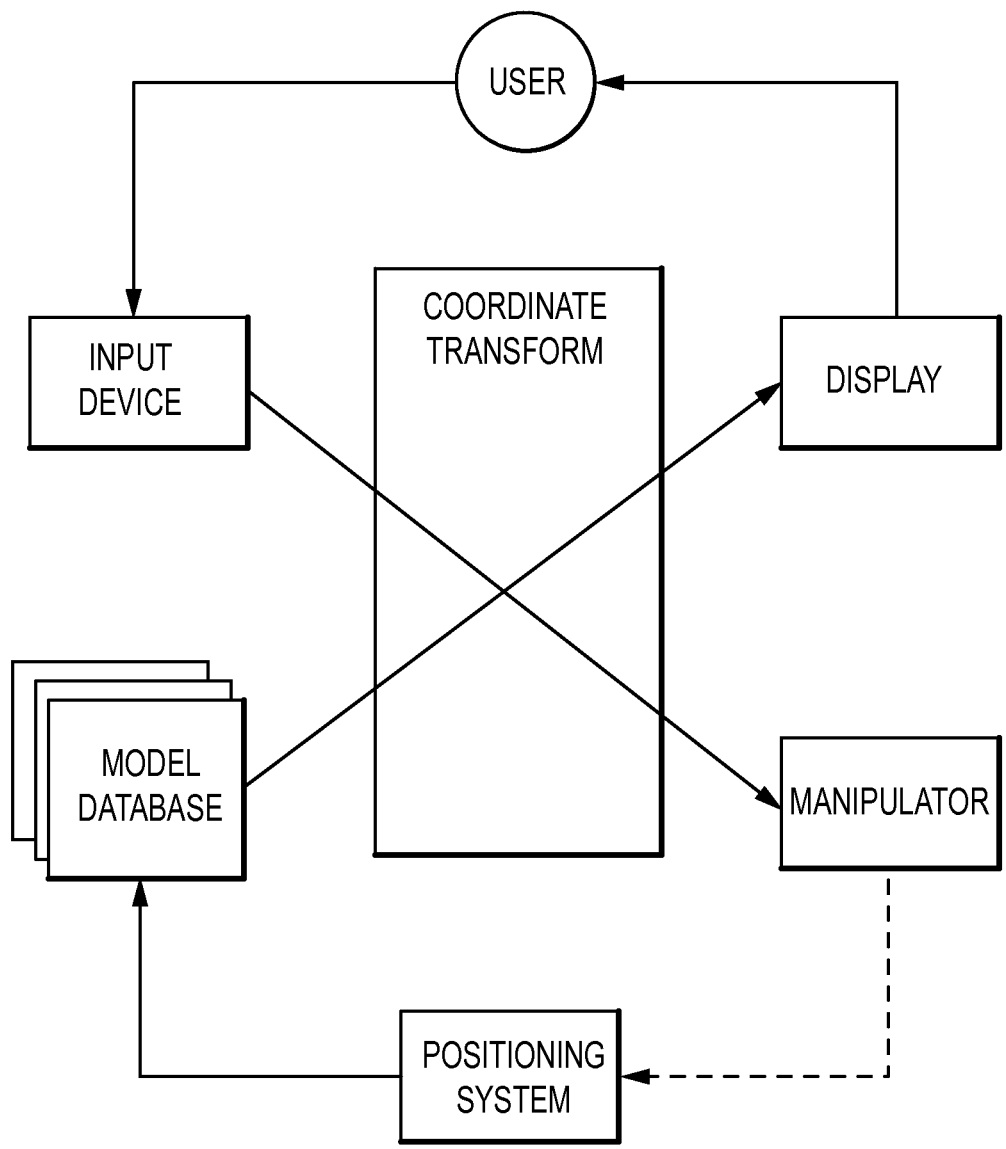
FIG. 30 is a relational diagram for exemplary aspects of a robotic catheter system.

As illustrated in FIG. 30, and described in more detail below, the controller could understand the relationship between the various system elements and coordinate frames and be capable of transforming motions in one coordinate frame into similar motions in another coordinate frame. In the embodiment schematically illustrated in FIG. 30, a user can perform an action at the user input device ($C_1$) while presented with a displayed view ($C_2$) of an anatomical model and distal portion of the catheter. The controller could transform the sensed user input motion into a corresponding motion of the proximal actuators of the manipulator ($C_5$). The proximal actuation of the manipulator causes a movement of the distal catheter tip ($C_6$), which is registered by the positioning system ($C_4$) and fed into the model database ($C_3$). The controller could then transform the updated three dimensional model ($C_3$) into a particular two dimensional view for display to the user via the display device ($C_2$).

An embodiment of the control scheme will now be discussed with regard to FIG. 31.

Figure 31:
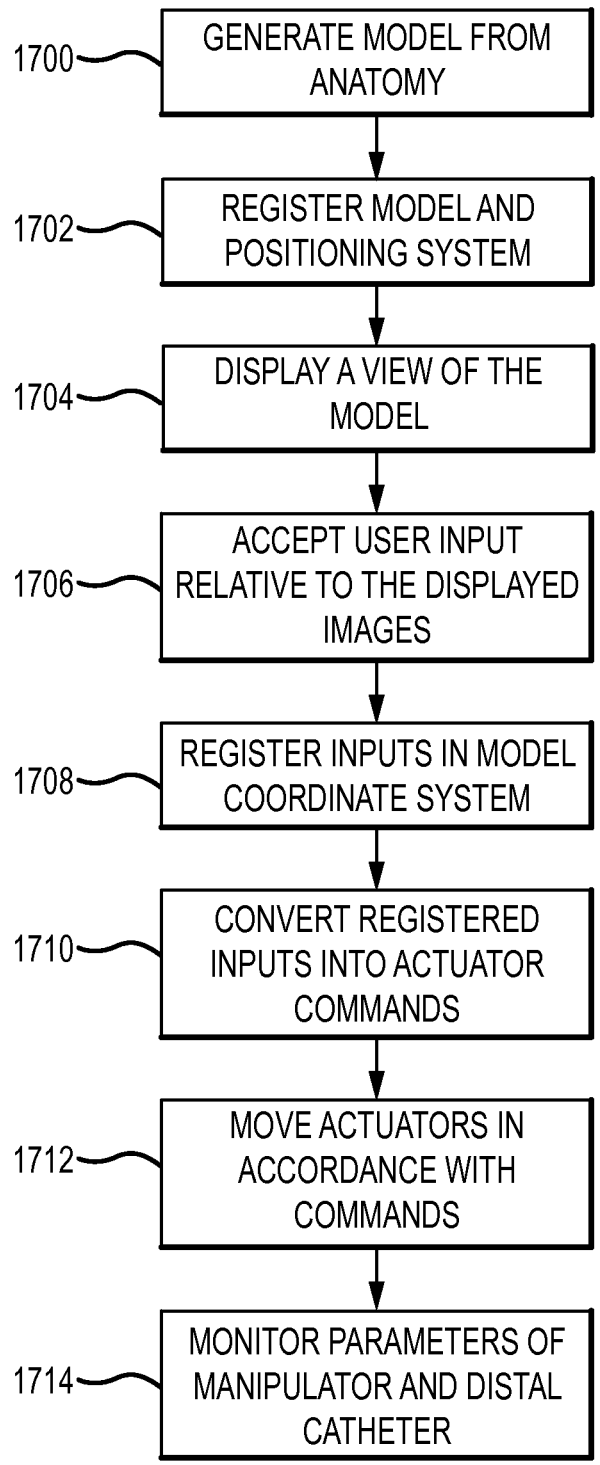
FIG. 31 is a flow chart illustrating an embodiment of a robotic catheter control scheme.

As generally represented by the flowchart in FIG. 31, a model representing the subject's anatomy could first be generated (1700) and registered (1702) to the real-time positioning system. The controller can then display a particular view of the model (1704), and accept user inputs relative to the displayed model (1706) and register them in the model coordinate system (1708). Using the current position of the catheter, along with the registered user input, the controller can compute the necessary manipulator actuation required to move the catheter as intended by the user (1710). The controller then can command the actuators to move in accordance with the computed actuation commands (1712) and monitor parameters of the manipulator and distal catheter tip (1714). Further detail relating to each step will be provided below.

In an embodiment, a model of the operative site is first generated from the physical anatomy of the subject (1702). This generated model can serve as a basis or a reference for the physician's control, and should reflect the features of the subject's anatomy. The model can be generated by, for example, using pre-existing MRI or CT imagery, or can be generated by monitoring the real-time movement of an invasive probe, such as with the EnSite NavX™ system available from St. Jude Medical. In the case of a probe, axes of a coordinate system can be generated between pairs of patch electrodes located on the skin of the patient (such as described in detail in U.S. Pat. No. 7,263,397, titled "Method and Apparatus for Catheter Navigation and Location and Mapping in the Heart," incorporated by reference in its entirety). A catheter with a position sensing electrode can be swept around the internal geometry while it communicates its position relative to the pairs of electrodes to the controller. Through either contact sensing means or various skinning techniques, a shell can be constructed around the outermost points of the recorded three dimensional data cloud. This shell can then be the basis of the anatomical model maintained by the controller. Likewise, other similar positioning/modeling systems can be used to generate the stored anatomical model. Such systems can include, for example, the Mediguide gMPS system, or the Biosense Webster CARTO system.

In an embodiment where the model is generated by a real-time positioning system such as EnSite NavX™, the registration (1702) can be implicit (i.e., $C_3=C_4$), where no further registration is needed. If other real-time factors (e.g., breathing and/or respiration) are sensed by the positioning system, however, a registration can still be necessary. Alternatively, in an embodiment where the model is imported from previously acquired CT or MRI imagery, the model can be registered to the coordinate system of the real time positioning system through scaling and/or rotating techniques such as those provided by the EnSite Fusion dynamic registration system, commercialized by St. Jude Medical.

In a configuration where the physician makes input movements with respect to a third person view of a displayed catheter and anatomic model, the physician could first select a viewing perspective from which to perceive the model (1704). This can be accomplished through the use of a display controller. The display controller can allow the physician to manipulate the displayed view of the anatomic model, and can include, for example, a 3D mouse, or spaceball such as those commercially available from 3Dconnexion, or can include various on-screen controls that would allow the user to pan, zoom, and/or rotate the model.

In operation, as generally illustrated in the display controller can serve to manipulate a projection of the 3D model onto the 2D display by first rotating/translating the model in 3D space, and then projecting the model onto a 2D viewing plane. The rotation/translation can be accomplished using a homogeneous model view transformation matrix ($T_V$). In an embodiment, the model view transformation matrix ($T_V$) can be of the form shown in Equation 1, where the 3×3 matrix of $R_{1-9}$ relates to a rotation of the model in three dimensional space, and the 3×1 matrix of $T_{1-3}$ relates to a translation of the model in three dimensional space.

$$T_V = \begin{bmatrix} R_1 & R_2 & R_3 & T_1 \\ R_4 & R_5 & R_6 & T_2 \\ R_7 & R_8 & R_9 & T_3 \\ 0 & 0 & 0 & 1 \end{bmatrix} \quad (\text{eq. 1})$$

Figure 32:
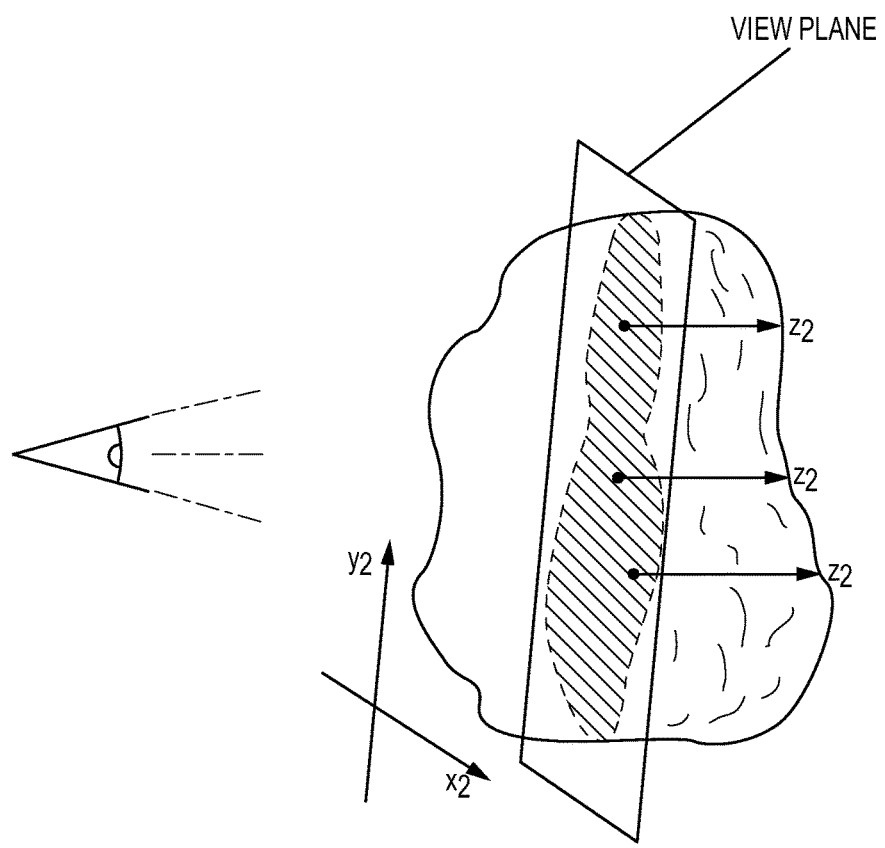
FIG. 32 illustrates a projection of an anatomical model to a viewing plane according to an embodiment.

Such model view transformation matrices are commonly implemented through high-level commands in rendering applications, such as OpenGL, and ultimately have the effect of repositioning or rotating a model in front of a fixed camera. Once the model is positioned in three dimensional space, it can then be projected to a two dimensional viewing plane, as generally illustrated in FIG. 32. At this stage, the system can internally buffer a transverse depth value (i.e., $z_2$) for each two dimensional primitive or point depicted within the viewing plane. Once the model is projected to the viewing plane, it can be displayed to a user on a two dimensional computer monitor. The user then can use the displayed projection of the anatomical model as a reference while providing an input to the input device.

As described above, the user can indicate intended movements of the catheter to the system by using an input device. Potential input devices can include, for example, a two or three dimensional mouse or joystick, a spatially detected stylus, a touch screen, or other similar forms or input. As generally described above, the user can specify this intended movement in a manner that directly moves the catheter tip across the screen similar to controlling a computer pointer arrow with a computer mouse. Alternatively, the user can select a point along the catheter and drag it across the screen similar to dragging an icon across a computer desktop. In yet another embodiment, the user can use the input device to specify waypoints or target points within the model for semi-automated or fully-automated movement.

Referring back to FIGS. 29a, 29b, in an embodiment, the coordinate frame of the input device (e.g., $C_1$) can be aligned with the coordinate system of the display (e.g., $C_2$), such that a leftward movement of the input device can cause a corresponding leftward movement of an object on the display (e.g., a negative $x_1$ movement of the input device would correspond to a negative $x_2$ motion within the display). By knowing the relationship between the displayed view ($C_2$) and the model coordinate system ($C_3$) (e.g., via the model view transformation matrix, $T_V$) the system can be configured to then relate the input movement (e.g., $C_1$) into the model coordinate system ($C_3$). This relation can generally be expressed by equation 2, where $T_V^T$ is the transpose of the model view transformation matrix ($T_V$), and s represents an scaling factor that can be applied to scale the user input.

$$\begin{bmatrix} x_3 \\ y_3 \\ z_3 \\ 1 \end{bmatrix} = sT_V^T \begin{bmatrix} x_1 \\ y_1 \\ (z_1) \\ 1 \end{bmatrix} \quad (\text{eq. 2})$$

As used in equation 2, ($z_1$) represents the out-of-plane movement of the input device. While in some embodiments, the input device can only be capable of two dimensional movement, this third dimension can be directly obtained from the device if, for example, a three dimensional input device, such as a 3D joystick, is used. Alternatively, when using a two-dimensional input device, this third dimension can be obtained from another input such as the rotation of a wheel. In another embodiment, ($z_1$) can be maintained as a constant that constrains the catheter's orthogonal motion to a plane that bisects the catheter's current position, and is parallel to the current viewing plane. If held as a constant, the catheter can be maneuvered in three dimensions by first rotating the view using the display controller, and then moving the catheter in the new viewing plane. In yet another embodiment, ($z_1$) can be retrieved from the stored $z_2$ buffer (i.e., the stored depth for each displayed point or primitive). In this manner, once a user selects a point on the display, the point can be immediately projected to the surface of the displayed anatomy. In an embodiment, the display can further provide an auxiliary view to aid the user in perceiving depth. It should also be understood that if the input device is configured to convey information regarding its orientation, equation 2 can be expanded to account for such rotation.

In still another embodiment, ($z_1$) can be allowed to vary freely based on the bending mechanics of the catheter while the directional bending of the catheter is controlled by the user. In such an embodiment, the manipulator can be constrained against automatic translation, and a directional movement in, for example, a two-dimensional input space (e.g., $C_1$) or two-dimensional display-space (e.g., $C_2$) would cause an inherent bending motion in the catheter. As such, ($z_1$) can be determined based on a knowledge of the current catheter pose, together with the direction of intended movement $\{x_1, y_1\}$, and an understanding of the bending mechanics of the catheter.

In an embodiment where the user appears to directly control a displayed catheter or sheath, the system can be configured so that the user is actually controlling a dynamic target point that is independent of the catheter. The system can be configured to cause the actual catheter to track this dynamic target point a closely as possible, though to the user, the point can either not be displayed or be displayed as a marker. In an alternative embodiment, the target point can be displayed as a catheter, while the real-time catheter position can be displayed as a ghost-catheter (as generally illustrated in FIG. 19b) (or vice-versa). This indirect control can be necessary in a system where the position and orientation of the displayed catheter reflects the position and orientation of the actual catheter as detected by the positioning system. In an embodiment where the input device incorporates an activation or safety switch, the dynamic target point can initially be set to the current position of the catheter. Upon actuation of the activation switch, the target point can be allowed to move from the current catheter position based on the motion of the input device. Upon release of the activation switch, the target point can be returned to the new-current position of the device, or locked to its position at the time of release.

Figure 33:
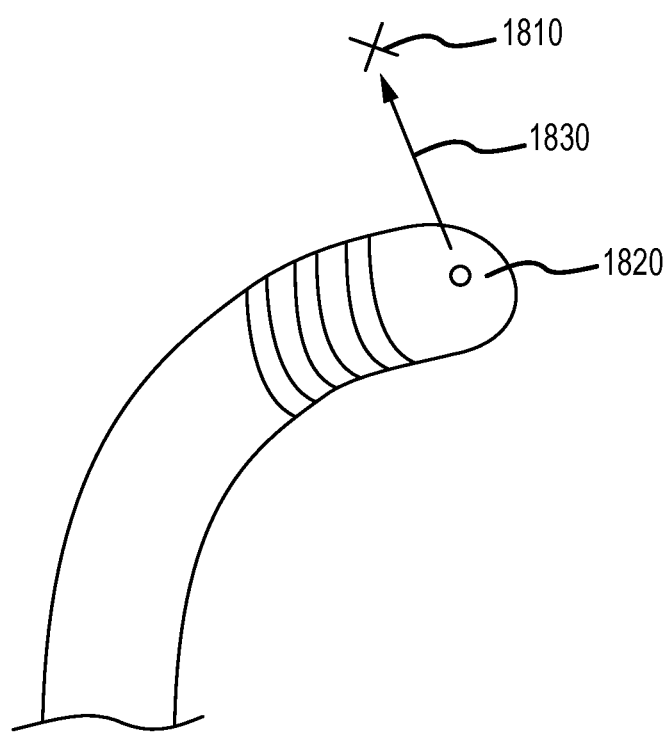
FIG. 33 illustrates an incremental catheter movement vector.

As generally illustrated in FIG. 33, once a desired movement is registered within the model, the dynamic target point (e.g., point 1810) or waypoint can be compared to the current position of the actual catheter 1820. The controller can use this comparison to create a desired movement vector 1830 that points in the direction of the intended movement. While the desired movement vector 1830 can reflect the desired movement of the distal portion of the catheter, the manipulator is unable to directly reproduce this motion. Instead, the manipulator could indirectly attempt to achieve such motion by controlling the proximal actuation inputs (e.g., $\{\lambda_1, \lambda_2, \lambda_3, \lambda_4, \lambda_T\}$). To accomplish this, the controller can use a knowledge of the catheter dynamics to determine the proximal actuation that would be required to cause the desired distal motion. In general, as illustrated in FIG. 34, the system's "forward kinematic" relationships describe how known inputs (e.g., $\{\lambda_1, \lambda_2, \lambda_3, \lambda_4, \lambda_T\}$) cause a resulting movement of the distal end of the catheter (e.g., $\{x_6, y_6, z_6\}$ or $\{\theta_6, \varphi_6, L_6\}$). Likewise, "inverse kinematic" relationships operate in an opposite manner, where the system can compute the inputs that would result in a desired movement or pose.

Figure 35:
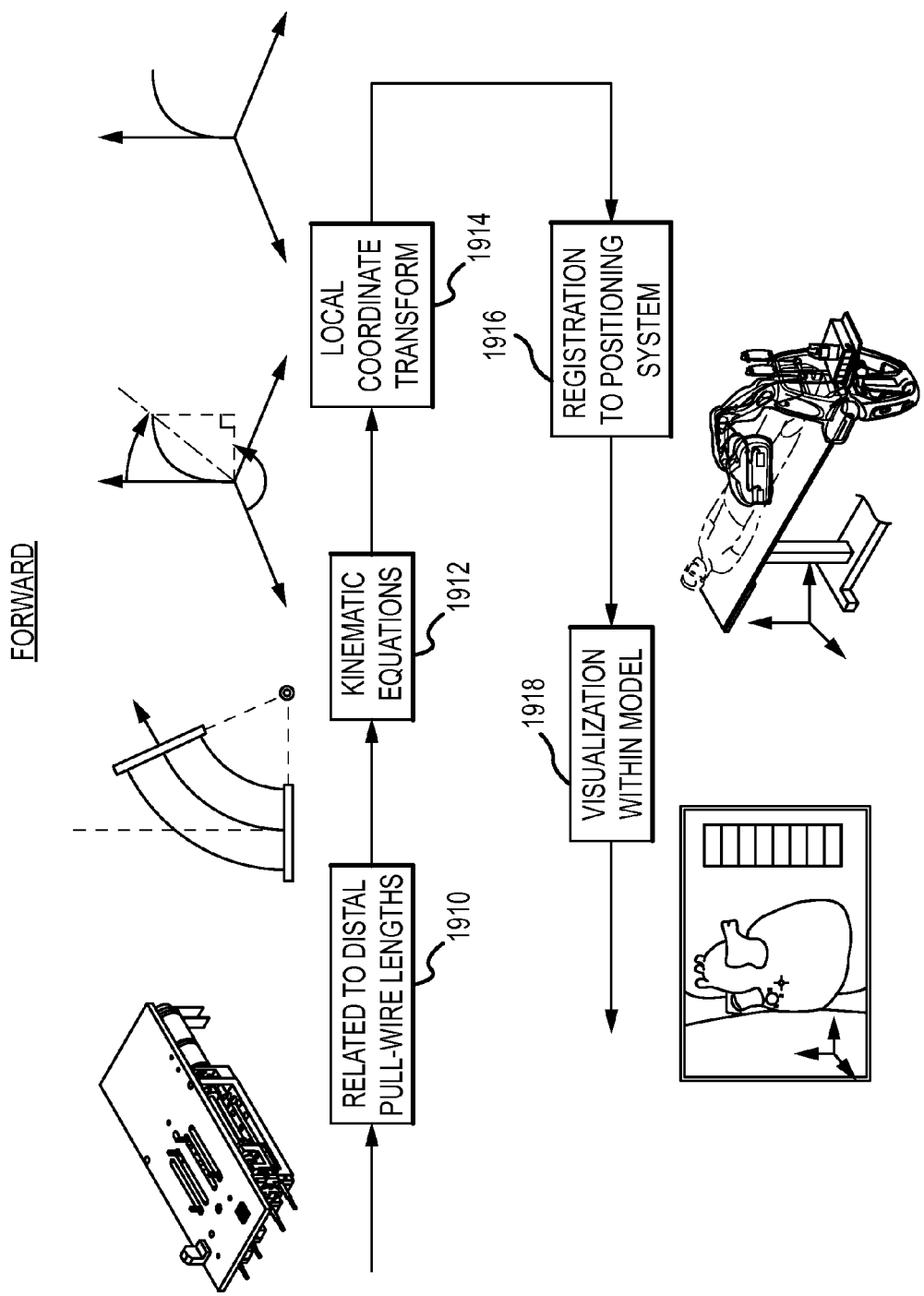
FIG. 35 is an illustration of an embodiment of a forward kinematic relationship.

FIG. 35 further illustrates an embodiment of the forward kinematics of a robotic catheter system. In step 1910, known inputs (e.g., $\{\lambda_1, \lambda_2, \lambda_3, \lambda_4, \lambda_T\}$) can be related to steering wires lengths (e.g., $\{L_A, L_B, L_C, L_D\}$) that extend between a distal fulcrum point and a pull ring. Through the use of known kinematic relationships, in step 1912, these steering wire lengths can be used to understand the deflection characteristics of the distal portion of the catheter (e.g., $\{\theta_6, \varphi_6, L_6\}$). This characterization of the current pose can then be converted into a local Cartesian reference frame (e.g., $\{x_6, y_6, z_6\}$) through a coordinate transform in step 1914. In step 1916, the local Cartesian reference frame can then be registered to the coordinate system of the positioning system (e.g., $\{x_4, y_4, z_4\}$), which can subsequently be registered to a particular model coordinate system (e.g., $\{x_3, y_3, z_3\}$) in step 1918.

Figure 36:
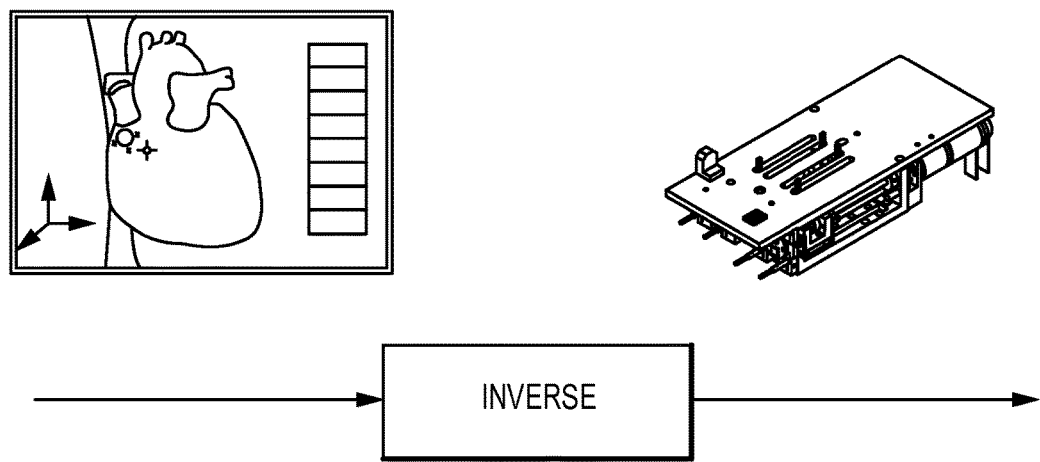
FIG. 36 is an illustration of an embodiment of an inverse kinematic relationship.

Using these "forward" relationships, the system can accurately predict how a particular manipulator actuation (often referred to as "joint variables") would affect the catheter position registered within the model. This, however, is the direct opposite of the relationships needed from a control perspective. As generally illustrated in FIG. 36, in an embodiment of the robotic catheter system, the system could be able to convert desired movements from within the model into actuation inputs that would result in the desired movement. While the inverse kinematic relationships can be theoretically derived, they can also be computed by numerically inverting the forward kinematics. Numerical inversion, such as through pseudo-inverse Jacobian methods, is an often-used method of determining the inverse kinematic relationships when the system is highly complex or nonlinear.

Beginning with the forward kinematics as shown in FIG. 35, in step 1910, the proximal actuation (e.g., $\{\lambda_1, \lambda_2, \lambda_3, \lambda_4, \lambda_T\}$) could first be related to the behavior of the steering wires between a distal fulcrum point and a pull ring (i.e., within the "bendable portion"). In an embodiment, it can be assumed that the changes in the lengths of the steering wires within the bendable portion directly relate to the proximal steering wire actuation by the manipulator (i.e. $\{\Delta L_A, \Delta L_C\} \approx \{\Delta \lambda_1, \Delta \lambda_3\}$). In another embodiment, length measurements can be taken directly from the steering wires within the bendable portion by, for example, passing a known current through the steering wire and measuring the voltage drop in the wire between a fixed point at the fulcrum and the distal pull ring (described in detail in commonly owned and copending application titled "Catheter with Pull Wire measurement Feature," filed 2 Mar. 2010 as U.S. patent application Ser. No. 12/716,056, which is hereby incorporated by reference herein in its entirety). By knowing the applied current, the voltage drop, and the resistance per unit length of the wire, the controller can determine the length of wire between the fixed fulcrum point and the pull ring.

Figure 37A:
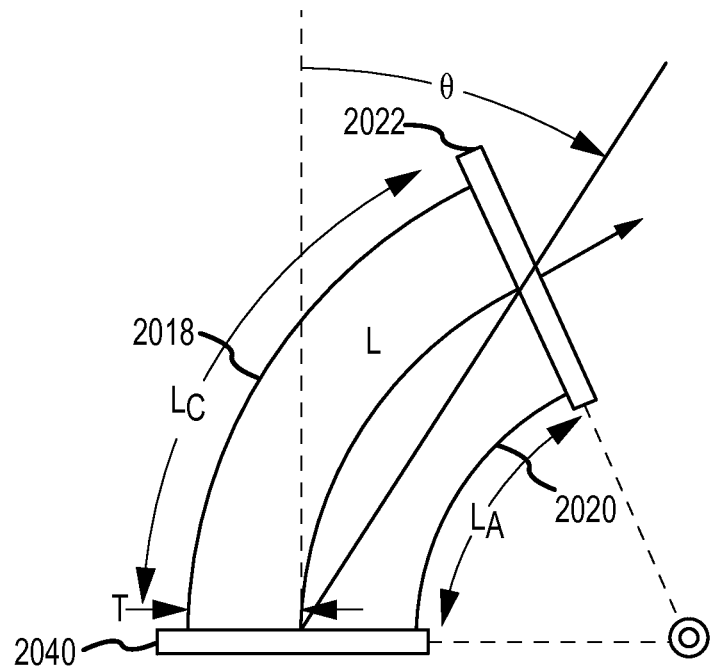
FIGS. 37a-37b are schematic representations of a bendable portion of a catheter illustrating, respectively, a deflection angle and a heading angle.
Figure 37B:
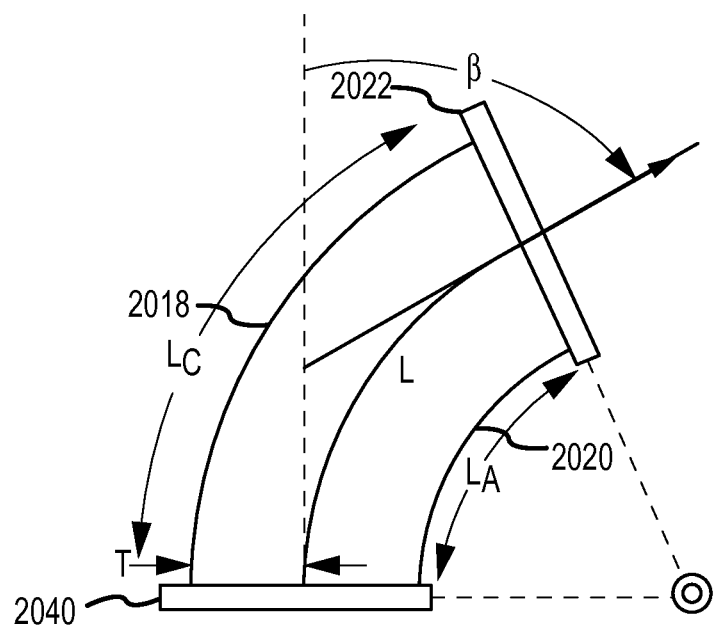

Once the steering wire lengths (e.g., $\{L_A, L_B, L_C, L_D\}$) within the bendable portion are known, the system can use known relationships to compute the deflection characteristics of the distal portion of the catheter. As illustrated in FIGS. 37a, 37b, in a two-steering wire configuration, where a constant curvature is assumed, the planar deflection of the bendable portion of the catheter can generally be expressed as a function of the nominal length (i.e., length L) of the catheter between fulcrum point 2040 and pull ring 2022 (the "bendable portion"), and either a deflection angle $\theta$ or heading angle $\beta$. Assuming a uniform thickness 2 T and a knowledge of the steering wire lengths within the bendable portion (i.e., lengths $L_A$, $L_C$), the nominal length L can be determined using equation 3, and deflection angle $\theta$ can be determined using equation 4. Furthermore, in a planar configuration, the heading angle $\beta$ is generally twice the deflection angle $\theta$.

$$L = \frac{L_A + L_C}{2} \quad \text{(eq. 3)}$$

$$\theta = \frac{L_C - L_A}{2} \times \frac{1}{2T} \quad \text{(eq. 4)}$$

Figure 38:
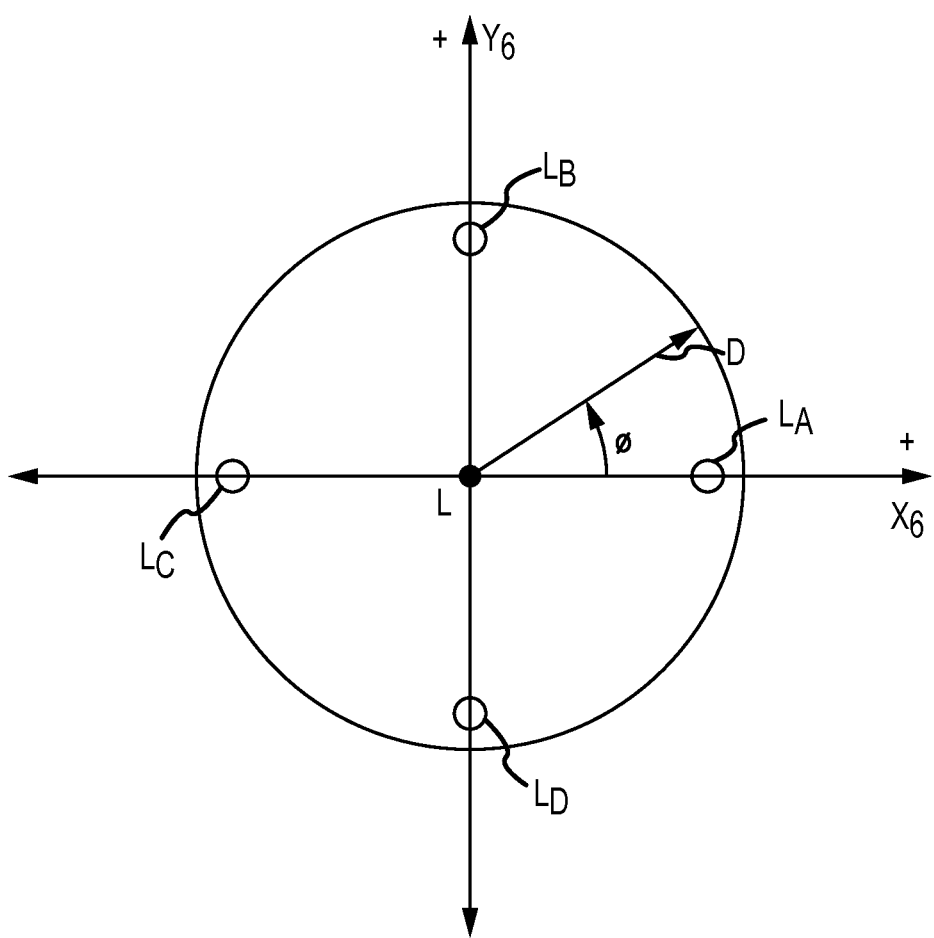
FIG. 38 is an illustration of a cross section of a catheter.

In a four steering wire embodiment, as illustrated in the cross-sectional view shown in FIG. 38 (taken of a four steering wire catheter at fulcrum point 2040), the calculation of the nominal length L can be affected by all four steering wire lengths $\{L_A, L_B, L_C, L_D\}$, as referenced in equation 5. Further, the deflection angle $\theta$, can be determined using the relationship expressed in equation 6, and the azimuth angle $\varphi$ can be determined through the relationship in equation 7.

$$L = \frac{L_A + L_B + L_C + L_D}{4} \quad \text{(eq. 5)}$$

$$\theta = \pm \sqrt{(L_A - L)^2 + (L_B - L)^2} \times \frac{1}{2T} \quad \text{(eq. 6)}$$

$$\phi = \quad \text{(eq. 7)}$$

$$\arctan\left(\frac{L_B - L}{\pm \sqrt{(L_A - L)^2 + (L_B - L)^2}}, \frac{L_A - L}{\pm \sqrt{(L_A - L)^2 + (L_B - L)^2}}\right)$$

As referenced in Step 1914 of FIG. 35, these local pseudo-spherical coordinates (i.e., $\{\theta_6, \varphi_6, L_6\}$) can then be transformed into a local Cartesian coordinate frame $\{x_6, y_6, z_6\}$, where $z_6$ is aligned with the longitudinal axis of the catheter at the fulcrum point, and $x_6$, for example, is aligned with steering wire "A" (as shown in FIG. 38). Alternatively, it should be understood that the local catheter position can directly be computed in a Cartesian reference frame, without the use of any intermediate reference frame.

In another embodiment, instead of using closed-form analytical modeling to understand how inputs (e.g., steering wire lengths $\{L_A, L_B, L_C, L_D\}$) relate to local movement in the bendable section (e.g., $\{x_6, y_6, z_6\}$), the system can employ empirical modeling techniques to model the catheter's behavior. These techniques can use actual observations to describe and predict how an object will behave, rather than relying on mathematically describable relationships. Examples of such empirical modeling techniques include neural network techniques such as without limitation, recurrent neural network modeling, or hysteretic recurrent neural network modeling. A hysteretic recurrent neural network model, for example, can accept the steering wire lengths and past local tip positions as inputs to the network, and can be configured to determine a resultant position from this information. The model can be trained prior to the actual procedure by experimentally manipulating the catheter throughout its full range of motion, or a portion of the full range of motion, and inputting the measured parameters and poses into the network to refine the model. These relationships can be determined from a catheter that is substantially similar in design or construction to the catheter that will be used in the procedure. The empirical model can reflect the kinematic properties of the catheter or sheath, and can be configured to account for material non-linearities, such as plastic deformation or axial compression, that can develop through use.

While local modeling, such as shown in equations. 5-7, can provide a useful insight into the mechanics of the distal catheter bending, the motions (i.e., $\{x_6, y_6, z_6\}$ or $\{\theta_6, \varphi_6, L_6\}$) are computed in a catheter-centric relative coordinate frame. As described above, however, the user desired catheter motions are specified in the coordinate system of the model/positioning system. Therefore, as referenced in Step 1916 of FIG. 35, the system can be configured to register the relative catheter-centric coordinate frame $\{x_6, y_6, z_6\}$ to the coordinate frame of the positioning system (i.e., $\{x_4, y_4,$ $z_4$}). This registration can achieved by computing a homogeneous catheter transformation matrix ($T_C$) of the form shown in equation 8.

$$T_C = \begin{bmatrix} i_x & i_y & i_z & t_x \\ j_x & j_y & j_z & t_y \\ k_x & k_y & k_z & t_z \\ 0 & 0 & 0 & 1 \end{bmatrix} \quad \text{(eq. 8)}$$

In an embodiment, $T_C$ can be computed empirically by physically moving the catheter through a series of positions and recording the coordinates of the catheter in both the catheter reference frame and the positioning system reference frame. The recorded point pairs can then be used, for example, in a regression analysis, to determine the values for $T_C$ that would satisfy the relationship expressed in equation 9, where $\vec{C}_4$ represents the points recorded by the positioning system, and $\vec{C}_6$ represents the points in the local catheter-centric reference frame.

$$\vec{C}_4 = T_C \bullet \vec{C}_6 \quad \text{(eq. 9)}$$

Figure 39:
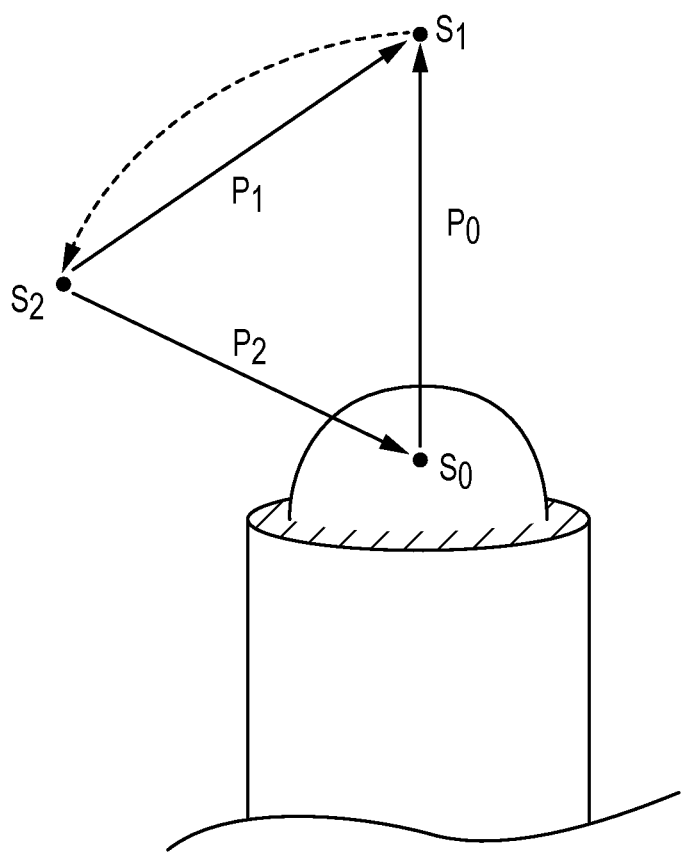
FIG. 39 is a representation of a catheter movement to accomplish a model registration.

In an embodiment, $T_C$ can be computed by recording the point pairs at a series of three points {$S_0$, $S_1$, $S_2$} as shown in FIG. 39, and represented in the following table:

| Point | $L_A$ | $L_B$ | $L_C$ | $L_D$ | L |
|---|---|---|---|---|---|
| $S_0$ | 0 | 0 | 0 | 0 | z |
| $S_1$ | 0 | 0 | 0 | 0 | z + Δz |
| $S_2$ | Δa | 0 | auto | 0 | z + Δz |

As used in the table, $L_A$, $L_B$, $L_C$, $L_D$ represent the lengths of four steering wires within the bendable section (in a four steering wire catheter embodiment), while L represents the axial translation of the catheter. Point $S_0$ can be specified such that the catheter is positioned slightly beyond the sheath, though in an undeflected state. The motion from $S_0$ to $S_1$ is accomplished by translating the catheter distally an amount Δz, such as an amount equal to the bendable length of the catheter. The motion from $S_1$ to $S_2$ is then accomplished by displacing pull wire "A" a distance Δa, sufficient to, for example, bring the catheter to a deflection angle of between π/4 and π/2. A value of 'auto,' as used in the table, indicates that while pull wire "A" is being displaced, pull wire C should be moved in such a manner to not impede the deflection of the catheter, though should also be auto-tensioned to prevent slack from developing.

Once points {$s_0$, $s_1$, $s_2$} are established, vectors {$\vec{P}_0$, $\vec{P}_1$, $\vec{P}_2$} can be defined within the coordinate frame of the positioning system and used to create a set of orthogonal basis vectors represented by equations 10-12.

$$\vec{K} = \vec{P}_0 \quad \text{(eq. 10)}$$

$$\vec{J} = \vec{P}_1 \times \vec{P}_2 \quad \text{(eq. 11)}$$

$$\vec{I} = \vec{K} \times \vec{J} \quad \text{(eq. 12)}$$

These vectors can then be normalized, and used to assemble the rotation portion of the homogeneous catheter transformation matrix referenced in equation 8. This rotation matrix is shown explicitly in equation 13.

$$R = \begin{bmatrix} i_x & i_y & i_z \\ j_x & j_y & j_z \\ k_x & k_y & k_z \end{bmatrix} \quad \text{(eq. 13)}$$

Furthermore, if $S_0$ is defined as the relative origin, for example, the transformation vector included in equation 8 can be determined through equation 14.

$$\vec{t} = -R\vec{s}_0 \quad \text{(eq. 14)}$$

Once the homogeneous catheter transformation matrix is assembled, it can be used via equation 9 to relate the computed local motion of the catheter into the coordinate system of the positioning system, as referenced in step 1918 of FIG. 35. In an embodiment, where the positioning system is registered to the model, the computed catheter motion can therefore be oriented and placed within the model. Thus the forward relationships, illustrated in FIG. 35, can be useful to analytically predict how a given actuation input can move the catheter within the patient, which in turn can be related to a movement of a model of the catheter within the anatomical model.

Using the relationships expressed above, and graphically illustrated in FIG. 35, a Jacobian matrix can then be constructed to directly relate a change in actuation inputs or actuation input motion (e.g., {$\lambda_1$, $\lambda_2$, $\lambda_3$, $\lambda_4$, $\lambda_T$} or {$L_A$, $L_B$, $L_C$, $L_D$}) into a change in distal tip position within the anatomical model (e.g., {$x_3$, $y_3$, $z_3$}), as illustrated in equations 15-16.

$$J = \begin{bmatrix} \frac{\partial x_3}{\partial L_A} & \frac{\partial x_3}{\partial L_B} & \frac{\partial x_3}{\partial L_C} & \frac{\partial x_3}{\partial L_D} & \frac{\partial x_3}{\partial L} \\ \frac{\partial y_3}{\partial L_A} & \frac{\partial y_3}{\partial L_B} & \frac{\partial y_3}{\partial L_C} & \frac{\partial y_3}{\partial L_D} & \frac{\partial y_3}{\partial L} \\ \frac{\partial z_3}{\partial L_A} & \frac{\partial z_3}{\partial L_B} & \frac{\partial z_3}{\partial L_C} & \frac{\partial z_3}{\partial L_D} & \frac{\partial z_3}{\partial L} \end{bmatrix} \quad \text{(eq. 15)}$$

$$\dot{X}_3 = J\dot{\vec{L}} \quad \text{(eq. 16)}$$

While a closed solution to the partial derivatives expressed in equation 15 can be difficult to compute, the derivatives can be approximated at a given point, by analyzing how small (delta) changes of the input motions affect the end-effecter coordinates at that point according to the model. To calculate these approximations, the controller can numerically apply a small perturbation to the current position of each of the distal steering wires ($\vec{L}$) in both the positive and negative direction. These perturbed motions can be passed through the forward kinematic model (illustrated in FIG. 35) and related to end effector motions (i.e., {$x_3$, $y_3$, $z_3$}). The partial differential approximation can then be calculated by dividing the estimated change in position by the change in distal steering wire motions, as shown in equation 17.

$$J_{approx} = \begin{bmatrix} \frac{\Delta x_3}{\Delta L_A} & \frac{\Delta x_3}{\Delta L_B} & \frac{\Delta x_3}{\Delta L_C} & \frac{\Delta x_3}{\Delta L_D} & \frac{\Delta x_3}{\Delta L} \\ \frac{\Delta y_3}{\Delta L_A} & \frac{\Delta y_3}{\Delta L_B} & \frac{\Delta y_3}{\Delta L_C} & \frac{\Delta y_3}{\Delta L_D} & \frac{\Delta y_3}{\Delta L} \\ \frac{\Delta z_3}{\Delta L_A} & \frac{\Delta z_3}{\Delta L_B} & \frac{\Delta z_3}{\Delta L_C} & \frac{\Delta z_3}{\Delta L_D} & \frac{\Delta z_3}{\Delta L} \end{bmatrix} \quad \text{(eq. 17)}$$

While the relationship expressed in equation 16 can be useful to predict a catheter motion for a given input, as explained above, the inverse of this function can be more useful from a control perspective. As shown in equation 18, the inverse Jacobian function can be used to relate a chance in desired catheter movement into the motions needed to obtain that desired result.

$$\dot{\vec{L}} = J^{-1} \dot{X}_3 \quad \text{(eq. 18)}$$

In general, however, the Jacobian Matrix (J) is not directly invertable. Therefore, in an embodiment, an approximation of $J^{-1}$ can be computed using linear algebra techniques. Such an approximation can rely on the pseudo-inverse methodology generally illustrated in equation 19, where $\lambda$ is a regularization value.

$$J^{-1} \approx J^T (JJ^T - \lambda I)^{-1} \quad \text{(eq. 19)}$$

When solving for $J^{-1}$, the controller can use the approximation of J (i.e., $J_{approx}$) calculated from equation 17. Since $J_{approx}$ is only valid at the point where it is computed, $J_{approx}^{-1}$ is also only valid for that same position. As the model catheter moves away from the position, $J_{approx}^{-1}$ can need to be recomputed to remain accurate. It should be recognized that $J_{approx}^{-1}$ can be calculated using various techniques, such as, for example, the singular value decomposition (SVD) technique. Once the matrix $J_{approx}^{-1}$ is calculated for a given catheter position, it can then be used, as shown in equation 20, to convert a desired movement within the model into the necessary actuator input (or distal steering wire movements) required to achieve that desired movement.

$$\dot{\vec{L}} = J_{approx}^{-1} \dot{X}_3 \quad \text{(eq. 20)}$$

Due to the inaccuracies caused by numerical approximations of the Jacobian and inverse Jacobian, in an embodiment where such approximations are used, a computed movement of the catheter can be made in a series of discrete steps, with the Jacobian approximation being recomputed at each discrete interval. In an embodiment where the catheter movement is configured to follow a constructed trajectory, as generally shown in FIGS. 28a-28b, the system can divide the trajectory into a series of incremental movements. At each increment, the controller can be configured to re-compute both $J_{approx}^{-1}$ and the incremental heading needed to arrive at the next interval location (such as the movement vector 1830 represented in FIG. 33). These updated values can then be used to compute a series of incremental manipulator inputs or distal steering wire motions that would cause the actual catheter to follow the desired trajectory.

Figure 40A:
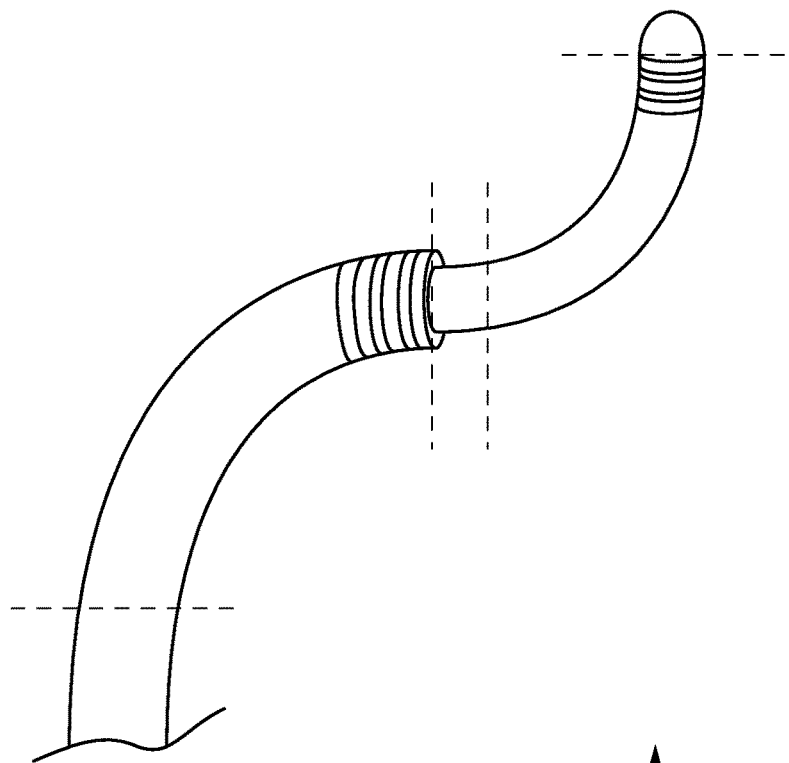
FIG. 40a-40b are illustrations of compound catheter-sheath movement.
Figure 40B:
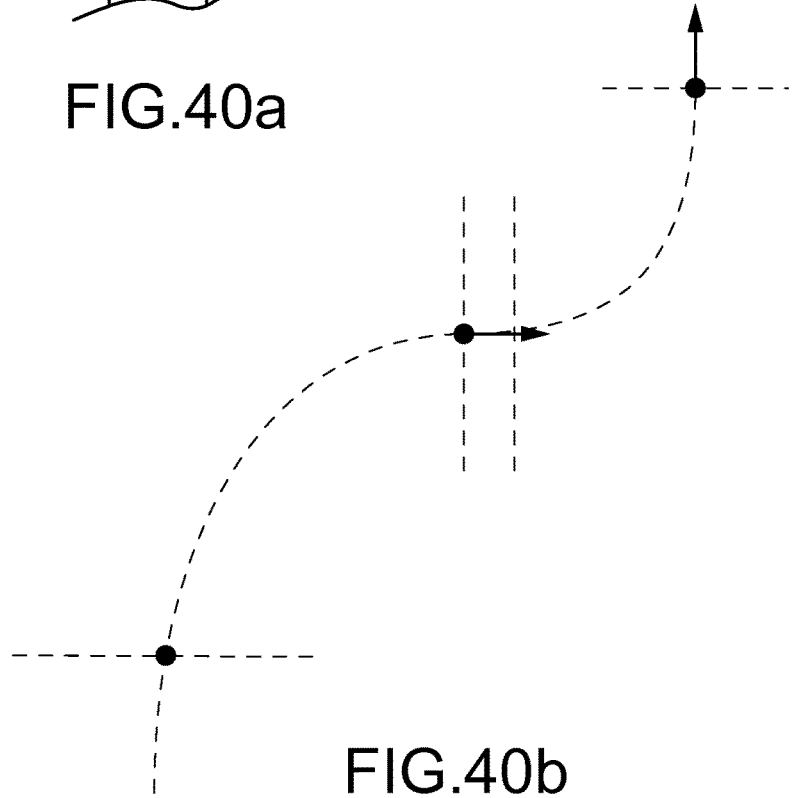

While the above description is made in terms of controlling the position of a point located at or near the pull ring of a catheter, it can likewise be possible to control the orientation of the catheter at that point. Furthermore, as described above, the system can comprise both an actively controlled catheter and an actively controlled sheath. In such a case, the controller can be configured to account for a greater number of input degrees of freedom, and the model can take into account the compound dynamics of the catheter/sheath combination, as generally shown in FIGS. 40a-40b.

Referring back to FIG. 31, once the desired manipulator inputs or distal steering wire motions are computed (1710), the controller can then instruct the manipulator to move the actuators in accordance with the computed motions (1712). In an embodiment where the controller is configured to compute incremental manipulator actuations $\Delta \vec{\lambda}$, the controller can command each respective actuator to move to a specified absolute location, or can command the respective actuators to move an incremental distance from their current position. In an embodiment that uses linear actuators to manipulate the steering wires, this motion can be achieved by directly monitoring and controlling the current linear position of the actuator in either an absolute or relative sense. In an embodiment where the linear motion is driven by a separate actuator, such as, for example, a servomotor driven ball screw, the system can first command the desired motion in terms of a linear position, or a change in a linear position of the actuator (e.g., the finger). Once this position is commanded, a secondary motor controller can receive feedback as to the current position of the actuator from, for example, an absolute or relative linear encoder or a potentiometer, and can then use known control techniques to manipulate the drive-servomotor in a manner that achieves the resultant linear motion.

Figure 41:
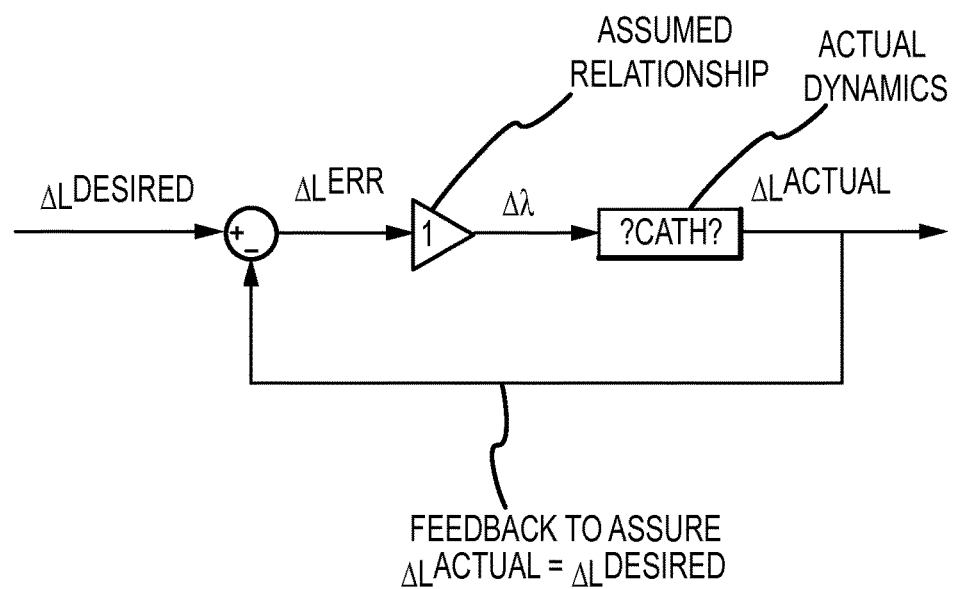
FIG. 41 is an embodiment of a catheter control diagram employing feedback.

In an embodiment where the controller specifies movement commands in terms of distal steering wire lengths (i.e., $\{L_A, L_B, L_C, L_D, L\}$), the controller can be configured to move the proximal actuators (e.g., fingers) while receiving feedback on the actual length change of the distal steering wires, as generally illustrated in FIG. 41. In an embodiment, the controller can initially assume that an incremental manipulator input $\Delta \vec{\lambda}$ directly corresponds to the same motion of the distal steering wire $\Delta \vec{L}$. The controller can then use a distal length measurement system, such as described above, to monitor the actual movement of the distal steering wires for the purpose of reducing any inaccuracies in the assumed relationship between the manipulator inputs and the distal steering wire movement.

Referring back to FIG. 31, after the controller moves the actuators in accordance with the initially computed trajectory, the system can then monitor various parameters of the manipulator and distal catheter. In an embodiment, the real-time position of the catheter, as sensed by the positioning system, can be monitored. This real-time position can be used, for example, to enhance the catheter's ability to accurately track a particular target or path, determine contact with an obstruction, or provide input to or further refine the kinematic model. In an embodiment, the system can monitor parameters generated by the distal portion of the catheter. Such parameters can include indication of physical contact through the use of various force sensors, an indication of electrical coupling through the use of electrical impedance monitoring, or an indication of tissue proximity through, for example, EnSite Contact proximity sensing. In an embodiment, the system can monitor parameters of the manipulator to detect workspace limitations and limitations on the amount of allowable exerted force. Examples of each of these forms of feedback will be described below.

In an embodiment where the real-time position in used to enhance the catheter's ability to track a particular target or path, the monitored position and orientation can be fed back to the controller in a closed-loop manner to account for model inaccuracies, external disturbances, or drift. The controller can be configured such that the system is either critically damped or overdamped and can cause the actual position of the distal catheter tip to rapidly converge to the desired position, though not permit the catheter to overshoot the desired position. Additionally, in an embodiment where the predicted model moves in an open-loop manner, (rather than path-tracking) positional feedback can be employed to dynamically compensate for inaccuracies in the kinematic model by periodically computing a model correction matrix. In an embodiment, the model correction matrix can be applied to the forward kinematic model, and can rotate and/or translate the position of the model catheter to reflect the sensed position/orientation of the actual catheter. This correction matrix can be maintained by the system and continuously adjusted and applied during control/movement iterations.

The catheter's actual position can also be used to infer contact with tissue by comparing the expected position with the actual position. If, during a movement, the system tensions one or more steering wires, as described above, the distal portion of the catheter is expected to bend in a predictable manner. If, during the process of tensioning, the catheter's observed movement does not correspond with the expected movement, it can be inferred that there is an obstruction preventing the expected movement. The system can be configured to likewise analyze the actual movement for changes or discontinuities in other relationships, such as for example, the speed of the movement $$\left(\text{e.g., } \frac{\partial X}{\partial t}\right),$$

or the rate of movement in view of the actuation inputs $$\left(\text{e.g., } \frac{\partial X}{\partial \lambda}\right).$$

Figure 42:
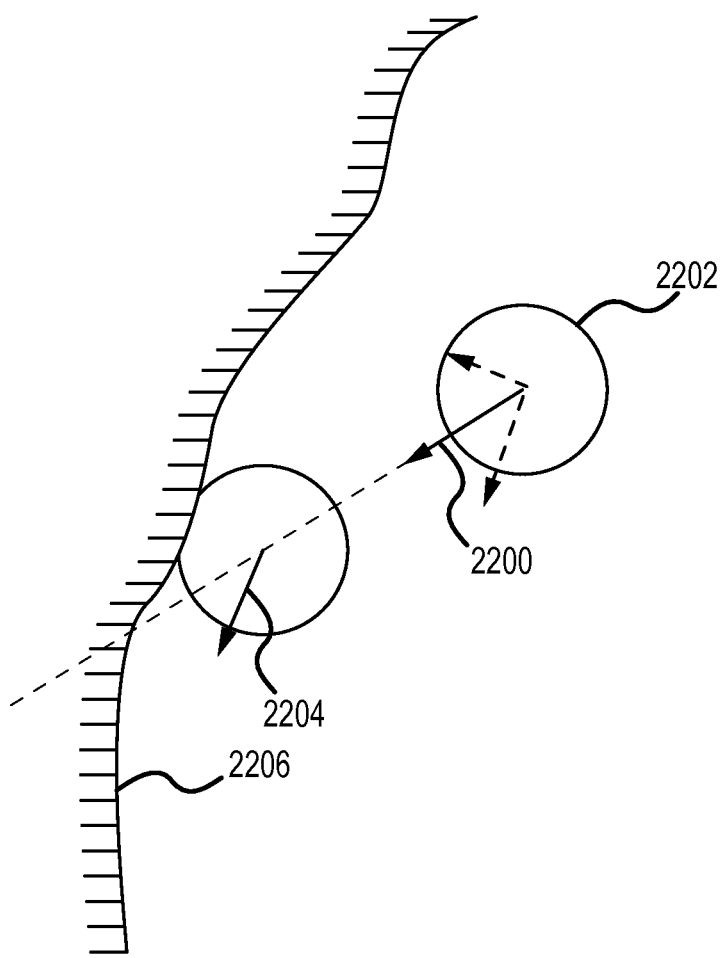
FIG. 42 is an illustration of a catheter movement from which contact can be deduced.

As the rate of movement decreases, potentially approaching zero, it can be inferred that the distal catheter tip has encountered an obstruction. If an obstruction is detected in this manner, the system can be configured to cease further movement or actuation. In an embodiment, the system can be configured to determine the contact direction by analyzing the heading of the catheter movement. If the heading (i.e., movement vector 2200) of the catheter 2202 unexpectedly changes direction (such as to new heading 2204), as shown in FIG. 42, the system can infer that an obstruction is preventing further movement in a direction normal to the surface 2206. In such an example, the component of the movement vector 2204 in a direction normal to the surface can be reduced to zero, while movement parallel to the surface can remain (though can be reduced in magnitude due to contact friction).

In an embodiment where the forward kinematic relationships are constructed through empirical modeling, such as, for example, hysteretic recurrent neural network modeling, the actual positional movement of the catheter in response to the steering wire inputs can be relied on to progressively train the model. Real-time feedback during a procedure can likewise be used to further refine the model if desired. Additionally, in an embodiment where the model is configured to account for past positions or hysteresis, the positional feedback can also be logged and provided to the model as an input.

As described above, the catheter used with the robotic catheter system can incorporate a sensor in the distal tip that is configured to provide an indication of physical contact between the catheter and an obstruction. Such sensors can include load cells, shape memory alloy based force sensors, piezoelectric force sensors, strain gauges, or optical-based or acoustic-based force sensors. If the catheter encounters tissue or another obstruction during operation, the contact or force sensor can be configured to provide an indication to the controller that such contact exists. Similar to contact sensing via position monitoring, if contact is detected, the controller can be configured to refrain from applying further force on the catheter in the direction of the sensed contact. Alternatively, the system can use the indication of the force to provide a controlled amount of force between the catheter and tissue that can be pre-set by the physician.

In an embodiment, the catheter can incorporate an electrode on its distal tip that is configured to provide an indication of the degree of electrical coupling between the catheter and tissue. (described in detail in U.S. patent application Ser. No. 12/622,488, titled "System and Method for Assessing Lesions in Tissue," incorporated by reference in its entirety). Such an indication can be based on a measured impedance and/or phase of a signal transmitted through the tissue, and can allow the system to determine the nature of the electrical coupling that exists. If the catheter is in inadequate electrical contact with the tissue, the system can, for example, alert the user, or automatically refine the position until an adequate measure of electrical coupling exists.

Figure 43:
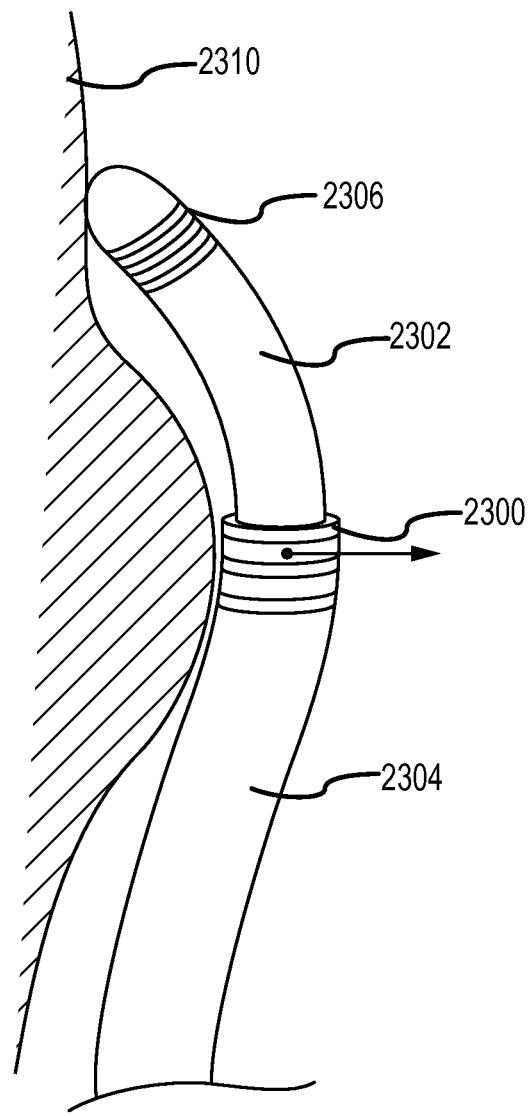
FIG. 43 is an illustration of a compound catheter-sheath movement for avoiding proximal obstructions.

As illustrated in FIG. 43, the catheter 2302 and/or sheath 2304 can further include one or more electrodes 2306, 2308 positioned along a length of the respective catheter and/or sheath to determine the proximity of tissue 2310 from the catheter/sheath body. In an embodiment, each electrode can monitor the impedance and/or phase of a signal transmitted through the tissue, provide it to the controller to compute an electrical coupling index (as described in the above referenced Ser. No. 12/622,488). The controller can use the computed coupling index to determine the relative distance between the catheter/sheath body and the tissue 2310 transmitting the signal. By knowing the location of the catheter/sheath with respect to the detected anatomy, the controller can be able to adjust the behavior of the catheter to favor either increased precision (e.g., when the catheter is immediately proximate to the tissue) or increased speed (e.g., when the catheter is away from the tissue). In an embodiment, the system can be configured to adjust the pose of the catheter/sheath to avoid contacting the tissue with the device body. As generally illustrated in FIG. 43, if proximity is detected between the body of the device and tissue, the device can be configured to translate the distal portion of the sheath near where the protruding obstruction is located. Once in position, the sheath can be caused to bend away from the protrusion, while the catheter is then bent back toward the tissue.

Other forms of feedback that can be available to the controller include feedback from the manipulator about the status of each actuator within the given workspace. As described above, each steering wire actuator and carriage can have a finite range of travel. As each is manipulated, it can draw closer to the limits on its range of travel. Therefore, the manipulator can be able to convey each actuator's current position with respect to the actuator's total range of motion. If an actuator nears or reaches a limit of its individual workspace or range of motion, the controller can be configured to prevent further attempted actuation and can alert the physician so that appropriate action can be taken. The manipulator can be configured to understand the full range of each actuator motion through, for example, the use of linear encoders coupled with each actuator, or the use of sensors, such as Hall effect sensors, at or near the limits of the available travel. In an embodiment, the limits can be hard coded as an absolute encoder count, or can be detected through an initialization routine prior to use.

In another embodiment, the manipulator can be configured to monitor the force exerted by each actuator. This indication of force can convey to the controller that the catheter or sheath have encountered an obstruction if the force becomes too great. Alternatively if the force applied on an actuator is lower than an acceptable range, it can signify a loss of contact between, for example, the actuator finger and the slider block. It can also signify that, for example, a steering wire's integrity has been compromised in some manner. One example of this can be a break in the coupling between the steering wire and the pull ring.

The robotic catheter system can be a useful tool in increasing the speed, precision, repeatability, and effectiveness of a particular procedure. It can allow the physician to control the catheter motion in intuitive ways that enable dynamic path planning and can allow for certain automated motions or procedures. It is necessary that during any automated movement, the actual catheter could traverse a given space without unintentionally contacting or attempting to pass through tissue. Therefore, the system can be configured to use a knowledge of the anatomical model geometry, a knowledge of the catheter dynamics, and/or available real-time feedback from the actual catheter to circumnavigate any obstacles or anatomical features. Additionally, while it is important to prevent the robotic catheter tip from unintentionally passing through tissue, contact between the tissue and a proximal portion of the catheter or sheath can serve to prevent the distal tip from reaching certain locations. In such a case, the catheter can be configured to account for proximal contact between the catheter or sheath and a particular anatomical feature.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure can be made without departing from the invention as defined in the appended claims.

What is claimed is:

1. A control system for user-guided robotic manipulation of a medical device comprising:
   an electronic control unit (ECU);
   a computer-readable memory coupled to said ECU;
   a visualization system configured to provide a view of an anatomical model;
   user interface (UI) logic stored in said memory configured to be executed by said ECU, said user interface logic configured to obtain input from a touch screen display with respect to said view of said anatomical model;
   control logic stored in said memory configured to be executed by said ECU, said control logic configured to produce an actuation control signal based at least in part on said input to control actuation of a manipulator assembly so as to move the medical device;
   a safety switch, said control logic, when said switch is actuated, controls said manipulator assembly to cause said medical device into retracing an immediately preceding path of movement. and
   wherein the ECU is configured to suppress recognition of said input from said touch screen display when predetermined criteria indicative of an inadvertent, incorrect, or too rapid touch is satisfied while the control system is in use, and wherein the ECU is configured to add a temporal delay after the input is entered into the touch screen to allow the input to be retracted or retraced before the actuation control signal is produced.

2. The control system of claim 1, wherein said safety switch comprises at least one of a foot pedal and a button on said touch screen display.

3. The control system of claim 1, further comprising a safety switch, said manipulator assembly being inoperative until said safety switch is actuated.

4. The control system of claim 1, wherein said UI logic is configured to obtain input comprising a touch with a deformable-tipped instrument from said touch display.

5. The control system of claim 1, wherein said UI logic is further configured to obtain input via said touch screen display corresponding to at least one of:
   designation of a targeted lesion location relative to said view;
   selection of one of a plurality of items from (i) a drop-down menu and (ii) a list;
   enlargement or reduction of a portion of said view;
   pan of a portion of said view;
   activation of a replay feature of a stored, temporally varying physiologic parameter;
   activation of a replay of a stored video clip;
   rotation of said view of said anatomical model;
   change one or more display attributes, including color and screen location;
   designation of automated motion targets on three-dimensional (3D) objects; and
   wherein said medical device includes at least a catheter and a sheath, selection of one or more of said catheter and sheath for navigation or manipulation.

6. The control system of claim 5, wherein said UI logic is further configured to obtain input corresponding to a manipulation mode for the medical device selected from the group comprising:
   a control point drag mode; and
   a target point mode.

7. The control system of claim 5, wherein said UI logic is further configured to obtain input corresponding to a manipulation mode relating to said view selected from the group comprising:
   a pan mode;
   a zoom mode; and
   a rotate mode.

8. The control system of claim 5, wherein said UI logic is further configured to obtain input corresponding to a desired operating mode selected from the group comprising:
   a combined translation and deflection mode;
   a translation-only mode; and
   a deflection-only mode.

9. The control system of claim 1, further comprising display logic stored in said memory configured to be executed by said ECU, said display logic configured to provide said view of said anatomical model from said visualization system for display on said touch screen display, said touch screen display being a first display, said display logic being further configured to drive a second display.

10. The control system of claim 9, wherein said first display is a multi-touch display.

11. The control system of claim 9, wherein said first display has a processor independent from said ECU.

12. The control system of claim 9, wherein said view is a first view, said display logic being further configured to provide a second view of an anatomical model for said second display.

13. The control system of claim 1, wherein said model comprises one of a three-dimensional (3D) geometry of an anatomical feature, a map of an electrophysiological (EP) parameter, and a 3D geometry or map of said anatomical feature from an imaging system.

14. The control system of claim 13 wherein said imaging system comprises one of a computed tomography (CT) system, a magnetic resonance imaging (MRI) system, an intra-cardiac echocardiography (ICE) imaging system.

15. A control system for user-guided robotic manipulation of a medical device comprising:
an electronic control unit (ECU);
a computer-readable memory coupled to said ECU;
a visualization system configured to provide a view of an anatomical model;
user interface logic stored in said memory configured to be executed by said ECU, said user interface logic configured to obtain input from a touch screen display with respect to said view of said anatomical model;
control logic stored in said memory configured to be executed by said ECU, said control logic configured to produce an actuation control signal based at least in part on said input to control actuation of a manipulator assembly so as to move the medical device;
a safety switch, said control logic, when said switch is actuated, controls said manipulator assembly to cause said medical device into retracing an immediately preceding path of movement, and
display logic stored in said memory configured to be executed by said ECU, said display logic configured to provide said view of said anatomical model from said visualization system for said touch screen display, and wherein said view includes a representation of said medical device;
wherein the ECU is configured to suppress recognition of said input from said touch screen display when predetermined criteria indicative of an inadvertent, incorrect, or too rapid touch is satisfied while the control system is in use, and wherein the ECU is configured to add a temporal delay after the input is entered into the touch screen to allow the input to be retracted or retraced before the actuation control signal is produced.

16. The control system of claim 15, wherein said view is a first view and said display logic is further configured to provide a second view of an anatomical model for said touch screen display.

17. The control system of claim 16, wherein said second view is orthogonal to said first view.

* * * * *